United States Patent
Delaney et al.

(10) Patent No.: US 11,884,964 B2
(45) Date of Patent: Jan. 30, 2024

(54) COMPOSITIONS, METHODS, AND SYSTEMS FOR BEAD FORMATION USING IMPROVED POLYMERS

(71) Applicant: 10x Genomics, Inc., Pleasanton, CA (US)

(72) Inventors: Joshua Delaney, Oakland, CA (US); Shalini Gohil, Castro Valley, CA (US); Christopher Hindson, Livermore, CA (US); Adam Lowe, Mountain House, CA (US); Andrew D. Price, Hayward, CA (US); Joseph Francis Shuga, Pleasanton, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

(21) Appl. No.: 17/861,503

(22) Filed: Jul. 11, 2022

(65) Prior Publication Data
US 2022/0364150 A1 Nov. 17, 2022

Related U.S. Application Data

(63) Continuation of application No. 17/009,352, filed on Sep. 1, 2020, now Pat. No. 11,441,172, which is a
(Continued)

(51) Int. Cl.
*C12Q 1/6806* (2018.01)
*B01J 13/18* (2006.01)
(Continued)

(52) U.S. Cl.
CPC ........ *C12Q 1/6806* (2013.01); *B01J 13/0065* (2013.01); *B01J 13/18* (2013.01);
(Continued)

(58) Field of Classification Search
CPC ........................................ C08J 3/075
See application file for complete search history.

(56) References Cited

U.S. PATENT DOCUMENTS

| 4,124,638 A | 11/1978 | Hansen |
| 5,185,099 A | 2/1993 | Delpuech et al. |

(Continued)

FOREIGN PATENT DOCUMENTS

| CN | 101849002 A | 9/2010 |
| CN | 102050953 B | 11/2012 |

(Continued)

OTHER PUBLICATIONS

10X Genomics, Inc. CG000153 Rev A. Chromium Single Cell DNA Reagent Kits User Guide. 2018.
(Continued)

*Primary Examiner* — Michael F Pepitone
(74) *Attorney, Agent, or Firm* — Wilson Sonsini Goodrich & Rosati

(57) ABSTRACT

The present disclosure provides systems and methods for making a hydrogel comprising a cell, cell nucleus, or one or more components derived from a cell or cell nucleus. A method for making a hydrogel may comprise providing a cell or cell nucleus, a first polymer, wherein the first polymer comprises a plurality of first crosslink precursors, each of the plurality of first crosslink precursors comprising an azide group; providing a second polymer, wherein the second polymer comprises a plurality of second crosslink precursors, each of the plurality of second crosslink precursors comprising an alkyne group; and crosslinking the first polymer and the second polymer via a reaction between a first section of the first crosslink precursors and a second section of the second crosslink precursors, thereby providing the hydrogel comprising the cell or cell nucleus.

19 Claims, 40 Drawing Sheets

Related U.S. Application Data continuation of application No. 16/374,112, filed on Apr. 3, 2019, now Pat. No. 10,837,047, which is a continuation-in-part of application No. 16/178,430, filed on Nov. 1, 2018, now Pat. No. 10,590,244, which is a continuation of application No. PCT/US2018/054458, filed on Oct. 4, 2018.

(60) Provisional application No. 62/687,161, filed on Jun. 19, 2018, provisional application No. 62/568,021, filed on Oct. 4, 2017.

(51) Int. Cl.
  *B01J 13/00* (2006.01)
  *C08J 3/075* (2006.01)
  *C12Q 1/6869* (2018.01)

(52) U.S. Cl.
  CPC .......... *C08J 3/075* (2013.01); *C08J 2333/00* (2013.01); *C12Q 1/6869* (2013.01)

(56) References Cited

U.S. PATENT DOCUMENTS

| | | |
|---|---|---|
| 5,270,183 A | 12/1993 | Corbett et al. |
| 5,478,893 A | 12/1995 | Ghosh et al. |
| 5,736,330 A | 4/1998 | Fulton |
| 5,756,334 A | 5/1998 | Perler et al. |
| 5,846,719 A | 12/1998 | Brenner et al. |
| 5,900,481 A | 5/1999 | Lough et al. |
| 5,942,609 A | 8/1999 | Hunkapiller et al. |
| 5,994,056 A | 11/1999 | Higuchi |
| 6,033,880 A | 3/2000 | Haff et al. |
| 6,057,149 A | 5/2000 | Burns et al. |
| 6,123,798 A | 9/2000 | Gandhi et al. |
| 6,171,850 B1 | 1/2001 | Nagle et al. |
| 6,172,218 B1 | 1/2001 | Brenner |
| 6,176,962 B1 | 1/2001 | Soane et al. |
| 6,306,590 B1 | 10/2001 | Mehta et al. |
| 6,327,410 B1 | 12/2001 | Walt et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,492,118 B1 | 12/2002 | Abrams et al. |
| 6,524,456 B1 | 2/2003 | Ramsey et al. |
| 6,586,176 B1 | 7/2003 | Trnovsky et al. |
| 6,632,655 B1 | 10/2003 | Mehta et al. |
| 6,915,679 B2 | 7/2005 | Chien et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,323,305 B2 | 1/2008 | Leamon et al. |
| 7,544,473 B2 | 6/2009 | Brenner |
| 7,622,076 B2 | 11/2009 | Davies et al. |
| 7,622,280 B2 | 11/2009 | Holliger et al. |
| 7,645,596 B2 | 1/2010 | Williams et al. |
| 7,708,949 B2 | 5/2010 | Stone et al. |
| 7,772,287 B2 | 8/2010 | Higuchi et al. |
| 7,776,927 B2 | 8/2010 | Chu et al. |
| 7,842,457 B2 | 11/2010 | Berka et al. |
| 7,910,354 B2 | 3/2011 | Drmanac et al. |
| 7,927,797 B2 | 4/2011 | Nobile et al. |
| 7,960,104 B2 | 6/2011 | Drmanac et al. |
| 7,968,287 B2 | 6/2011 | Griffiths et al. |
| 8,053,192 B2 | 11/2011 | Bignell et al. |
| 8,133,719 B2 | 3/2012 | Drmanac et al. |
| 8,168,385 B2 | 5/2012 | Brenner |
| 8,268,564 B2 | 9/2012 | Roth et al. |
| 8,273,573 B2 | 9/2012 | Ismagilov et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,329,407 B2 | 12/2012 | Ismagilov et al. |
| 8,592,150 B2 | 11/2013 | Drmanac et al. |
| 8,658,430 B2 | 2/2014 | Miller et al. |
| 8,822,148 B2 | 9/2014 | Ismagliov et al. |
| 8,835,358 B2 | 9/2014 | Fodor et al. |
| 8,846,883 B2 * | 9/2014 | Brown .................. C07H 1/00 536/26.6 |
| 8,871,444 B2 | 10/2014 | Griffiths et al. |
| 8,889,083 B2 | 11/2014 | Ismagilov et al. |
| 8,975,302 B2 | 3/2015 | Light et al. |
| 9,012,390 B2 | 4/2015 | Holtze et al. |
| 9,029,083 B2 | 5/2015 | Griffiths et al. |
| 9,029,085 B2 | 5/2015 | Agresti et al. |
| 9,085,798 B2 | 7/2015 | Chee |
| 9,089,844 B2 | 7/2015 | Hiddessen et al. |
| 9,126,160 B2 | 9/2015 | Ness et al. |
| 9,156,010 B2 | 10/2015 | Colston et al. |
| 9,194,861 B2 | 11/2015 | Hindson et al. |
| 9,216,392 B2 | 12/2015 | Hindson et al. |
| 9,238,206 B2 | 1/2016 | Rotem et al. |
| 9,266,104 B2 | 2/2016 | Link |
| 9,290,808 B2 | 3/2016 | Fodor et al. |
| 9,328,382 B2 | 5/2016 | Drmanac et al. |
| 9,347,059 B2 | 5/2016 | Saxonov |
| 9,371,598 B2 | 6/2016 | Chee |
| 9,388,465 B2 | 7/2016 | Hindson et al. |
| 9,417,190 B2 | 8/2016 | Hindson et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,593,365 B2 | 3/2017 | Frisen et al. |
| 9,623,384 B2 | 4/2017 | Hindson et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,701,998 B2 | 7/2017 | Hindson et al. |
| 9,764,322 B2 | 9/2017 | Hiddessen et al. |
| 9,824,068 B2 | 11/2017 | Wong |
| 9,868,979 B2 | 1/2018 | Chee et al. |
| 9,879,313 B2 | 1/2018 | Chee et al. |
| 9,946,577 B1 | 4/2018 | Stafford et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,030,261 B2 | 7/2018 | Frisen et al. |
| 10,059,989 B2 | 8/2018 | Giresi et al. |
| 10,221,436 B2 | 3/2019 | Hardenbol et al. |
| 10,221,442 B2 | 3/2019 | Hindson et al. |
| 10,253,364 B2 | 4/2019 | Hindson et al. |
| 10,273,541 B2 | 4/2019 | Hindson et al. |
| 10,323,279 B2 | 6/2019 | Hindson et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 | 9/2019 | Hindson et al. |
| 10,428,326 B2 | 10/2019 | Belhocine et al. |
| 10,533,221 B2 | 1/2020 | Hindson et al. |
| 10,544,413 B2 | 1/2020 | Bharadwaj et al. |
| 10,549,279 B2 | 2/2020 | Bharadwaj et al. |
| 10,590,244 B2 * | 3/2020 | Delaney .................. C08J 3/24 |
| 10,745,742 B2 | 8/2020 | Bent et al. |
| 10,752,949 B2 | 8/2020 | Hindson et al. |
| 10,774,374 B2 | 9/2020 | Frisen et al. |
| 10,815,525 B2 | 10/2020 | Lucero et al. |
| 10,829,815 B2 | 11/2020 | Bharadwaj et al. |
| 10,837,047 B2 * | 11/2020 | Delaney .............. C12Q 1/6806 |
| 10,874,997 B2 | 12/2020 | Weitz et al. |
| 10,995,333 B2 | 5/2021 | Pfeiffer |
| 11,155,881 B2 | 10/2021 | Bent et al. |
| 11,441,172 B2 * | 9/2022 | Delaney .............. C12Q 1/6806 |
| 11,459,607 B1 | 10/2022 | Terry et al. |
| 11,467,153 B2 | 10/2022 | Belhocine et al. |
| 11,655,499 B1 | 5/2023 | Pfeiffer |
| 2002/0005354 A1 | 1/2002 | Spence et al. |
| 2002/0051971 A1 | 5/2002 | Stuelpnagel et al. |

(56) References Cited

U.S. PATENT DOCUMENTS

| | | |
|---|---|---|
| 2002/0092767 A1 | 7/2002 | Bjornson et al. |
| 2002/0119455 A1 | 8/2002 | Chan |
| 2002/0127736 A1 | 9/2002 | Chou et al. |
| 2003/0036206 A1 | 2/2003 | Chien et al. |
| 2003/0075446 A1 | 4/2003 | Culbertson et al. |
| 2003/0124509 A1 | 7/2003 | Kenis et al. |
| 2003/0215862 A1 | 11/2003 | Parce et al. |
| 2005/0130188 A1 | 6/2005 | Walt et al. |
| 2005/0250147 A1 | 11/2005 | Macevicz |
| 2005/0266582 A1 | 12/2005 | Modlin et al. |
| 2005/0287572 A1 | 12/2005 | Mathies et al. |
| 2006/0177832 A1 | 8/2006 | Brenner |
| 2006/0275782 A1 | 12/2006 | Gunderson et al. |
| 2007/0020640 A1 | 1/2007 | McCloskey et al. |
| 2007/0042419 A1 | 2/2007 | Barany et al. |
| 2007/0172873 A1 | 7/2007 | Brenner et al. |
| 2007/0190543 A1 | 8/2007 | Livak |
| 2007/0196397 A1 | 8/2007 | Torii et al. |
| 2007/0264320 A1 | 11/2007 | Lee et al. |
| 2008/0056948 A1 | 3/2008 | Dale et al. |
| 2008/0166720 A1 | 7/2008 | Hsieh et al. |
| 2008/0242560 A1 | 10/2008 | Gunderson et al. |
| 2008/0299595 A1* | 12/2008 | Wong ............... G01N 33/582 435/70.1 |
| 2009/0011943 A1 | 1/2009 | Drmanac et al. |
| 2009/0047713 A1 | 2/2009 | Handique |
| 2009/0099041 A1 | 4/2009 | Church et al. |
| 2009/0131543 A1 | 5/2009 | Weitz et al. |
| 2009/0148961 A1 | 6/2009 | Luchini et al. |
| 2009/0155563 A1 | 6/2009 | Petsev et al. |
| 2009/0202984 A1 | 8/2009 | Cantor |
| 2009/0235990 A1 | 9/2009 | Beer |
| 2009/0269248 A1 | 10/2009 | Falb et al. |
| 2009/0286687 A1 | 11/2009 | Dressman et al. |
| 2010/0035254 A1 | 2/2010 | Williams |
| 2010/0069263 A1 | 3/2010 | Shendure et al. |
| 2010/0086914 A1 | 4/2010 | Bentley et al. |
| 2010/0105866 A1 | 4/2010 | Fraden et al. |
| 2010/0184928 A1 | 7/2010 | Kumacheva |
| 2010/0203647 A1* | 8/2010 | Hang ..................... C09B 29/12 534/752 |
| 2010/0216153 A1 | 8/2010 | Lapidus et al. |
| 2010/0248991 A1 | 9/2010 | Roesler et al. |
| 2010/0304982 A1 | 12/2010 | Hinz et al. |
| 2011/0217736 A1 | 9/2011 | Hindson |
| 2011/0293701 A1* | 12/2011 | Bratzler ............. A61K 39/0013 424/85.4 |
| 2011/0305761 A1 | 12/2011 | Shum et al. |
| 2012/0071331 A1 | 3/2012 | Casbon et al. |
| 2012/0172259 A1 | 7/2012 | Rigatti et al. |
| 2012/0196288 A1 | 8/2012 | Beer |
| 2012/0219947 A1 | 8/2012 | Yurkovetsky et al. |
| 2013/0028812 A1 | 1/2013 | Prieto et al. |
| 2013/0109575 A1 | 5/2013 | Kleinschmidt et al. |
| 2014/0065234 A1 | 3/2014 | Shum et al. |
| 2014/0155295 A1 | 6/2014 | Hindson et al. |
| 2014/0199331 A1* | 7/2014 | Robillard ........... A61K 47/6803 424/179.1 |
| 2014/0221239 A1 | 8/2014 | Carman et al. |
| 2014/0272996 A1 | 9/2014 | Bemis |
| 2014/0274740 A1 | 9/2014 | Srinivasan et al. |
| 2014/0302503 A1 | 10/2014 | Lowe et al. |
| 2014/0338753 A1 | 11/2014 | Sperling et al. |
| 2014/0378345 A1 | 12/2014 | Hindson et al. |
| 2015/0072396 A1* | 3/2015 | Gee ..................... C07D 213/74 435/188 |
| 2015/0125904 A1* | 5/2015 | Ting ..................... G01N 33/532 435/68.1 |
| 2015/0267191 A1 | 9/2015 | Steelman et al. |
| 2015/0361418 A1 | 12/2015 | Reed |
| 2015/0376605 A1 | 12/2015 | Jarosz et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0008778 A1 | 1/2016 | Weitz et al. |
| 2016/0024558 A1 | 1/2016 | Hardenbol et al. |
| 2016/0024572 A1 | 1/2016 | Shishkin et al. |
| 2016/0034093 A1 | 2/2016 | Xie et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0122753 A1 | 5/2016 | Mikkelsen et al. |
| 2016/0122817 A1 | 5/2016 | Jarosz et al. |
| 2016/0203196 A1 | 7/2016 | Schnall-Levin et al. |
| 2016/0232291 A1 | 8/2016 | Kyriazopoulou-Panagiotopoulou et al. |
| 2016/0244809 A1 | 8/2016 | Belgrader et al. |
| 2016/0281160 A1 | 9/2016 | Jarosz et al. |
| 2016/0289769 A1 | 10/2016 | Schwartz et al. |
| 2016/0303196 A1 | 10/2016 | Karin et al. |
| 2016/0314242 A1 | 10/2016 | Schnall-Levin et al. |
| 2016/0348093 A1 | 12/2016 | Price et al. |
| 2017/0016041 A1 | 1/2017 | Greenfield et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0235876 A1 | 8/2017 | Jaffe et al. |
| 2017/0260584 A1 | 9/2017 | Zheng et al. |
| 2018/0030515 A1 | 2/2018 | Regev et al. |
| 2018/0080075 A1 | 3/2018 | Brenner et al. |
| 2018/0105808 A1 | 4/2018 | Mikkelsen et al. |
| 2018/0273933 A1 | 9/2018 | Gunderson et al. |
| 2018/0312822 A1 | 11/2018 | Lee et al. |
| 2018/0312873 A1 | 11/2018 | Zheng |
| 2018/0340169 A1 | 11/2018 | Belhocine et al. |
| 2018/0340939 A1 | 11/2018 | Gaublomme et al. |
| 2018/0371545 A1 | 12/2018 | Wong et al. |
| 2019/0060890 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0127731 A1 | 5/2019 | McDermott |
| 2019/0134633 A1 | 5/2019 | Bharadwaj et al. |
| 2019/0153532 A1 | 5/2019 | Bharadwaj et al. |
| 2019/0176152 A1 | 6/2019 | Bharadwaj et al. |
| 2019/0177800 A1 | 6/2019 | Boutet et al. |
| 2019/0323088 A1 | 10/2019 | Boutet et al. |
| 2019/0345636 A1 | 11/2019 | McDermott et al. |
| 2019/0352717 A1 | 11/2019 | Schnall-Levin |
| 2019/0367997 A1 | 12/2019 | Bent et al. |
| 2019/0376118 A1 | 12/2019 | Belhocine et al. |
| 2020/0005902 A1 | 1/2020 | Mellen et al. |
| 2020/0032335 A1 | 1/2020 | Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0105373 A1 | 4/2020 | Zheng |
| 2020/0263232 A1 | 8/2020 | Bell et al. |
| 2020/0291454 A1 | 9/2020 | Belhocine et al. |
| 2020/0407775 A1 | 12/2020 | Bharadwaj et al. |
| 2021/0190770 A1 | 6/2021 | Delaney et al. |
| 2021/0270703 A1 | 9/2021 | Abousoud |
| 2022/0162671 A1 | 5/2022 | Pfeiffer et al. |
| 2022/0403375 A1 | 12/2022 | Martinez |
| 2023/0167496 A1 | 6/2023 | Bava |

FOREIGN PATENT DOCUMENTS

| | | |
|---|---|---|
| CN | 105582572 A | 5/2016 |
| EP | 1019496 B1 | 9/2004 |
| EP | 1841879 A2 | 10/2007 |
| EP | 2090592 A1 | 8/2009 |
| EP | 1967592 B1 | 4/2010 |
| EP | 2540389 A1 | 1/2013 |
| EP | 2635679 B1 | 4/2017 |
| GB | 2097692 A | 11/1982 |
| GB | 2097692 B | 5/1985 |
| WO | WO-84/02000 | 5/1984 |
| WO | WO-95/30782 | 11/1995 |
| WO | WO-9952708 A1 | 10/1999 |
| WO | WO-2000008212 A1 | 2/2000 |
| WO | WO-2001002850 A1 | 1/2001 |

(56) References Cited

FOREIGN PATENT DOCUMENTS

| | | |
|---|---|---|
| WO | WO-0114589 A2 | 3/2001 |
| WO | WO-0190418 A1 | 11/2001 |
| WO | WO-2001089787 A2 | 11/2001 |
| WO | WO-2004002627 A2 | 1/2004 |
| WO | WO-2004065617 A2 | 8/2004 |
| WO | WO-2004069849 A2 | 8/2004 |
| WO | WO-2004091763 A2 | 10/2004 |
| WO | WO-2005021151 A1 | 3/2005 |
| WO | WO-2005049787 A9 | 6/2005 |
| WO | WO-2005082098 A2 | 9/2005 |
| WO | WO-2006040551 A2 | 4/2006 |
| WO | WO-2006078841 A1 | 7/2006 |
| WO | WO-2006096571 A2 | 9/2006 |
| WO | WO-2007081385 A2 | 7/2007 |
| WO | WO-2007081387 A1 | 7/2007 |
| WO | WO-2007089541 A2 | 8/2007 |
| WO | WO-2007133710 A2 | 11/2007 |
| WO | WO-2007140015 A2 | 12/2007 |
| WO | WO-2007147079 A2 | 12/2007 |
| WO | WO-2008021123 A1 | 2/2008 |
| WO | WO-2008109176 A2 | 9/2008 |
| WO | WO-2008121342 A2 | 10/2008 |
| WO | WO-2008134153 A1 | 11/2008 |
| WO | WO-2008150432 A1 | 12/2008 |
| WO | WO-2009011808 A1 | 1/2009 |
| WO | WO-2009015296 A1 | 1/2009 |
| WO | WO-2009085215 A1 | 7/2009 |
| WO | WO-2009152928 A2 | 12/2009 |
| WO | WO-2010033200 A2 | 3/2010 |
| WO | WO-2010099818 A1 | 9/2010 |
| WO | WO-2010104604 A1 | 9/2010 |
| WO | WO-2010117620 A2 | 10/2010 |
| WO | WO-2010148039 A2 | 12/2010 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2012048341 A1 | 4/2012 |
| WO | WO-2012061832 A1 | 5/2012 |
| WO | WO-2012083225 A2 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012116250 A1 * | 8/2012 ............ A61L 27/18 |
| WO | WO-2012116331 A1 | 8/2012 |
| WO | WO-2012142531 A2 | 10/2012 |
| WO | WO-2012142611 A2 | 10/2012 |
| WO | WO-2012149042 A2 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013126741 A1 | 8/2013 |
| WO | WO-2013134261 A1 | 9/2013 |
| WO | WO-2014028378 A2 | 2/2014 |
| WO | WO-2014108810 A2 | 7/2014 |
| WO | WO-2014165559 A1 | 10/2014 |
| WO | WO-2015015199 A2 | 2/2015 |
| WO | WO-2015044428 A1 | 4/2015 |
| WO | WO-2015164212 A1 | 10/2015 |
| WO | WO-2016040476 A1 | 3/2016 |
| WO | WO-2016061517 A2 | 4/2016 |
| WO | WO-2016126871 A2 | 8/2016 |
| WO | WO-2016168584 A1 | 10/2016 |
| WO | WO-2017015075 A1 | 1/2017 |
| WO | WO-2017066231 A1 | 4/2017 |
| WO | WO-2017145476 A1 | 8/2017 |
| WO | WO-2017180949 A1 | 10/2017 |
| WO | WO-2017184707 A1 | 10/2017 |
| WO | WO-2017197343 A2 | 11/2017 |
| WO | WO-2017197343 A3 | 2/2018 |
| WO | WO-2018039338 A1 | 3/2018 |
| WO | WO-2018091676 A1 | 5/2018 |
| WO | WO-2018119301 A1 | 6/2018 |
| WO | WO-2018119447 A2 | 6/2018 |
| WO | WO-2018119447 A3 | 8/2018 |
| WO | WO-2018172726 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2019028166 A1 | 2/2019 |
| WO | WO-2019040637 A1 | 2/2019 |
| WO | WO-2019071039 A1 | 4/2019 |
| WO | WO-2019083852 A1 | 5/2019 |
| WO | WO-2019084043 A1 | 5/2019 |
| WO | WO-2019084165 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019134633 A1 | 7/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020041148 A1 | 2/2020 |
| WO | WO-2020142779 A1 | 7/2020 |
| WO | WO-2020167862 A1 | 8/2020 |
| WO | WO-2020167866 A1 | 8/2020 |
| WO | WO-2020168013 A1 | 8/2020 |
| WO | WO-2020198532 A1 | 10/2020 |
| WO | WO-2020206174 A1 | 10/2020 |
| WO | WO-2021046475 A1 | 3/2021 |
| WO | WO-2021133845 A1 | 7/2021 |
| WO | WO-2021207610 A1 | 10/2021 |
| WO | WO-2021212042 A1 | 10/2021 |
| WO | WO-2021/222302 A1 | 11/2021 |
| WO | WO-2021222301 A1 | 11/2021 |
| WO | WO-2022103712 A1 | 5/2022 |
| WO | WO-2022182682 A1 | 9/2022 |
| WO | WO-2022182785 A1 | 9/2022 |
| WO | WO-2022271908 A1 | 12/2022 |
| WO | WO-2023076528 A2 | 5/2023 |

OTHER PUBLICATIONS

10X Genomics, Inc. CG000184 Rev A. Chromium Single Cell 3' Reagent Kits v3 User Guide with Feature Barcoding Technology for CRISPR Screening. 2018.
10X Genomics, Inc. CG000185 Rev B. Chromium Single Cell 3' Reagent Kits User Guide with Feature Barcoding Technology for Cell Surface Protein. 2018.
10X Genomics, Inc. CG000208 Rev E. Chromium Next GEM Single Cell V(D)J reagent Kits v1.1 User Guide with Feature Barcode Technology for Cell Surface Protein. 2020.
10X Genomics, Inc. CG000209 Rev D. Chromium Next GEM Single Cell ATAC Reagent Kits v1.1 User Guide. 2020.
10X Genomics, Inc. CG000239 Rev B. Visium Spatial Gene Expression Reagent Kits User Guide. 2020.
10X Genomics, Inc. CG00026. Chromium Single Cell 3' Reagent Kit User Guide. 2016.
10X Genomics, Inc. LIT00003 Rev B Chromium Genome Solution Application Note. 2017.
Abate, et al. Beating Poisson encapsulation statistics using close-packed ordering. Lab Chip. Sep. 21, 2009;9(18):2628-31. doi: 10.1039/b909386a. Epub Jul. 28, 2009.
Adamson et al., "Production of arrays of chemically distinct nanolitre plugs via repeated splitting in microfluidic devices", Lab Chip 6(9): 1178-1186 (Sep. 2006).
Agasti, et al. Photocleavable DNA barcode-antibody conjugates allow sensitive and multiplexed protein analysis in single cells. J Amer Chem Soc ePub, Nov. 2, 2012, vol. 134, No. 45, pp. 18499-18502.

(56) References Cited

OTHER PUBLICATIONS

Ahmed. Hydrogel: Preparation, characterization, and applications: A review. J. Adv. Res. 2015, 6: 105-121.
Aikawa, et al. Spherical Phospholipid Polymer Hydrogels for Cell Encapsulation Prepared with a Flow-Focusing Microfluidic Channel Device. Langmuir. Jan. 31, 2012;28(4):2145-50. doi: 10.1021/la2037586. Epub Dec. 22, 2011.
Allazetta, et al. Microfluidic Synthesis of Cell-Type-Specific Artificial Extracellular Matrix Hydrogels. Biomacromolecules. Apr. 8, 2013;14(4):1122-31. doi: 10.1021/bm4000162. Epub Mar. 8, 2013.
Amini, S. et al. "Haplotype-resolved whole-genome sequencing by contiguity-preserving transposition and combinatorial indexing" Nature Genetics (2014) 46:1343-1349 doi:10.1038/ng.3119.
Anna et al.: Formation of dispersions using "flow focusing" in microchannels: Applied Physics Letters, vol. 82, No. 3, pp. 364-366 (2003).
Baret, "Surfactants in droplet-based microfluidics" Lab Chip (12(3):422-433 (2012).
Bassett, et al. Competitive ligand exchange of crosslinking ions for ionotropic hydrogel formation. J. Mater. Chem. B, 2016,4, 6175-6182.
Beer et al. On-Chip, Real-Time, Single-Copy Polymerase Chain Reaction in Picoliter Droplets. Anal Chem 79:8471-8475 (2007).
Braeckmans et al., Scanning the Code. Modern Drug Discovery. 2003:28-32.
Brenner, et al. "In vitro cloning of complex mixtures of DNA on microbeads: physical separation of differentially expressed cDNAs." Proc Natl Acad Sci U S A. Feb. 15, 2000,97(4):1665-70.
Buchman GW, et al. Selective RNA amplification: a novel method using dUMP-containing primers and uracil DNA glycosylase. PCR Methods Appl. Aug. 1993; 3(1):28-31.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-15. Epub Aug. 9, 2001.
Calo, et al. Biomedical applications of hydrogels: A review of patents and commercial products. Eur. Polym. J., 2015, 65: 252-267.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Chien et al. "Multiport flow-control system for lab-on-a-chip microfluidic devices", Fresenius J. Anal Chem, 371:106-111 (Jul. 27, 2001).
Chu, et al. Controllable monodisperse multiple emulsions. Angew Chem Int Ed Engl. 2007;46(47):8970-4.
Clausell-Tormos et al., "Droplet-based microfluidic platforms for the encapsulation and screening of mammalian cells and multicellular organisms", Chem. Biol. 15:427-437 (2008).
Co-pending U.S. Appl. No. 16/434,076, inventor Giresi; Paul, filed Jun. 6, 2019.
Co-pending U.S. Appl. No. 16/434,084, inventor Giresi; Paul, filed Jun. 6, 2019.
Co-pending U.S. Appl. No. 16/434,102, inventors Price; Andrew D. et al., filed Jun. 6, 2019.
Co-pending U.S. Appl. No. 16/737,762, inventors Price; Andrew D. et al., filed Jan. 8, 2020.
Co-pending U.S. Appl. No. 16/737,770, inventors Belhocine; Zahara Kamila et al., filed Jan. 8, 2020.
Co-pending U.S. Appl. No. 16/789,273, inventors Maheshwari; Arundhati Shamoni et al., filed Feb. 12, 2020.
Co-pending U.S. Appl. No. 17/014,909, inventor Giresi; Paul, filed Sep. 8, 2020.
Co-pending U.S. Appl. No. 17/148,942, inventors McDermott; Geoffrey et al., filed Jan. 14, 2021.
Co-pending U.S. Appl. No. 17/166,982, inventors McDermott; Geoffrey et al., filed Feb. 3, 2021.
Co-pending U.S. Appl. No. 17/175,542, inventors Maheshwari; Arundhati Shamoni et al., filed Feb. 12, 2021.
Co-pending U.S. Appl. No. 17/220,303, inventor Walter; Dagmar, filed Apr. 1, 2021.
Co-pending U.S. Appl. No. 17/318,364, inventors Bava; Felice Alessio et al., filed May 12, 2021.
Co-pending U.S. Appl. No. 17/381,612, inventor Martinez; Luigi Jhon Alvarado, filed Jul. 21, 2021.
Co-pending U.S. Appl. No. 17/512,241, inventors Hill; Andrew John et al., filed Oct. 27, 2021.
Co-pending U.S. Appl. No. 17/517,408, inventors Salmanzadeh; Alireza et al., filed Nov. 2, 2021.
Co-pending U.S. Appl. No. 17/518,213, inventor Lund; Paul Eugene, filed Nov. 3, 2021.
Co-pending U.S. Appl. No. 17/522,741, inventors Zheng; Xinying et al., filed Nov. 9, 2021.
Co-pending U.S. Appl. No. 17/545,862, inventor Katherine; Pfeiffer, filed Dec. 8, 2021.
Co-pending U.S. Appl. No. 17/573,350, inventor Corey; M. Nemec, filed Jan. 11, 2022.
Co-pending U.S. Appl. No. 17/580,947, inventor Gibbons; Michael, filed Jan. 21, 2022.
Co-pending U.S. Appl. No. 18/046,843, inventor Toh; Mckenzi, filed Oct. 14, 2022.
Co-pending U.S. Appl. No. 18/152,650, inventor Shastry; Shankar, filed dated Jan. 10, 2023.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Drmanac et al., Sequencing by hybridization (SBH): advantages, achievements, and opportunities. Adv Biochem Eng Biotechnol. 2002;77 :75-101.
Duffy et al., Rapid Protyping of Microfluidic Systems and Polydimethylsiloxane, Anal Chem 70:4974-4984 (1998).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Esser-Kahn, et al. Triggered release from polymer capsules. Macromolecules. 2011; 44:5539-5553.
Farrukh, et al. Bioconjugating Thiols to Poly(acrylamide) Gels for Cell Culture Using Methylsulfonyl Co-monomers. Angew Chem Int Ed Engl. Feb. 5, 2016;55(6):2092-6. doi: 10.1002/anie.201509986. Epub Jan. 6, 2016.
Gericke, et al. Functional cellulose beads: preparation, characterization, and applications. Chemical reviews 113.7 (2013): 4812-4836.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
Henke, et al. Enzymatic Crosslinking of Polymer Conjugates is Superior over Ionic or UV Crosslinking for the On-Chip Production of Cell-Laden Microgels. Macromol Biosci. Oct. 2016;16(10):1524-1532. doi: 10.1002/mabi.201600174. Epub Jul. 21, 2016.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Hug, et al. Measurement of the number of molecules of a single mRNA species in a complex mRNA preparation. J Theor Biol. Apr. 21, 2003;221(4):615-24.
Huynh, Ngoc-Thach, et al., "Preparation and swelling properties of "click" hydrogel from polyaspartamide derivatives using tri-arm PEG and PEG-co-poly (amino urethane) azides as crosslinking agents", Polymer, vol. 54, No. 4, Jan. 10, 2013, pp. 1341-1349.
Islam, et al. Highly multiplexed and strand-specific single-cell RNA 5' end sequencing. Nat Protoc. Apr. 5, 2012;7(5):813-28. doi: 10.1038/nprot.2012.022.

(56) References Cited

OTHER PUBLICATIONS

Jaitin, et al. Massively parallel single-cell RNA-seq for marker-free decomposition of tissues into cell types. Science. Feb. 14, 2014;343(6172):776-9. doi: 10.1126/science.1247651.
Jarosz, M. et al. "Using 1ng of DNA to detect haplotype phasing and gene fusions from whole exome sequencing of cancer cell lines" Cancer Res (2015) 75(supp15):4742.
Jiang et al. Cell-laden microfluidic microgels for tissue regeneration. Lab Chip 16(23):4482- 4506 (Nov. 2016).
Jiang, Yanjiao, et al., "Click hydrogels, microgels and nanogels: Emerging platforms for drug delivery and tissue engineering", Biomaterials, vol. 35, No. 18, Jun. 1, 2014, pp. 4969-4985.
Kamperman, et al. Centering Single Cells in Microgels via Delayed Crosslinking Supports Long-Term 3D Culture by Preventing Cell Escape. Small. Jun. 2017;13(22). doi: 10.1002/smll.201603711. Epub Apr. 28, 2017.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Kenis, et al. Microfabrication Inside Capillaries Using Multiphase Laminar Flow Patterning. Science. 1999; 285:83-85.
Kivioja, et al. Counting absolute numbers of molecules using unique molecular identifiers. Nat Methods. Nov. 20, 2011;9(1):72-4.
Klein, et al. Droplet barcoding for single-cell transcriptomics applied to embryonic stem cells. Cell. May 21, 2015;161(5):1187-201. doi: 10.1016/j.cell.2015.04.044.
Klein, et al. Droplet barcoding for single-cell transcriptomics applied to embryonic stem cells. Cell. May 21, 2015; 161:1187-1201.
Kolb HC, Finn MG, B. SK. 2001. "Click Chemistry: Diverse Chemical Function from a Few Good Reactions" Angew.Chem. Int. 40: 2004-21.
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chem. 8: 1110-1115 (2008).
Kukwikila, et al. Assembly of a biocompatible triazole-linked gene by one-pot click-DNA ligation. Nature Chemistry (2017) doi:10.1038/nchem.2850.
Lagally, et al. Single-Molecular DNA Amplification and Analysis in an Integrated Microfluidic Device. Anal Chem. Feb. 1, 2001;73(3):565-70.
Lennon et al. A scalable, fully automated process for construction of sequence-ready barcoded libraries for 454. Genome Biology 11:R15 (2010).
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Madl, et al. "Bioorthogonal Strategies for Engineering Extracellular matrices", Madal, Christopher, Adv. Funct. Master. Jan. 19, 2018, vol. 28, 1706046, pp. 1-21.
Mair, et al. Injection molded microfluidic chips featuring integrated interconnects. Lab Chip. Oct. 2006;6(10):1346-54. Epub Jul. 31, 2006.
Marquis, et al. Microfluidics-assisted diffusion self-assembly: toward the control of the shape and size of pectin hydrogel microparticles. Biomacromolecules. May 12, 2014;15(5):1568-78. doi: 10.1021/bm401596m. Epub Apr. 8, 2014.
McCoy, R. et al. "Illumina TruSeq Synthetic Long-Reads Empower De Novo Assembly and Resolve Complex, Highly-Repetitive Transposable Elements" PLOS (2014) 9(9):e1016689.
Microfluidic ChipShop. Microfluidic product catalogue. Oct. 2009.
Navin. The first five years of single-cell cancer genomics and beyond. Genome Res. Oct. 2015;25(10):1499-507. doi: 10.1101/gr.191098.115.
Nimmo, Chelsea M., et al., "Regenerative Biomaterials that "Click": Simple, Aqueous-Based Protocols for Hydrogel Synthesis, Surface Immobilization, and 3D Patterning", Bioconjugate Chemistry, vol. 22, No. 11, Nov. 16, 2011, pp. 2199-2209.
Nisisako, et al. Droplet formation in a microchannel network. Lab Chip. Feb. 2002;2(1):24-6. Epub Jan. 18, 2002.
Nisisako, T. et al. Droplet Formation in a Microchannel on PMMA Plate. Micro Total Analysis Systems. 2001. Kluwer Academic Publishers. pp. 137-138.
Nisisako, T. et al., Microfluidics large-scale integration on a chip for mass production of monodisperse droplets and particles, The Royal Society of Chemistry: Lab Chip, (Nov. 23, 2007) 8:287-293.
Novak, et al. Single cell multiplex gene detection and sequencing using microfluidically generated agarose emulsions. Angew Chem Int Ed Engl. Jan. 10, 2011;50(2):390-5. doi: 10.1002/anie.201006089.
Orakdogen, N. "Novel responsive poly(N,N-dimethylaminoethyl methacrylate) gel beads: preparation, mechanical properties and pH-dependent swelling behavior" J Polym Res (2012) 19:9914.
Pelton, et al. (2011) Microgels and Their Synthesis: An Introduction, in Microgel Suspensions: Fundamentals and Applications (eds A. Fernandez-Nieves, H. M. Wyss, J. Mattsson and D. A. Weitz), Wiley-VCH Verlag GmbH & Co. KGaA, Weinheim, Germany. doi: 10.1002/9783527632992.ch1.
Perrott, Jimmy. Optimization and Improvement of Emulsion PCR for the Ion Torrent Next-Generation Sequencing Platform. (2011) Thesis.
Peters, B.A. et al. Accurate whole-genome sequencing and haplotyping from 10 to 20 human cells. Nature, 487(7406):190-195 (Jul. 11, 2012).
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Priest, et al. Generation of Monodisperse Gel Emulsions in a Microfluidic Device, Applied Physics Letters, 88:024106 (2006).
Pushkarev et al. "Single-molecule sequencing of an individual human genome," Nature Biotech (2009) 27:847-850.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-11. URL: http://454.com/downloads/my454/documentation/technical-bulletins/TCB-09004 Using MultiplexIdentifierAdaptorsForTheGSFLXTitaniumSeriesChemistry-BasicMIDSet.pdf.
Rotem, A. et al., "High-throughput single-cell labeling (Hi-SCL) for RNA-Seq using drop-based microfluidics" PLOS One (May 22, 2015) 0116328 (14 pages).
Rotem, et al. Single Cell Chip-Seq Using Drop-Based Microfluidics. Abstract #50. Frontiers of Single Cell Analysis, Stanford University Sep. 5-7, 2013.
Rotem, et al. Single-cell ChIP-seq reveals cell subpopulations defined by chromatin state. Nat Biotechnol. Nov. 2015;33(11):1165-72. doi: 10.1038/nbt.3383. Epub Oct. 12, 2015.
Sahiner. Single step poly(L-Lysine) microgel synthesis, characterization and biocompatibility tests. Polymer, vol. 121, Jul. 14, 2017, pp. 46-54.
Saikia, et al. Simultaneous multiplexed amplicon sequencing and transcriptome profiling in single cells. Nat Methods. Jan. 2019;16(1):59-62. doi: 10.1038/s41592-018-0259-9. Epub Dec. 17, 2018.
Schubert, et al. Microemulsifying fluorinated oils with mixtures of fluorinated and hydrogenated surfactants. Colloids and Surfaces A; Physicochemical and Engineering Aspects, 84(1994) 97-106.
Seiffert, et al. Microfluidic fabrication of smart microgels from macromolecular precursors. Polymer. vol. 51, Issue 25, Nov. 26, 2010, pp. 5883-5889.
Seiffert. Microgel capsules tailored by droplet-based microfluidics. Chemphyschem. Feb. 4, 2013;14(2):295-304. doi: 10.1002/cphc.201200749. Epub Dec. 6, 2012.

(56) References Cited

OTHER PUBLICATIONS

Seiffert, S. et al., "Smart microgel capsules from macromolecular precursors" J. Am. Chem. Soc. (2010) 132:6606-6609.
Shah, et al. "Fabrication of mono disperse thermosensitive microgels and gel capsules in micro fluidic devices", Soft Matter, 4:2303-2309 (2008).
Shelbourne et al., "Fast copper-free click DNA ligation by the ring-strain promoted alkyne-azide cycloaddition reaction," Chem. Commun., 2011, 47, 6257-6259.
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE. 1117839.
Shih, et al. Photoclick Hydrogels Prepared from Functionalized Cyclodextrin and Poly(ethylene glycol) for Drug Delivery and in Situ Cell Encapsulation. Biomacromolecules. Jul. 13, 2015;16(7):1915-23. doi: 10.1021/acs.biomac.5b00471. Epub Jun. 3, 2015.
Singh, Maya Shankar, et al., "Advances of azide-alkyne ccloaddition-click chemistry over the recent decade", Tetrahedron, Elsevier Science Publishers, Amsterdam, NL, vol. 72, No. 35, Jul. 14, 2016, pp. 5257-5283.
Smith, et al. Highly-multiplexed barcode sequencing: an efficient method for parallel analysis of pooled samples. Nucleic Acids Research, 38(13): e142 (2010).
Song, et al. Reactions in droplets in microfluidic channels. Angew Chem Int Ed Engl. Nov. 13, 2006;45(44):7336-56.
Spitale et al., "Structural imprints in vivo decode RNA regulatory mechanisms," Nature. Mar. 26, 2015;519(7544):486-90; doi: 10.1038/nature14263. Epub Mar. 18, 2015.
Tam, et al. Engineering Cellular Microenvironments with Photo- and Enzymatically Responsive Hydrogels: Toward Biomimetic 3D Cell Culture Models. Acc Chem Res. Apr. 18, 2017;50(4):703-713. doi: 10.1021/acs.accounts.6b00543. Epub Mar. 27, 2017.
Thaxton, C.S. et al. "A Bio-Bar-Code Assay Based Upon Dithiothreitol Oligonucleotide Release" Anal Chem (2005) 77:8174-8178.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thorsen, et al. Dynamic pattern formation in a vesicle-generating microfluidic device. Physical Review Letters. American Physical Society. 2001; 86(18):4163-4166.
Tonelli, et al. Perfluoropolyether functional oligomers: unusual reactivity in organic chemistry. Journal of fluorine chemistry. 2002; 118(1) 107-121.
Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.
Uttamapinant, et al. Fast, cell-compatible click chemistry with copper-chelating azides for biomolecular labeling. Angew. Chem. Int. End. Engl., Jun. 11, 2012: 51(24) pp. 5852-5856.
Velasco, et al. Microfluidic encapsulation of cells in polymer microgels. Small. Jun. 11, 2012;8(11):1633-42. doi: 10.1002/smll. 201102464. Epub Mar. 29, 2012.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Weigl, et al. Microfluidic Diffusion-Based Separation and Detection. Science. 1999; pp. 346-347.
Williams, et al. Amplification of complex gene libraries by emulsion PCR. Nature Methods. 2006;3(7):545-50.
Zhang, et al. One-step fabrication of supramolecular microcapsules from microfluidic droplets. Science. Feb. 10, 2012;335(6069):690-4. doi: 10.1126/science.1215416.
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhu et al. Hydrogel Droplet Microfluidics for High-Throughput Single Molecule/Cell Analysis. Accounts of Chemical Research Article ASAP. DOI: 10.1021/acs.accounts.6b00370.
Zhu, et al. Reverse transcriptase template switching: a SMART approach for full-length cDNA library construction. Biotechniques. Apr. 2001;30(4):892-7.

\* cited by examiner

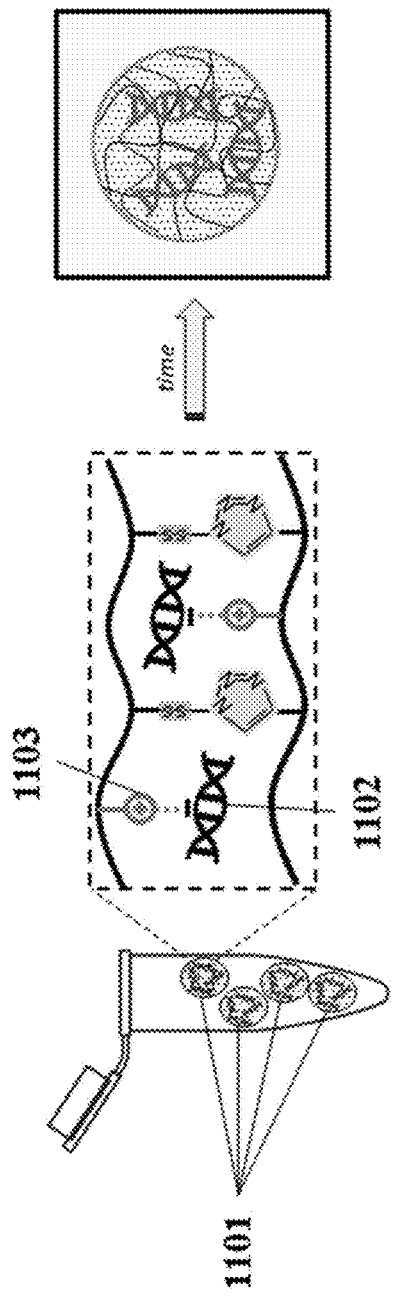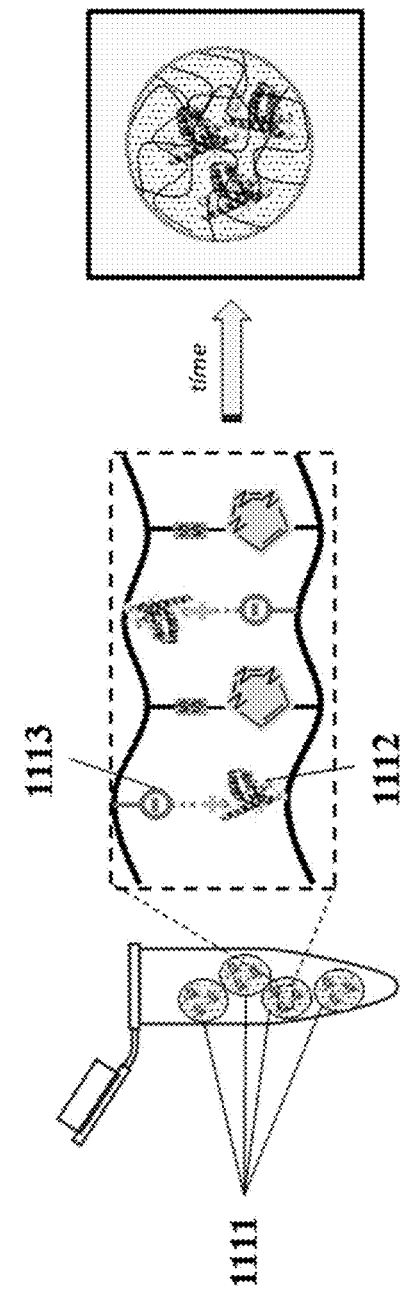

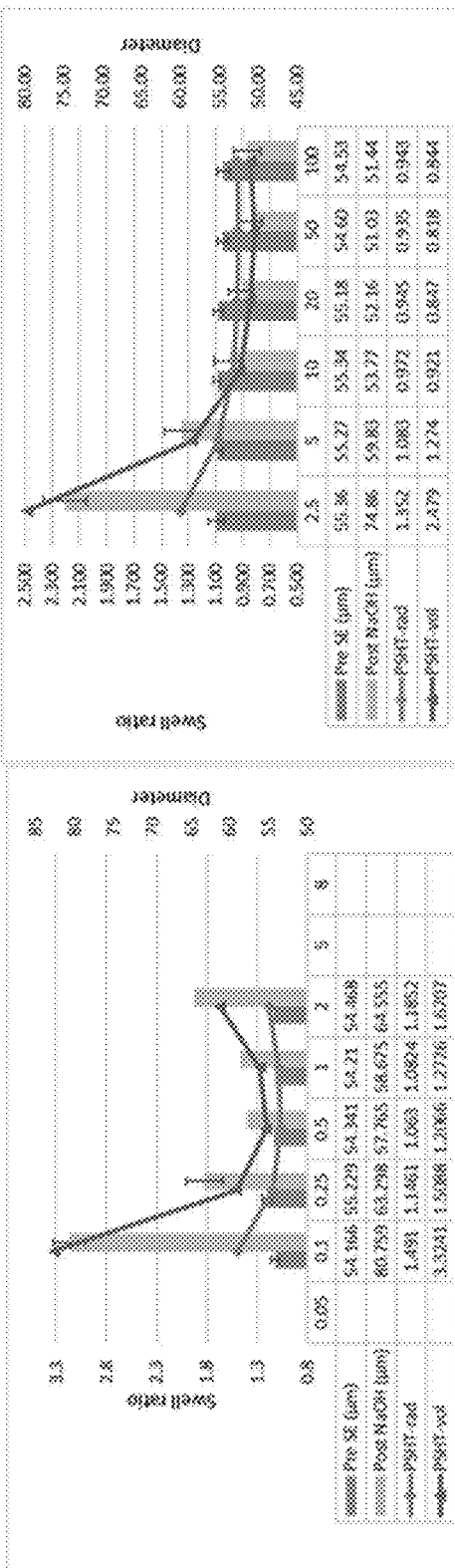
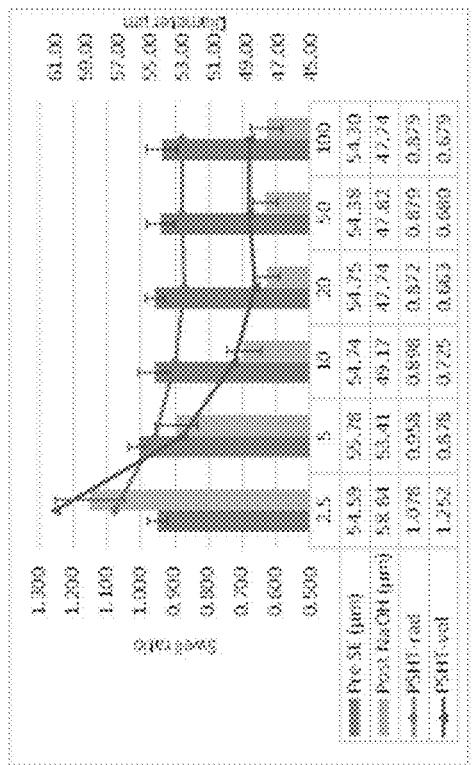
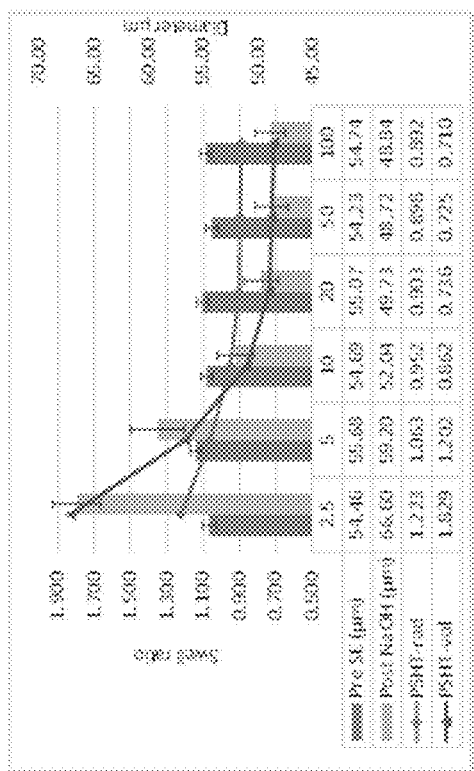
FIG. 27A  FIG. 27B  FIG. 27C  FIG. 27D

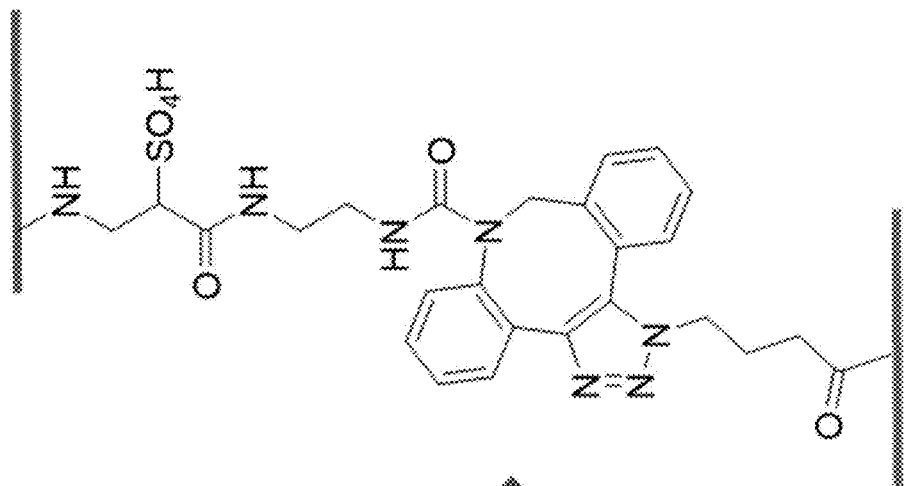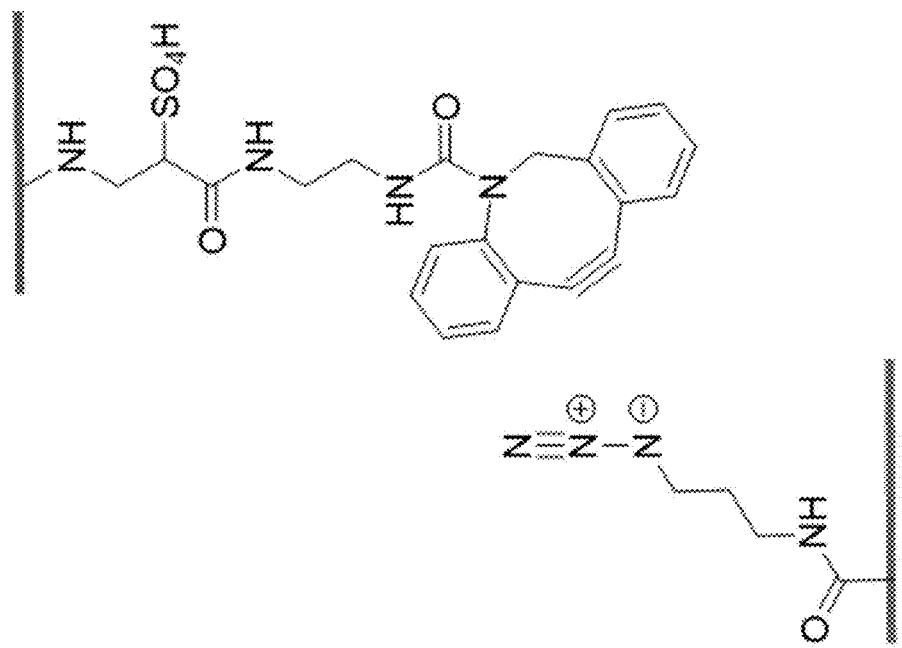
FIG. 30

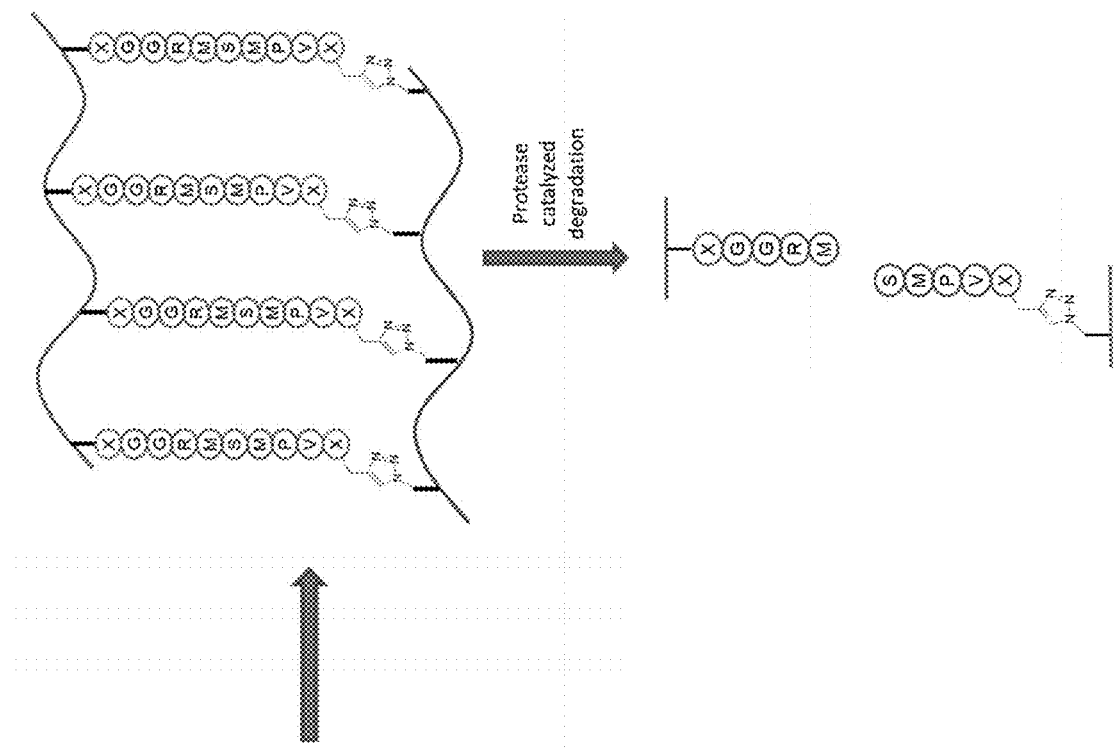
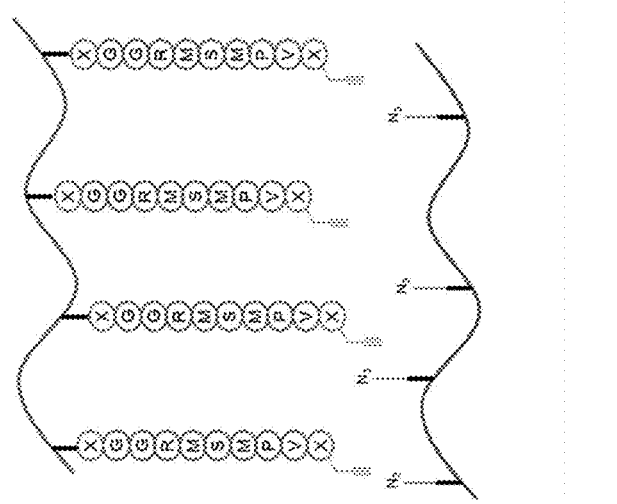
FIG. 34B

COMPOSITIONS, METHODS, AND SYSTEMS FOR BEAD FORMATION USING IMPROVED POLYMERS

CROSS-REFERENCE

This application is a continuation of U.S. patent application Ser. No. 17/009,352, filed Sep. 1, 2020, now issued as U.S. Pat. No. 11,441,172, which is a continuation of U.S. patent application Ser. No. 16/374,112, filed Apr. 3, 2019, now issued as U.S. Pat. No. 10,837,047, which is a continuation-in-part of U.S. patent application Ser. No. 16/178,430, filed Nov. 1, 2018, now issued as U.S. Pat. No. 10,590,244, which is a continuation of International Pat. Appl. No. PCT/US2018/054458, filed Oct. 4, 2018, which claims priority to U.S. Provisional Patent Application No. 62/687,161, filed Jun. 19, 2018, and U.S. Provisional Pat. Appl. No. 62/568,021, filed Oct. 4, 2017, each of which is incorporated by reference herein in its entirety for all purposes.

BACKGROUND

Samples may be processed for various purposes, such as identification of a type of sample of moiety within the sample. The sample may be a biological sample. The biological samples may be processed for various purposes, such as detection of a disease (e.g., cancer) or identification of a particular species. There are various approaches for processing samples, such as polymerase chain reaction (PCR) and sequencing.

Biological samples may be processed within various reaction environments, such as partitions. Partitions may be wells or droplets. Droplets or wells may be employed to process biological samples in a manner that enables the biological samples to be partitioned and processed separately. For example, such droplets may be fluidically isolated from other droplets, enabling accurate control of respective environments in the droplets.

Biological samples in partitions may be subjected to various processes, such as chemical processes or physical processes. Samples in partitions may be subjected to heating or cooling, or chemical reactions, such as to yield species that may be qualitatively or quantitatively processed.

SUMMARY

A hydrogel matrix (including a bead) can create a semi-open system capable of enclosing a large molecule within the boundary of the matrix, while allowing a small molecule to permeate the matrix. The large molecule can be a biological sample, including, for example, a cell, a large protein or a long nucleic acid. The small molecule can be, such as, for example, a reagent, a smaller protein, or a shorter nucleic acid. An enzyme, for example, may be small enough to permeate the matrix. The hydrogel matrix can also comprise a labile bond such that after the hydrogel matrix is degraded, the enclosed large molecule can be released from the confine of the matrix into the surrounding environment. Provided herein are methods, systems and compositions for the production of a hydrogel matrix capable of enclosing a large molecule and allowing a small molecule to permeate the matrix.

In some aspects, the present disclosure provides a gel, comprising: (a) a cell, a cell nucleus, or one or more constituents derived from a cell; (b) two or more polymers; and (c) a plurality of linkers, each of said plurality of linkers comprising a 1,2,3-triazole moiety, wherein said linkers crosslink said two or more polymers. In some embodiments, each of said two or more polymers independently comprises at least one selected from the group consisting of a polyolefin, an olefin copolymer, an acrylic, a vinyl polymer, a polyester, a polycarbonate, a polyamide, a polyimide, a formaldehyde resin, a polyurethane, an ether polymer, a cellulosic, a thermoplastic elastomer, and a thermoplastic polyurethane. In some embodiments, each of said two or more polymers is, independently, a polyacrylamide. In some embodiments, each of said plurality of linkers is independently connected to an amide of said two or more polymers. In some embodiments, each of said plurality of linkers comprise a labile bond. In some embodiments, said labile bond is a chemically labile bond, a thermally labile bond, or a photo-labile bond. In some embodiments, said labile bond comprises a disulfide bond. In some embodiments, said 1,2,3-triazole moiety is formed by a process of treating an azide group with an alkyne group in conditions sufficient for forming said 1,2,3-triazole moiety. In some embodiments, the gel further comprises at least one reagent enclosed within said gel.

In some embodiments, said gel is a hydrogel. In some embodiments, said gel further comprises a charged species. In some embodiments, said charged species is positively charged. In some embodiments, said charged species comprises trimethylammonium. In some embodiments, said charged species is negatively charged. In some embodiments, said charged species comprises phosphate. In some embodiments, said charged species is attached to said polymer or gel network. In some embodiments, at least one of said two or more polymers is an electrically charged polymer. In some embodiments, said electrically charged polymer is a positively charged polymer. In some embodiments, said positively charged polymer comprises chitosan or polyethyleneimine. In some embodiments, said electrically charged polymer is a negatively charged polymer. In some embodiments, said a negatively charged polymer comprises alginate. In some embodiments, at least one of said two or more polymers comprises an electrically charged moiety, and wherein said electrically charged moiety is connected to said at least one of said two or more polymers by a linker. In some embodiments, said linker comprises a labile bond capable of cleaving said electrically charged moiety from said at least one of said two or more polymers. In some embodiments, said labile bond is a chemically labile bond, a thermally labile bond, or a photo-labile bond.

In some aspects, the present disclosure provides a method of forming a gel comprising a cell or a cell nucleus, comprising: (a) providing (i) a first polymer, wherein said first polymer comprises a plurality of first crosslink precursors, each of said plurality of first crosslink precursors comprising an azide group; (ii) a second polymer, wherein said second polymer comprises a plurality of second crosslink precursors, each of said plurality of second crosslink precursors comprising an alkyne group; and (iii) said cell or said cell nucleus; (b) crosslinking said first polymer and said second polymer via a reaction between a first section of said first crosslink precursors and a second section of said second crosslink precursors, thereby forming said gel comprising said cell or said cell nucleus. In some embodiments, said first polymer and said second polymer independently comprise at least one selected from the group consisting of a polyolefin, an olefin copolymer, an acrylic, a vinyl polymer, a polyester, a polycarbonate, a polyamide, a polyimide, a formaldehyde resin, a polyurethane, an ether polymer, a cellulosic, a thermoplastic elastomer, and a thermoplastic polyurethane.

In some embodiments, said first polymer or said second polymer further comprise a labile bond. In some embodiments, said first polymer and said second polymer further comprise a labile bond. In some embodiments, said labile bond is a disulfide bond. In some embodiments, at least about 80% of said labile bond remains intact during said reaction in (b). In some embodiments, said reaction forms a 1,2,3-triazole between said azide and said alkyne. In some embodiments, the method further comprises prior to (b), providing a catalyst configured to catalyze said reaction in (b). In some embodiments, the method further comprises subsequent to (b), removing said catalyst and/or a derivative thereof from said gel. In some embodiments, said gel is formed from a plurality of said first polymers and a plurality of said second polymers. In some embodiments, said gel is a hydrogel.

In some embodiments, the method further comprises subsequent to (b), lysing said cell or said cell nucleus to release one or more cell or cell nucleus constituents into said gel. In some embodiments, said one or more cell or cell nucleus constituents comprises a nucleic acid. In some embodiments, said nucleic acid comprises a ribonucleic acid. In some embodiments, said ribonucleic acid is a messenger ribonucleic acid (mRNA). In some embodiments, said ribonucleic acid is a micro ribonucleic acid (miRNA). In some embodiments, said nucleic acid comprises a deoxyribonucleic acid (DNA). In some embodiments, said DNA is genomic DNA. In some embodiments, said one or more cell or cell nucleus constituents comprises chromatin. In some embodiments, said one or more cell or cell nucleus constituents comprises a protein. In some embodiments, said one or more cell or cell nucleus constituents is capable of being retained within said gel. In some embodiments, said one or more cell or cell nucleus constituents is capable of being retained within said gel for at least 1, at least 2, at least 3, at least 4, at least 5, at least 12, or at least 24 hours. In some embodiments, the method further comprises denaturing said DNA. In some embodiments, said denaturing comprises contacting said gel with a chemical reagent. In some embodiments, said chemical reagent is an alkaline reagent. In some embodiments, the method further comprises subsequent to (b), permeabilizing said cell or said cell nucleus. In some embodiments, the method further comprises prior to (b), co-partitioning said first polymer, said second polymer, and said cell or cell nucleus into a partition. In some embodiments, said partition is a well. In some embodiments, said partition is an aqueous droplet in an emulsion. In some embodiments, said partition comprises a reagent configured to catalyze said reaction in (b). In some embodiments, said emulsion comprises an oil phase comprising a reagent comprising a copper (II) moiety, and wherein said aqueous droplet comprises a reducing agent capable of reducing said copper (II) moiety to a copper (I) moiety, wherein said copper (I) moiety catalyzes said reaction in (b). In some embodiments, said emulsion comprises a reagent that facilitates the transport of said copper (II) moiety from said oil phase into said aqueous droplet. In some embodiments, the method further comprises prior to (b), lysing or permeabilizing said cell or cell nucleus in said partition.

In some aspects, the present disclosure provides a method for generating a cell bead, comprising: (a) generating a partition comprising a cell from a plurality of cells or a nucleus from a plurality of nuclei, a polymeric or gel precursor, and a charged species; and (b) subjecting said partition to conditions sufficient to react said polymeric or gel precursor to generate a polymer or gel network comprising (i) said cell or a derivative thereof, and (ii) said charged species, thereby providing said cell bead. In some embodiments, said partition is among a plurality of partitions. In some embodiments, the method further comprises generating a plurality of cell beads from said plurality of partitions. In some embodiments, said charged species is positively charged. In some embodiments, said charged species comprises trimethylammonium. In some embodiments, said charged species is (3-acrylamidopropyl)trimethylammonium. In some embodiments, said charged species is negatively charged. In some embodiments, said charged species comprises phosphate. In some embodiments, said charged species is attached to said polymer or gel network. In some embodiments, said cell bead comprises a plurality of chemical cross-linkers. In some embodiments, said charged species is attached to a chemical-cross linker of said chemical cross-linkers. In some embodiments, the method further comprises prior to (b), subjecting said cell bead to conditions sufficient to lyse said cell or cell nucleus to release one or more cell or cell nucleus constituents into said cell bead.

In some embodiments, the method further comprises subsequent to (b), subjecting said cell bead to conditions sufficient to lyse said cell or cell nucleus to release one or more cell or cell nucleus constituents into said cell bead. In some embodiments, said one or more cell or cell nucleus constituents comprises a nucleic acid. In some embodiments, said nucleic acid comprises ribonucleic acid. In some embodiments, said ribonucleic acid is a messenger ribonucleic acid. In some embodiments, said nucleic acid comprises a deoxyribonucleic acid. In some embodiments, said one or more cell or cell nucleus constituents comprises a protein. In some embodiments, said one or more cell or cell nucleus constituents is capable of being retained within said cell bead. In some embodiments, said one or more cell or cell nucleus constituents is capable of being retained within said cell bead for at least 1, at least 2, at least 3, at least 4, at least 5, at least 12, or at least 24 hours.

In some aspects, the present disclosure provides a method for generating a cell bead, comprising: (a) generating a partition comprising (i) a cell from a plurality of cells or a nucleus from a plurality of nuclei and (ii) an electrically charged polymeric or gel precursor; and (b) subjecting said partition to conditions sufficient to react said polymeric or gel precursor to generate an electrically charged polymer or gel network comprising said cell or said nucleus or a derivative thereof, thereby providing said cell bead. In some embodiments, said electrically charged polymeric or gel precursor comprises a positive charge. In some embodiments, said electrically charged polymeric or gel precursor comprises chitosan. In some embodiments, said electrically charged polymeric or gel precursor comprises polyethyleneimine. In some embodiments, said electrically charged polymeric or gel precursor comprises a negative charge. In some embodiments, said electrically charged polymeric or gel precursor comprises alginate. In some embodiments, the method further comprises prior to (b), subjecting said cell bead to conditions sufficient to lyse said cell or cell nucleus to release one or more cell or cell nucleus constituents into said cell bead. In some embodiments, the method further comprises subsequent to (b), subjecting said cell bead to conditions sufficient to lyse said or cell nucleus to release one or more cell or cell nucleus constituents into said cell bead. In some embodiments, said one or more cell or cell nucleus constituents a nucleic acid. In some embodiments, said nucleic acid comprises a ribonucleic acid. In some embodiments, said ribonucleic acid is a messenger ribonucleic acid. In some embodiments, said nucleic acid comprises a deoxyribonucleic acid. In some embodiments, said one or more cell or cell nucleus constituents comprises a protein. In some embodiments, said one or more cell or cell nucleus constituents is capable of being retained within said cell bead. In some embodiments, said one or more cell or cell nucleus constituents is capable of being retained within said cell bead for at least 1, at least 2, at least 3, at least 4, at least 5, at least 12, or at least 24 hours.

In some aspects, the present disclosure provides a composition for use in analyzing one or more components from a cell, comprising a cell bead comprising a polymerized or cross-linked polymer network comprising a cell, a cell nucleus, or one or more constituents derived from a cell or a cell nucleus, wherein said polymerized or cross-linked polymer network is electrically charged. In some embodiments, said polymer network is positively charged. In some embodiments, said polymer network comprises polyethyleneimine. In some embodiments, said polymer network comprises chitosan. In some embodiments, said polymer network is negatively charged. In some embodiments, said polymer network comprises alginate.

In some aspects, the present disclosure provides a composition for use in analyzing one or more components from a cell, comprising a cell bead comprising a polymerized or cross-linked polymer network comprising (i) a cell, a cell nucleus, or one or more constituents derived from a cell or a cell nucleus; and (ii) a charged species. In some embodiments, said polymer network comprises a chemical cross-linker. In some embodiments, said cell bead comprises a component from said cell attached to said chemical cross-linker. In some embodiments, said charged species is attached to said polymer network. In some embodiments, said charged species is covalently attached to said polymer network. In some embodiments, said charges species is attached to a component from said cell. In some embodiments, said charged species is non-covalently attached to said component from said cell. In some embodiments, said charged species is positively charged. In some embodiments, said charged species comprises trimethylammonium. In some embodiments, said charged species is (2-Aminoethyl)trimethylammonium. In some embodiments, said charged species is (3-Acrylamidopropyl)trimethylammonium. In some embodiments, said charged species is negatively charged. In some embodiments, said charged species comprises phosphate.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIGS. 11A-B show an example charged hydrogel polymer network. FIG. 11A shows a schematic of a cell bead comprising positively charged species attached to a polymer network. FIG. 11B shows a schematic of a cell bead comprising negatively charged species attached to a polymer network.

FIG. 12A shows a schematic of a cell bead comprising positively charges species attached to disulfide containing chemical cross-linkers. FIG. 12B shows a schematic of a cell bead comprising negatively charges species attached to disulfide containing chemical cross-linkers.

FIG. 27A shows the results from a cell bead generation experiment described in Example 8 comprising the use of varying THPTA concentrations. FIG. 27B shows the results from a cell bead generation experiment described in Example 8 comprising the use of varying sodium ascorbate concentrations. FIG. 27C shows the results from a cell bead generation experiment described in Example 8 comprising the use of varying sodium ascorbate concentrations. FIG. 27D shows the results from a cell bead generation experiment described in Example 8 comprising the use of varying sodium ascorbate concentrations.

FIG. 30 shows an exemplary copper-free click chemistry crosslinking reaction using azide-modified and DBCO-modified linkers.

FIG. 34B shows formation of an exemplary protease cleavable polypeptide crosslink via click chemistry and subsequent selective protease catalyzed degradation of the crosslink.

DETAILED DESCRIPTION

Figure 1:
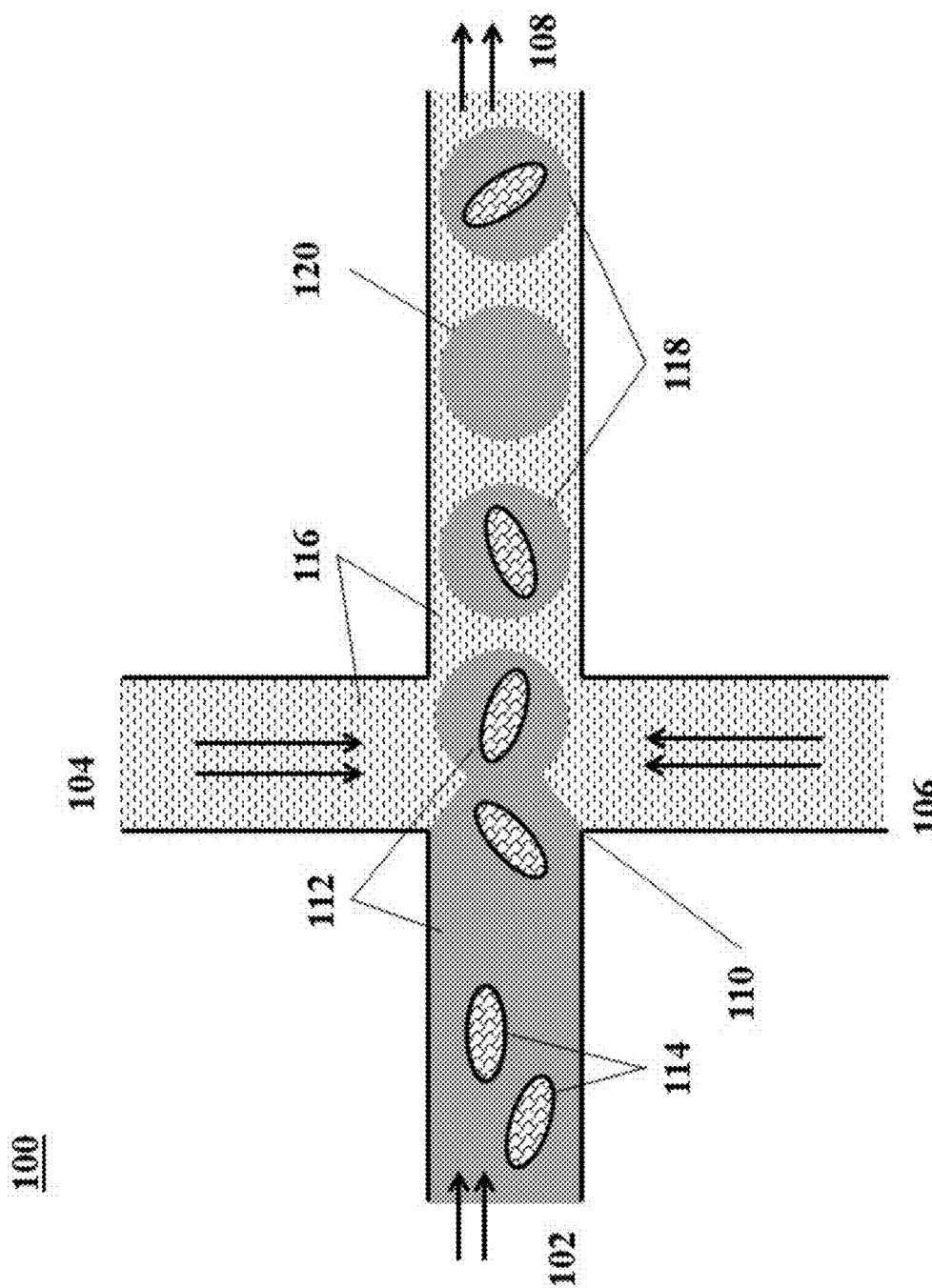
FIG. 1 shows an example of a microfluidic channel structure for partitioning individual biological particles.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads in real time.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human) or avian (e.g., bird), or other organism, such as a plant. The subject can be a vertebrate, a mammal, a rodent (e.g., a mouse), a primate, a simian or a human Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient.

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PACBIO®), OXFORD NANOPORE®, or Life Technologies (ION TORRENT®). Alternatively, or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or crosslinking) The bead may be formed of a polymeric material. The bead may be magnetic or non-magnetic. The bead may be rigid. The bead may be flexible and/or compressible. The bead may be disruptable or dissolvable.

The term "sample," as used herein, generally refers to a biological sample of a subject. The biological sample may comprise any number of macromolecules, for example, cellular macromolecules. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle," as used herein, generally refers to a discrete biological system derived from a biological sample. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell but may not include other constituents of the cell. An example of such constituents is a nucleus or an organelle. A cell may be a live cell. The live cell may be capable of being cultured, for example, being cultured when enclosed in a gel or polymer matrix or cultured when comprising a gel or polymer matrix.

The term "macromolecular constituent," as used herein, generally refers to a macromolecule contained within a biological particle. The macromolecular constituent may comprise a nucleic acid. The macromolecular constituent may comprise DNA. The macromolecular constituent may comprise RNA. The RNA may be messenger RNA (mRNA), ribosomal RNA (rRNA) or transfer RNA (tRNA). The RNA may be a transcript. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

Provided herein are compositions and methods for forming hydrogel matrices (including beads) by emulsion gelation. In addition, the hydrogel matrices can enclose a large molecule such as a biological sample. The biological sample can be a cell, a large protein, or a long nucleic acid. The hydrogel matrices can comprise a cell or one or more components from a cell (e.g., a cell bead). The hydrogel matrices can allow a smaller molecule to permeate the matrices. The smaller molecule can be a reagent, a smaller protein, or a shorter nucleic acid. The smaller protein can be an enzyme. The hydrogel can be degradable.

In an aspect, the present disclosure provides a composition of a degradable hydrogel comprising two or more polymers, and a plurality of linkers configured to form crosslinks. Each of the plurality of linkers can comprise a labile bond and a 1,2,3-triazole moiety. The two or more polymers can be crosslinked by such linkers.

In an aspect, the present disclosure provides a method of forming a hydrogel. The method can comprise (a) providing a first polymer, wherein the first polymer comprises a plurality of first crosslink precursors; (b) providing a second polymer, wherein the second polymer comprises a plurality of second crosslink precursors; and (c) crosslinking the first polymer and the second polymer via a reaction between a first section of the first crosslink precursors and a second section of the second crosslink precursors, thereby forming the hydrogel.

In an aspect, the systems and methods described herein provide for the compartmentalization, depositing, or partitioning of macromolecular constituent contents of individual biological particles into discrete compartments or partitions (referred to interchangeably herein as partitions), where each partition maintains separation of its own contents from the contents of other partitions. The partition can be a droplet in an emulsion. A partition may comprise one or more other partitions.

A partition of the present disclosure may comprise biological particles and/or macromolecular constituents thereof. A partition may comprise one or more gel beads. A partition may comprise one or more cell beads. A partition may include a single gel bead, a single cell bead, or both a single cell bead and single gel bead. A cell bead can be a biological particle and/or one or more of its macromolecular constituents encased inside of a gel or polymer matrix, such as via polymerization of a droplet containing the biological particle and precursors capable of being polymerized or gelled. Unique identifiers, such as barcodes, may be injected into the droplets previous to, subsequent to, or concurrently with droplet generation, such as via a microcapsule (e.g., bead), as described further below. Microfluidic channel networks (e.g., on a chip) can be utilized to generate partitions as described herein. Alternative mechanisms may also be employed in the partitioning of individual biological particles, including porous membranes through which aqueous mixtures of cells are extruded into non-aqueous fluids.

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can comprise droplets of aqueous fluid within a non-aqueous continuous phase (e.g., oil phase). The partitions can comprise droplets of a first phase within a second phase, wherein the first and second phases are immiscible. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In the case of droplets in an emulsion, allocating individual biological particles to discrete partitions may in one non-limiting example be accomplished by introducing a flowing stream of biological particles in an aqueous fluid into a flowing stream of a non-aqueous fluid, such that droplets are generated at the junction of the two streams. By providing the aqueous stream at a certain concentration and/or flow rate of biological particles, the occupancy of the resulting partitions (e.g., number of biological particles per partition) can be controlled. Where single biological particle partitions are used, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, cell or cellular material). In some embodiments, the relative flow rates of the fluids can be selected such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual biological particles. The channel structure 100 can include channel segments 102, 104, 106 and 108 communicating at a channel junction 110. In operation, a first aqueous fluid 112 that includes suspended biological particles (or cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual biological particle 114 (such as droplets 118). A discrete droplet generated may include more than one individual biological particle 114 (not shown in FIG. 1). A discrete droplet may contain no biological particle 114 (such as droplet 120). Each discrete partition may maintain separation of its own contents (e.g., individual biological particle 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying biological particles, cell beads, and/or gel beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more biological particles 114, and (2) unoccupied droplets 120, not containing any biological particles 114. Occupied droplets 118 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 114) at the partitioning junction 110, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 2:
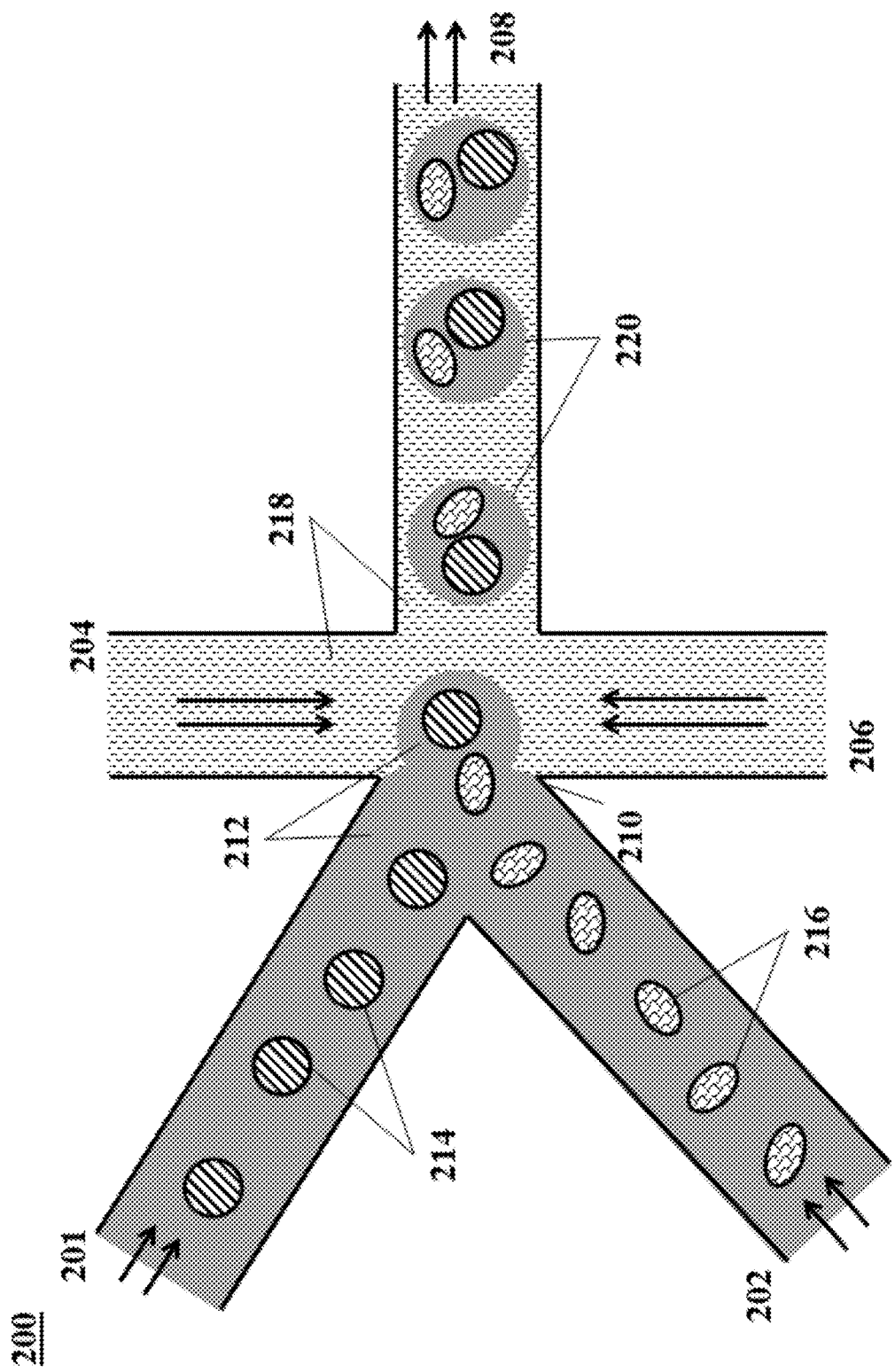
FIG. 2 shows an example of a microfluidic channel structure for delivering barcode carrying beads to droplets.

As will be appreciated, the above-described occupancy rates are also applicable to partitions that include both biological particles and additional reagents, including, but not limited to, microcapsules carrying barcoded nucleic acid molecules (e.g., oligonucleotides) (described in relation to FIG. 2). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and a biological particle.

In another aspect, in addition to or as an alternative to droplet based partitioning, biological particles may be encapsulated within a microcapsule that comprises an outer shell, layer or porous matrix in which is entrained one or more individual biological particles or small groups of biological particles. The microcapsule may include other reagents. Encapsulation of biological particles may be performed by a variety of processes. Such processes combine an aqueous fluid containing the biological particles with a polymeric precursor material that may be capable of being formed into a gel or other solid or semi-solid matrix upon application of a particular stimulus to the polymer precursor. Such stimuli can include, for example, thermal stimuli (either heating or cooling), photo-stimuli (e.g., through photo-curing), chemical stimuli (e.g., through crosslinking, polymerization initiation of the precursor (e.g., through added initiators), or the like, and/or a combination of the above.

Preparation of microcapsules comprising biological particles may be performed by a variety of methods. For example, air knife droplet or aerosol generators may be used to dispense droplets of precursor fluids into gelling solutions in order to form microcapsules that include individual biological particles or small groups of biological particles. Likewise, membrane based encapsulation systems may be used to generate microcapsules comprising encapsulated biological particles as described herein. Microfluidic systems of the present disclosure, such as that shown in FIG. 1, may be readily used in encapsulating cells as described herein. In particular, and with reference to FIG. 1, the aqueous fluid 112 comprising (i) the biological particles 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained biological particles. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams 116 in channel segments 104 and 106, which can initiate the copolymerization of the acrylamide and BAC into a cross-linked polymer network, or hydrogel.

Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., $Ca^{2+}$ ions), can be used as an encapsulation process using the described processes. Likewise, agarose droplets may also be transformed into capsules through temperature based gelling (e.g., upon cooling, etc.).

In some cases, encapsulated biological particles can be selectively releasable from the microcapsule, such as through passage of time or upon application of a particular stimulus, that degrades the microcapsule sufficiently to allow the biological particles (e.g., cell), or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The biological particle can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle may be surrounded by polyacrylamide strands linked together by disulfide bridges. In this manner, the biological particle may be encased inside of or comprise a gel or matrix (e.g., polymer matrix) to form a "cell bead." A cell bead can contain biological particles (e.g., a cell) or macromolecular constituents (e.g., RNA, DNA, proteins, etc.) of biological particles. A cell bead may include a single cell or multiple cells, or a derivative of the single cell or multiple cells. For example, after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles.

Encapsulated biological particles can provide certain potential advantages of being more storable and more portable than droplet-based partitioned biological particles. Furthermore, in some cases, it may be desirable to allow biological particles to incubate for a select period of time before analysis, such as in order to characterize changes in such biological particles over time, either in the presence or absence of different stimuli. In such cases, encapsulation may allow for longer incubation than partitioning in emulsion droplets, although in some cases, droplet partitioned biological particles may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the biological particles into which other reagents are co-partitioned. Alternatively, or in addition, encapsulated biological particles may be readily deposited into other partitions (e.g., droplets) as described above.

A partition may comprise one or more unique identifiers, such as barcodes. Barcodes may be previously, subsequently or concurrently delivered to the partitions that hold the compartmentalized or partitioned biological particle. For example, barcodes may be injected into droplets previous to, subsequent to, or concurrently with droplet generation. The delivery of the barcodes to a particular partition allows for the later attribution of the characteristics of the individual biological particle to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. In some cases, barcoded nucleic acid molecules can be initially associated with the microcapsule and then released from the microcapsule upon application of a stimulus which allows the nucleic acid molecules to dissociate or to be released from the microcapsule. A microcapsule, in some instances, can comprise a bead. Beads are described in further detail below.

FIG. 2 shows an example of a microfluidic channel structure 200 for delivering barcode carrying beads to droplets. The channel structure 200 can include channel segments 201, 202, 204, 206 and 208 communicating at a channel junction 210. In operation, the channel segment 201 may transport an aqueous fluid 212 that includes a plurality of beads 214 (e.g., with nucleic acid molecules, oligonucleotides, molecular tags) along the channel segment 201 into junction 210. The plurality of beads 214 may be sourced from a suspension of beads. For example, the channel segment 201 may be connected to a reservoir comprising an aqueous suspension of beads 214. The channel segment 202 may transport the aqueous fluid 212 that includes a plurality of biological particles 216 along the channel segment 202 into junction 210. The plurality of biological particles 216 may be sourced from a suspension of biological particles. For example, the channel segment 202 may be connected to a reservoir comprising an aqueous suspension of biological particles 216. In some instances, the aqueous fluid 212 in either the first channel segment 201 or the second channel segment 202, or in both segments, can include one or more reagents, as further described below. A second fluid 218 that is immiscible with the aqueous fluid 212 (e.g., oil) can be delivered to the junction 210 from each of channel segments 204 and 206. Upon meeting of the aqueous fluid 212 from each of channel segments 201 and 202 and the second fluid 218 from each of channel segments 204 and 206 at the channel junction 210, the aqueous fluid 212 can be partitioned as discrete droplets 220 in the second fluid 218 and flow away from the junction 210 along channel segment 208. The channel segment 208 may deliver the discrete droplets to an outlet reservoir fluidly coupled to the channel segment 208, where they may be harvested.

As an alternative, the channel segments 201 and 202 may meet at another junction upstream of the junction 210. At such junction, beads and biological particles may form a mixture that is directed along another channel to the junction 210 to yield droplets 220. The mixture may provide the beads and biological particles in an alternating fashion, such that, for example, a droplet comprises a single bead and a single biological particle.

Beads, biological particles and droplets may flow along channels at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 218 can comprise an oil, such as a fluorinated oil, that includes a fluorosurfactant for stabilizing the resulting droplets, for example, inhibiting subsequent coalescence of the resulting droplets 220.

A discrete droplet that is generated may include an individual biological particle 216. A discrete droplet that is generated may include a barcode or other reagent carrying bead 214. A discrete droplet generated may include both an individual biological particle and a barcode carrying bead, such as droplets 220. In some instances, a discrete droplet may include more than one individual biological particle or no biological particle. In some instances, a discrete droplet may include more than one bead or no bead. A discrete droplet may be unoccupied (e.g., no beads, no biological particles).

Beneficially, a discrete droplet partitioning a biological particle and a barcode carrying bead may effectively allow the attribution of the barcode to macromolecular constituents of the biological particle within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 200 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 1 micrometers ($\mu m$), 5 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 250 $\mu m$, 500 $\mu m$, 1 mm, or greater. In some cases, a bead may have a diameter of less than about 1 $\mu m$, 5 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 250 $\mu m$, 500 $\mu m$, 1 mm, or less. In some cases, a bead may have a diameter in the range of about 40-75 $\mu m$, 30-75 $\mu m$, 20-75 $\mu m$, 40-85 $\mu m$, 40-95 $\mu m$, 20-100 $\mu m$, 10-100 $\mu m$, 1-100 $\mu m$, 20-250 $\mu m$, or 20-500 $\mu m$.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds or thioether bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide), which may include a priming sequence (e.g., a primer for amplifying target nucleic acids, random primer, primer sequence for messenger RNA) and/or a one or more barcode sequences. The one more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, such as, for example, a P5 sequence for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence for attachment to a sequencing flow cell for Illumina sequencing. In some cases, the nucleic acid molecule can comprise a barcode sequence. In some cases, the primer can further comprise a unique molecular identifier (UMI). In some cases, the primer can comprise an R1 primer sequence for Illumina sequencing. In some cases, the primer can comprise an R2 primer sequence for Illumina sequencing. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)car-bodiimide (EDC) and N-Hydroxysuccinimide (NHS) or 4-(4,6-Dimethoxy-1,3,5-triazin-2-yl)-4-methylmorpho-linium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmaleimide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a carbamate linkage (e.g., cleavable with diethylenetriamine "DETA"), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNase)). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., NEXTERA® for ILLUMINA®). Such species may include one or more enzymes described herein, including without limitation, polymerase, reverse transcriptase, restriction enzymes (e.g., endonuclease), transposase, ligase, proteinase K, DNase, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively, or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken, and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken, and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc.) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades, and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

Although FIG. 1 and FIG. 2 have been described in terms of providing substantially singly occupied partitions, above, in certain cases, it may be desirable to provide multiply occupied partitions, e.g., containing two, three, four or more cells and/or microcapsules (e.g., beads) comprising barcoded nucleic acid molecules (e.g., oligonucleotides) within a single partition. Accordingly, as noted above, the flow characteristics of the biological particle and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction (e.g., junction 210). In such cases, the flow and frequency of the different beads into the channel or junction may be controlled to provide for a certain ratio of microcapsules from each source, while ensuring a given pairing or combination of such beads into a partition with a given number of biological particles (e.g., one biological particle and one bead per partition).

The partitions described herein may comprise small volumes, for example, less than about 10 microliters (µL), 5 µL, 1 µL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

In accordance with certain aspects, biological particles may be partitioned along with lysis reagents in order to release the contents of the biological particles within the partition. In such cases, the lysis agents can be contacted with the biological particle suspension concurrently with, or immediately prior to, the introduction of the biological particles into the partitioning junction/droplet generation zone (e.g., junction 210), such as through an additional channel or channels upstream of the channel junction. In accordance with other aspects, additionally or alternatively, biological particles may be partitioned along with other reagents, as will be described further below.

Figure 3:
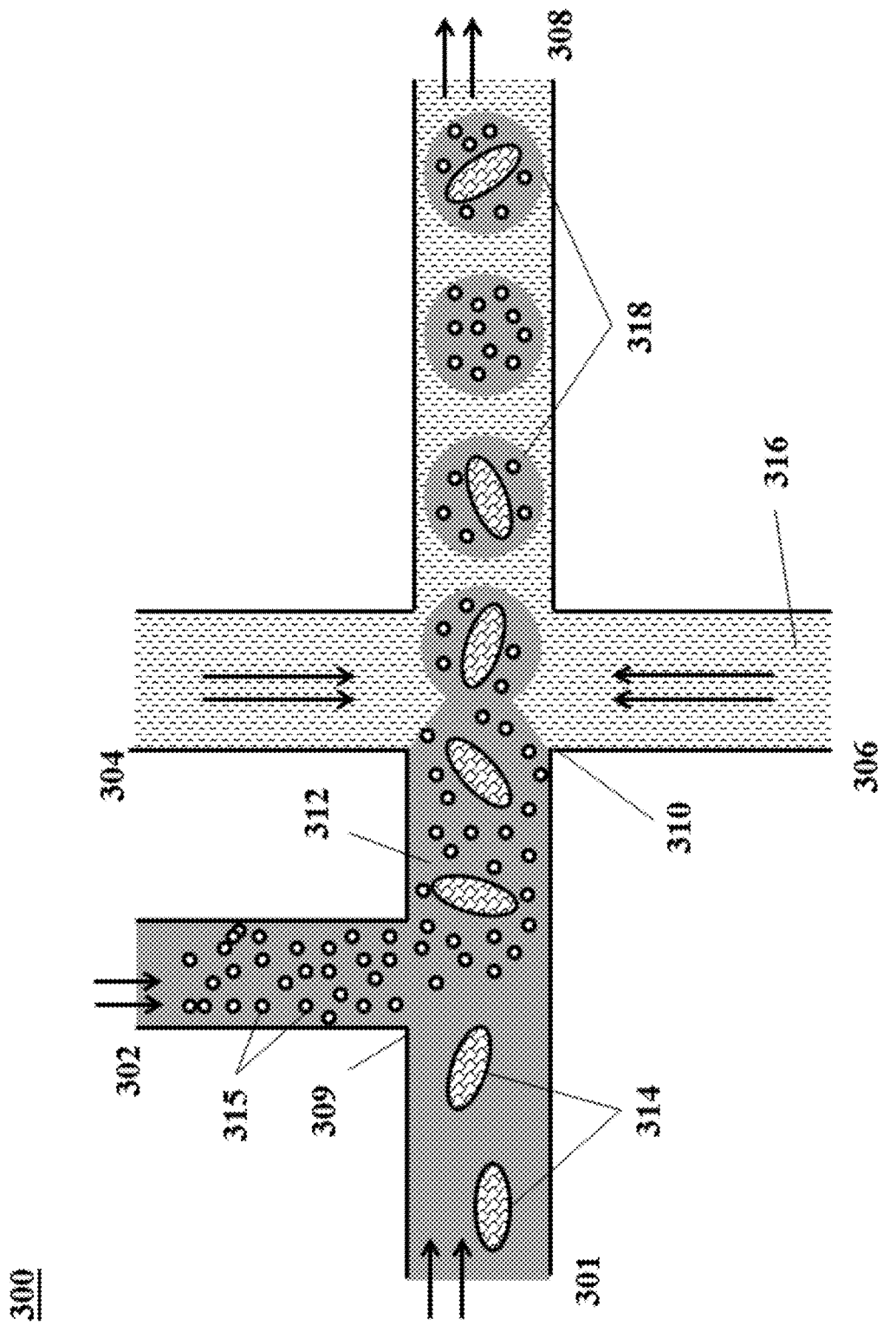
FIG. 3 shows an example of a microfluidic channel structure for co-partitioning biological particles and reagents.

FIG. 3 shows an example of a microfluidic channel structure 300 for co-partitioning biological particles and reagents. The channel structure 300 can include channel segments 301, 302, 304, 306 and 308. Channel segments 301 and 302 communicate at a first channel junction 309. Channel segments 302, 304, 306, and 308 communicate at a second channel junction 310.

In an example operation, the channel segment 301 may transport an aqueous fluid 312 that includes a plurality of biological particles 314 along the channel segment 301 into the second junction 310. As an alternative or in addition to, channel segment 301 may transport beads (e.g., gel beads). The beads may comprise barcode molecules.

For example, the channel segment 301 may be connected to a reservoir comprising an aqueous suspension of biological particles 314. Upstream of, and immediately prior to reaching, the second junction 310, the channel segment 301 may meet the channel segment 302 at the first junction 309. The channel segment 302 may transport a plurality of reagents 315 (e.g., lysis agents) suspended in the aqueous fluid 312 along the channel segment 302 into the first junction 309. For example, the channel segment 302 may be connected to a reservoir comprising the reagents 315. After the first junction 309, the aqueous fluid 312 in the channel segment 301 can carry both the biological particles 314 and the reagents 315 towards the second junction 310. In some instances, the aqueous fluid 312 in the channel segment 301 can include one or more reagents, which can be the same or different reagents as the reagents 315. A second fluid 316 that is immiscible with the aqueous fluid 312 (e.g., oil) can be delivered to the second junction 310 from each of channel segments 304 and 306. Upon meeting of the aqueous fluid 312 from the channel segment 301 and the second fluid 316 from each of channel segments 304 and 306 at the second channel junction 310, the aqueous fluid 312 can be partitioned as discrete droplets 318 in the second fluid 316 and flow away from the second junction 310 along channel segment 308. The channel segment 308 may deliver the discrete droplets 318 to an outlet reservoir fluidly coupled to the channel segment 308, where they may be harvested.

The second fluid 316 can comprise an oil, such as a fluorinated oil, that includes a fluorosurfactant for stabilizing the resulting droplets, for example, inhibiting subsequent coalescence of the resulting droplets 318.

A discrete droplet generated may include an individual biological particle 314 and/or one or more reagents 315. In some instances, a discrete droplet generated may include a barcode carrying bead (not shown), such as via other microfluidics structures described elsewhere herein. In some instances, a discrete droplet may be unoccupied (e.g., no reagents, no biological particles).

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 300 may have other geometries. For example, a microfluidic channel structure can have more than two channel junctions. For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, MO), as well as other commercially available lysis enzymes. Other lysis agents may additionally or alternatively be co-partitioned with the biological particles to cause the release of the biological particles' contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of biological particles that may be in addition to or in place of droplet partitioning, where any pore size of the encapsulate is sufficiently small to retain nucleic acid fragments of a given size, following cellular disruption.

In addition to the lysis agents co-partitioned with the biological particles described above, other reagents can also be co-partitioned with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles, the biological particles may be exposed to an appropriate stimulus to release the biological particles or their contents from a co-partitioned microcapsule. For example, in some cases, a chemical stimulus may be co-partitioned along with an encapsulated biological particle to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative aspects, this may be a different and non-overlapping stimulus, in order to allow an encapsulated biological particle to be released into a partition at a different time from the release of nucleic acid molecules into the same partition.

Additional reagents may also be co-partitioned with the biological particles, such as endonucleases to fragment a biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNase, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of biological particles, such as RNA, DNA, or proteins) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes can be assigned or associated with individual biological particles or populations of biological particle, in order to tag or label the biological particle's macromolecular components (and as a result, its characteristics) with the unique identifiers. These unique identifiers can then be used to attribute the biological particle's components and characteristics to an individual biological particle or group of biological particles.

In some aspects, this is performed by co-partitioning the individual biological particle or groups of biological particles with the unique identifiers, such as described above (with reference to FIG. 2). In some aspects, the unique identifiers are provided in the form of nucleic acid molecules (e.g., oligonucleotides) that comprise nucleic acid barcode sequences that may be attached to or otherwise associated with the nucleic acid contents of individual biological particle, or to other components of the biological particle, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned biological particles. These sequences include, e.g., targeted or random/universal amplification primer sequences for amplifying the genomic DNA from the individual biological particles within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems.

In an example, microcapsules, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules form the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 4:
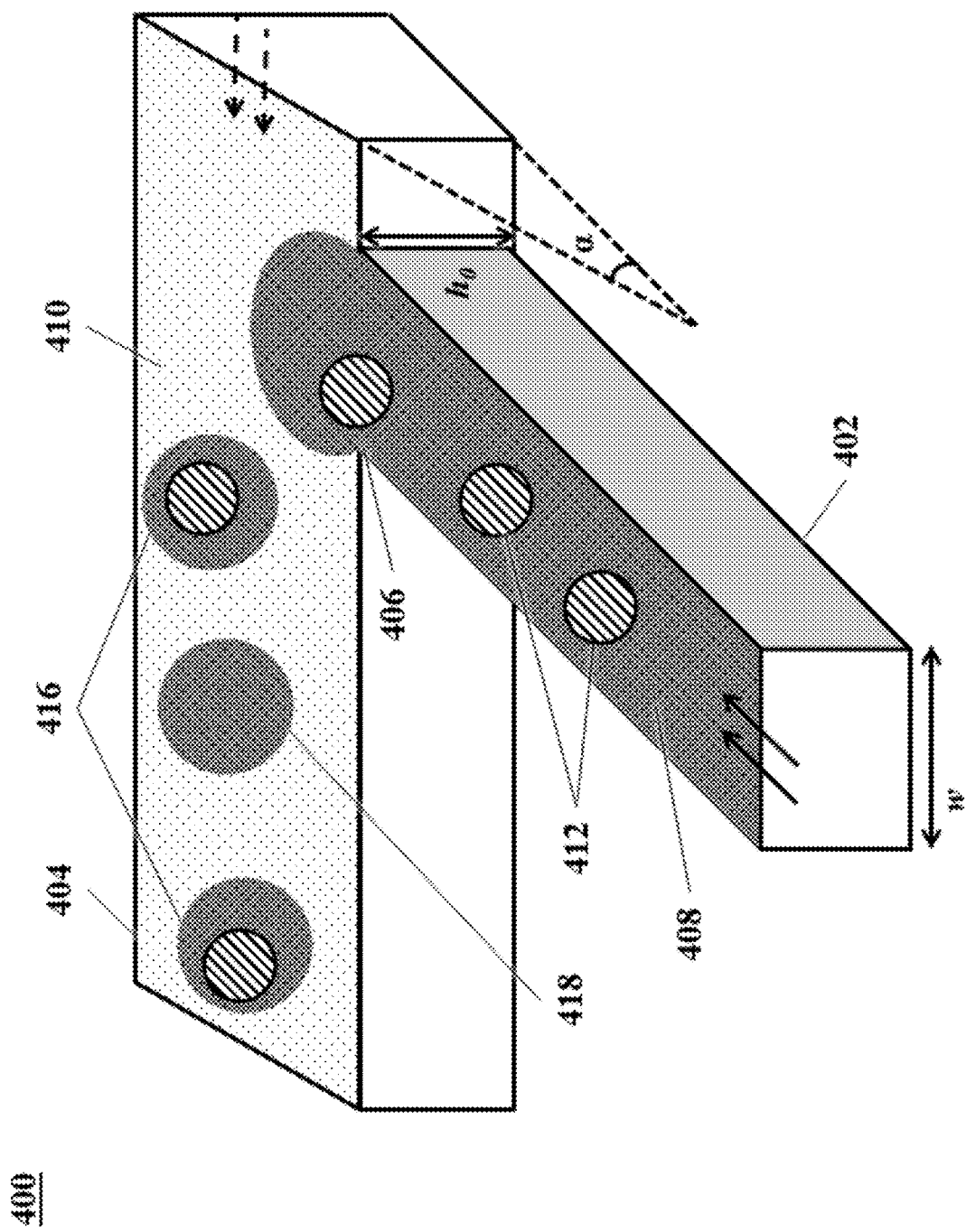
FIG. 4 shows an example of a microfluidic channel structure for the controlled partitioning of beads into discrete droplets.

FIG. 4 shows an example of a microfluidic channel structure for the controlled partitioning of beads into discrete droplets. A channel structure 400 can include a channel segment 402 communicating at a channel junction 406 (or intersection) with a reservoir 404. The reservoir 404 can be a chamber. Any reference to "reservoir," as used herein, can also refer to a "chamber." In operation, an aqueous fluid 408 that includes suspended beads 412 may be transported along the channel segment 402 into the junction 406 to meet a second fluid 410 that is immiscible with the aqueous fluid 408 in the reservoir 404 to create droplets 416, 418 of the aqueous fluid 408 flowing into the reservoir 404. At the juncture 406 where the aqueous fluid 408 and the second fluid 410 meet, droplets can form based on factors such as the hydrodynamic forces at the juncture 406, flow rates of the two fluids 408, 410, fluid properties, and certain geometric parameters (e.g., w, $h_0$, α, etc.) of the channel structure 400. A plurality of droplets can be collected in the reservoir 404 by continuously injecting the aqueous fluid 408 from the channel segment 402 through the juncture 406.

A discrete droplet generated may include a bead (e.g., as in occupied droplets 416). Alternatively, a discrete droplet generated may include more than one bead. Alternatively, a discrete droplet generated may not include any beads (e.g., as in unoccupied droplet 418). In some instances, a discrete droplet generated may contain one or more biological particles, as described elsewhere herein. In some instances, a discrete droplet generated may comprise one or more reagents, as described elsewhere herein.

In some instances, the aqueous fluid 408 can have a substantially uniform concentration or frequency of beads 412. The beads 412 can be introduced into the channel segment 402 from a separate channel (not shown in FIG. 4). The frequency of beads 412 in the channel segment 402 may be controlled by controlling the frequency in which the beads 412 are introduced into the channel segment 402 and/or the relative flow rates of the fluids in the channel segment 402 and the separate channel. In some instances, the beads can be introduced into the channel segment 402 from a plurality of different channels, and the frequency controlled accordingly.

In some instances, the aqueous fluid 408 in the channel segment 402 can comprise biological particles (e.g., described with reference to FIGS. 1 and 2). In some instances, the aqueous fluid 408 can have a substantially uniform concentration or frequency of biological particles. As with the beads, the biological particles can be introduced into the channel segment 402 from a separate channel. The frequency or concentration of the biological particles in the aqueous fluid 408 in the channel segment 402 may be controlled by controlling the frequency in which the biological particles are introduced into the channel segment 402 and/or the relative flow rates of the fluids in the channel segment 402 and the separate channel. In some instances, the biological particles can be introduced into the channel segment 402 from a plurality of different channels, and the frequency controlled accordingly. In some instances, a first separate channel can introduce beads and a second separate channel can introduce biological particles into the channel segment 402. The first separate channel introducing the beads may be upstream or downstream of the second separate channel introducing the biological particles.

The second fluid 410 can comprise an oil, such as a fluorinated oil, that includes a fluorosurfactant for stabilizing the resulting droplets, for example, inhibiting subsequent coalescence of the resulting droplets.

In some instances, the second fluid 410 may not be subjected to and/or directed to any flow in or out of the reservoir 404. For example, the second fluid 410 may be substantially stationary in the reservoir 404. In some instances, the second fluid 410 may be subjected to flow within the reservoir 404, but not in or out of the reservoir 404, such as via application of pressure to the reservoir 404 and/or as affected by the incoming flow of the aqueous fluid 408 at the juncture 406. Alternatively, the second fluid 410 may be subjected and/or directed to flow in or out of the reservoir 404. For example, the reservoir 404 can be a channel directing the second fluid 410 from upstream to downstream, transporting the generated droplets.

The channel structure 400 at or near the juncture 406 may have certain geometric features that at least partly determine the sizes of the droplets formed by the channel structure 400. The channel segment 402 can have a height, $h_0$ and width, w, at or near the juncture 406. By way of example, the channel segment 402 can comprise a rectangular cross-section that leads to a reservoir 404 having a wider cross-section (such as in width or diameter). Alternatively, the cross-section of the channel segment 402 can be other shapes, such as a circular shape, trapezoidal shape, polygonal shape, or any other shapes. The top and bottom walls of the reservoir 404 at or near the juncture 406 can be inclined at an expansion angle, $\alpha$. The expansion angle, $\alpha$, allows the tongue (portion of the aqueous fluid 408 leaving channel segment 402 at junction 406 and entering the reservoir 404 before droplet formation) to increase in depth and facilitate decrease in curvature of the intermediately formed droplet. Droplet size may decrease with increasing expansion angle. The resulting droplet radius, $R_d$, may be predicted by the following equation for the aforementioned geometric parameters of $h_0$, w, and $\alpha$:

$$R_d \approx 0.44\left(1 + 2.2\sqrt{\tan\alpha}\,\frac{w}{h_0}\right)\frac{h_0}{\sqrt{\tan\alpha}}$$

By way of example, for a channel structure with w=21 μm, h=21 μm, and $\alpha$=3°, the predicted droplet size is 121 μm. In another example, for a channel structure with w=25 μm, h=25 μm, and $\alpha$=5°, the predicted droplet size is 123 μm. In another example, for a channel structure with w=28 μm, h=28 μm, and $\alpha$=7°, the predicted droplet size is 124 μm.

In some instances, the expansion angle, $\alpha$, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 408 entering the junction 406 can be between about 0.04 microliters (μL)/minute (min) and about 40 μL/min. In some instances, the flow rate of the aqueous fluid 408 entering the junction 406 can be between about 0.01 microliters (μL)/minute (min) and about 100 μL/min. Alternatively, the flow rate of the aqueous fluid 408 entering the junction 406 can be less than about 0.01 μL/min. Alternatively, the flow rate of the aqueous fluid 408 entering the junction 406 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 408 entering the junction 406.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 406) between aqueous fluid 408 channel segments (e.g., channel segment 402) and the reservoir 404. Alternatively, or in addition, the throughput of droplet generation can be increased by increasing the flow rate of the aqueous fluid 408 in the channel segment 402.

Figure 5:
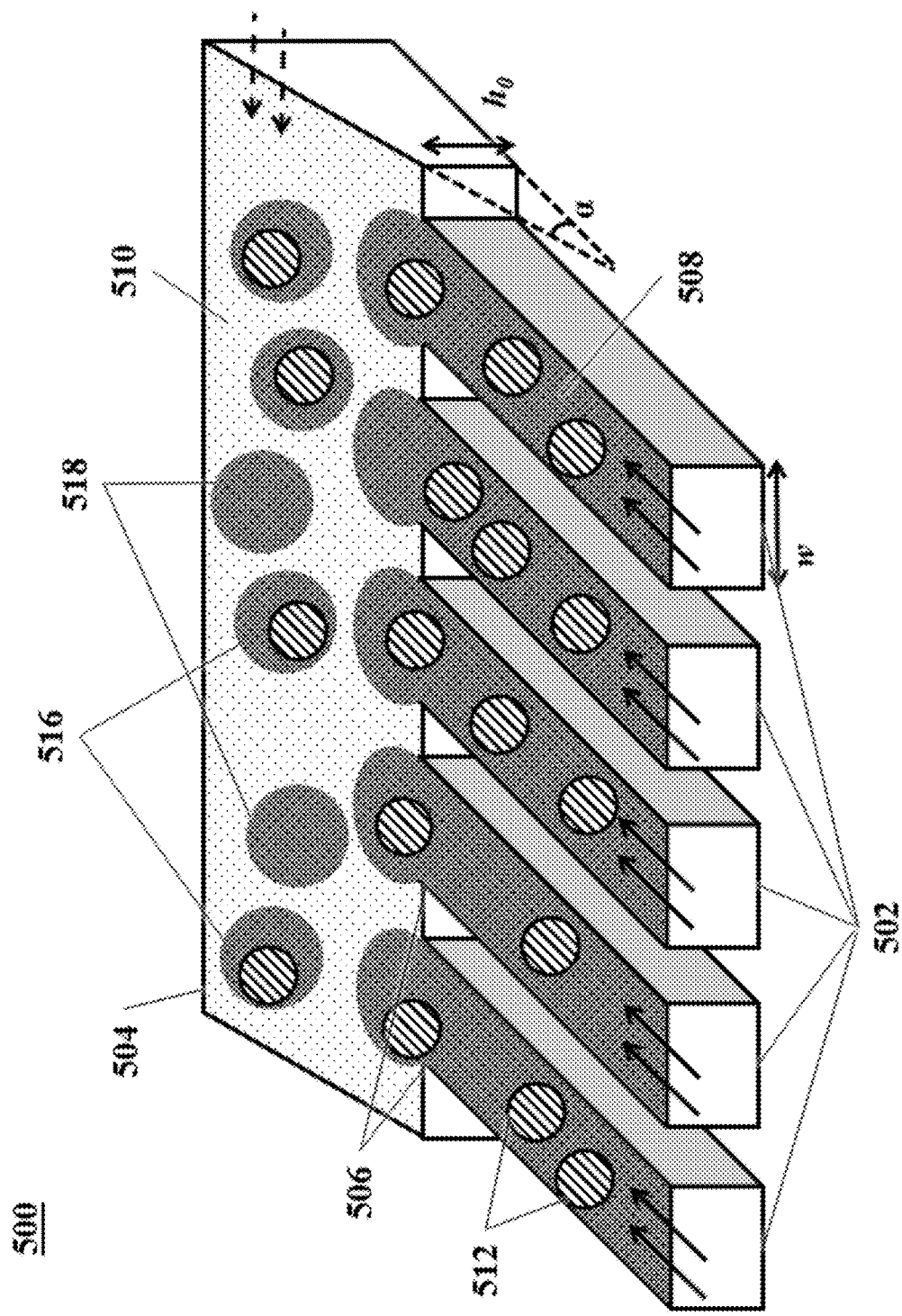
FIG. 5 shows an example of a microfluidic channel structure for increased droplet generation throughput.

FIG. 5 shows an example of a microfluidic channel structure for increased droplet generation throughput. A microfluidic channel structure 500 can comprise a plurality of channel segments 502 and a reservoir 504. Each of the plurality of channel segments 502 may be in fluid communication with the reservoir 504. The channel structure 500 can comprise a plurality of channel junctions 506 between the plurality of channel segments 502 and the reservoir 504. Each channel junction can be a point of droplet generation. The channel segment 402 from the channel structure 400 in FIG. 4 and any description to the components thereof may correspond to a given channel segment of the plurality of channel segments 502 in channel structure 500 and any description to the corresponding components thereof. The reservoir 404 from the channel structure 400 and any description to the components thereof may correspond to the reservoir 504 from the channel structure 500 and any description to the corresponding components thereof.

Each channel segment of the plurality of channel segments 502 may comprise an aqueous fluid 508 that includes suspended beads 512. The reservoir 504 may comprise a second fluid 510 that is immiscible with the aqueous fluid 508. In some instances, the second fluid 510 may not be subjected to and/or directed to any flow in or out of the reservoir 504. For example, the second fluid 510 may be substantially stationary in the reservoir 504. In some instances, the second fluid 510 may be subjected to flow within the reservoir 504, but not in or out of the reservoir 504, such as via application of pressure to the reservoir 504 and/or as affected by the incoming flow of the aqueous fluid 508 at the junctures. Alternatively, the second fluid 510 may be subjected and/or directed to flow in or out of the reservoir 504. For example, the reservoir 504 can be a channel directing the second fluid 510 from upstream to downstream, transporting the generated droplets.

In operation, the aqueous fluid 508 that includes suspended beads 512 may be transported along the plurality of channel segments 502 into the plurality of junctions 506 to meet the second fluid 510 in the reservoir 504 to create droplets 516, 518. A droplet may form from each channel segment at each corresponding junction with the reservoir 504. At the juncture where the aqueous fluid 508 and the second fluid 510 meet, droplets can form based on factors such as the hydrodynamic forces at the juncture, flow rates of the two fluids 508, 510, fluid properties, and certain geometric parameters (e.g., w, $h_0$, $\alpha$, etc.) of the channel structure 500, as described elsewhere herein. A plurality of droplets can be collected in the reservoir 504 by continuously injecting the aqueous fluid 508 from the plurality of channel segments 502 through the plurality of junctures 506. Throughput may significantly increase with the parallel channel configuration of channel structure 500. For example, a channel structure having five inlet channel segments comprising the aqueous fluid 508 may generate droplets five times as frequently than a channel structure having one inlet channel segment, provided that the fluid flow rate in the channel segments are substantially the same. The fluid flow rate in the different inlet channel segments may or may not be substantially the same. A channel structure may have as many parallel channel segments as is practical and allowed for the size of the reservoir. For example, the channel structure may have at least about 2, 3, 4, 5, 6, 7, 8, 9, 10, 20, 30, 40, 50, 60, 70, 80, 90, 100, 150, 500, 250, 300, 350, 400, 450, 500, 600, 700, 800, 900, 1000, 1500, 5000 or more parallel or substantially parallel channel segments.

The geometric parameters, w, $h_0$, and $\alpha$, may or may not be uniform for each of the channel segments in the plurality of channel segments 502. For example, each channel segment may have the same or different widths at or near its respective channel junction with the reservoir 504. For example, each channel segment may have the same or different height at or near its respective channel junction with the reservoir 504. In another example, the reservoir 504 may have the same or different expansion angle at the different channel junctions with the plurality of channel segments 502. When the geometric parameters are uniform, beneficially, droplet size may also be controlled to be uniform even with the increased throughput. In some instances, when it is desirable to have a different distribution of droplet sizes, the geometric parameters for the plurality of channel segments 502 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

Figure 6:
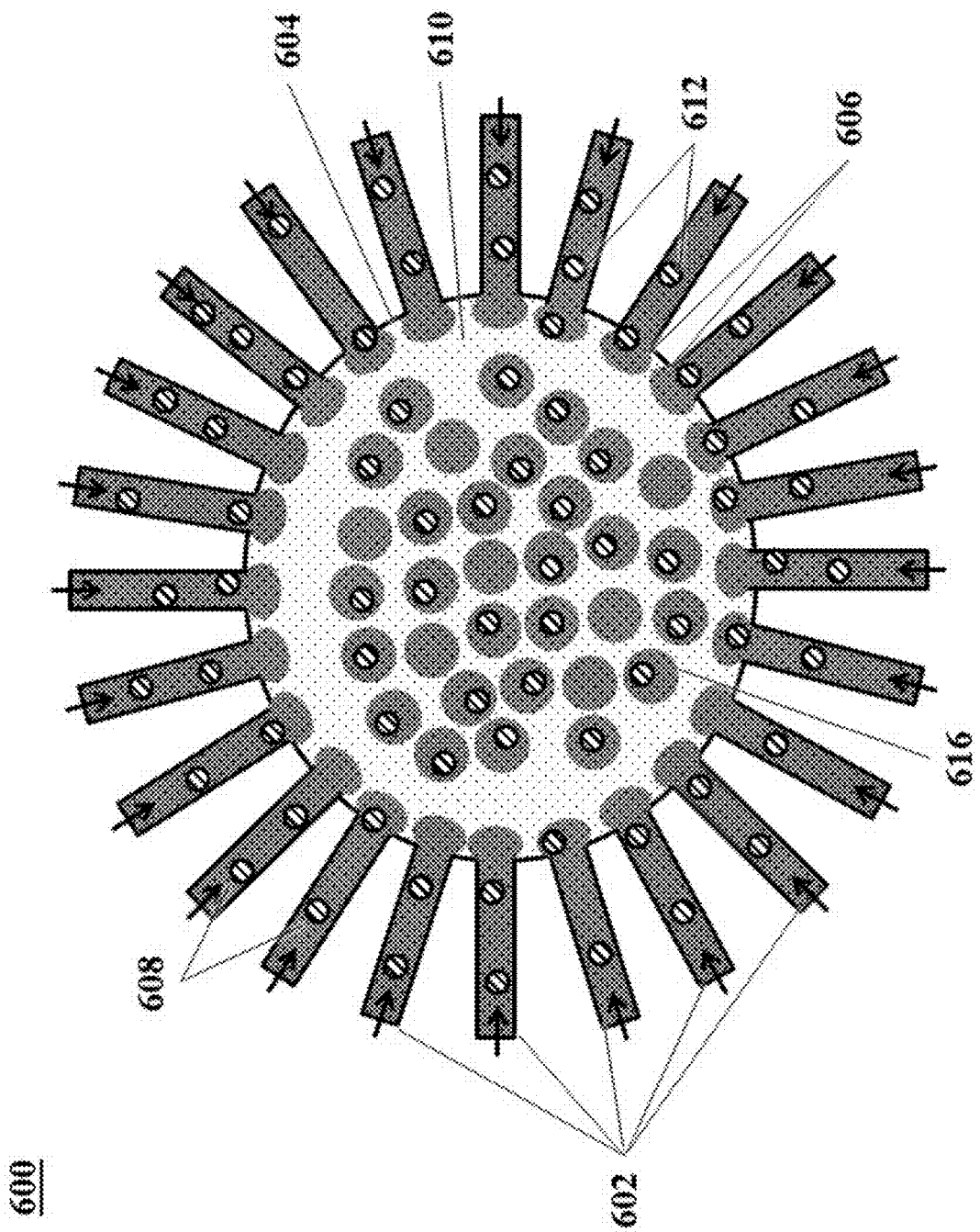
FIG. 6 shows another example of a microfluidic channel structure for increased droplet generation throughput.

FIG. 6 shows another example of a microfluidic channel structure for increased droplet generation throughput. A microfluidic channel structure 600 can comprise a plurality of channel segments 602 arranged generally circularly around the perimeter of a reservoir 604. Each of the plurality of channel segments 602 may be in fluid communication with the reservoir 604. The channel structure 600 can comprise a plurality of channel junctions 606 between the plurality of channel segments 602 and the reservoir 604. Each channel junction can be a point of droplet generation. The channel segment 402 from the channel structure 400 in FIG. 2 and any description to the components thereof may correspond to a given channel segment of the plurality of channel segments 602 in channel structure 600 and any description to the corresponding components thereof. The reservoir 404 from the channel structure 400 and any description to the components thereof may correspond to the reservoir 604 from the channel structure 600 and any description to the corresponding components thereof.

Each channel segment of the plurality of channel segments 602 may comprise an aqueous fluid 608 that includes suspended beads 612. The reservoir 604 may comprise a second fluid 610 that is immiscible with the aqueous fluid 608. In some instances, the second fluid 610 may not be subjected to and/or directed to any flow in or out of the reservoir 604. For example, the second fluid 610 may be substantially stationary in the reservoir 604. In some instances, the second fluid 610 may be subjected to flow within the reservoir 604, but not in or out of the reservoir 604, such as via application of pressure to the reservoir 604 and/or as affected by the incoming flow of the aqueous fluid 608 at the junctures. Alternatively, the second fluid 610 may be subjected and/or directed to flow in or out of the reservoir 604. For example, the reservoir 604 can be a channel directing the second fluid 610 from upstream to downstream, transporting the generated droplets.

In operation, the aqueous fluid 608 that includes suspended beads 612 may be transported along the plurality of channel segments 602 into the plurality of junctions 606 to meet the second fluid 610 in the reservoir 604 to create a plurality of droplets 616. A droplet may form from each channel segment at each corresponding junction with the reservoir 604. At the juncture where the aqueous fluid 608 and the second fluid 610 meet, droplets can form based on factors such as the hydrodynamic forces at the juncture, flow rates of the two fluids 608, 610, fluid properties, and certain geometric parameters (e.g., widths and heights of the channel segments 602, expansion angle of the reservoir 604, etc.) of the channel structure 600, as described elsewhere herein. A plurality of droplets can be collected in the reservoir 604 by continuously injecting the aqueous fluid 608 from the plurality of channel segments 602 through the plurality of junctures 606. Throughput may significantly increase with the substantially parallel channel configuration of the channel structure 600. A channel structure may have as many substantially parallel channel segments as is practical and allowed for by the size of the reservoir. For example, the channel structure may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 5000 or more parallel or substantially parallel channel segments. The plurality of channel segments may be substantially evenly spaced apart, for example, around an edge or perimeter of the reservoir. Alternatively, the spacing of the plurality of channel segments may be uneven.

The reservoir 604 may have an expansion angle, α (not shown in FIG. 6) at or near each channel juncture. Each channel segment of the plurality of channel segments 602 may have a width, w, and a height, $h_0$, at or near the channel juncture. The geometric parameters, w, $h_0$, and α, may or may not be uniform for each of the channel segments in the plurality of channel segments 602. For example, each channel segment may have the same or different widths at or near its respective channel junction with the reservoir 604. For example, each channel segment may have the same or different height at or near its respective channel junction with the reservoir 604.

The reservoir 604 may have the same or different expansion angle at the different channel junctions with the plurality of channel segments 602. For example, a circular reservoir (as shown in FIG. 6) may have a conical, dome-like, or hemispherical ceiling (e.g., top wall) to provide the same or substantially same expansion angle for each channel segments 602 at or near the plurality of channel junctions 606. When the geometric parameters are uniform, beneficially, resulting droplet size may be controlled to be uniform even with the increased throughput. In some instances, when it is desirable to have a different distribution of droplet sizes, the geometric parameters for the plurality of channel segments 602 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size. The beads and/or biological particle injected into the droplets may or may not have uniform size.

The channel networks, e.g., as described above or elsewhere herein, can be fluidly coupled to appropriate fluidic components. For example, the inlet channel segments are fluidly coupled to appropriate sources of the materials they are to deliver to a channel junction. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like. Likewise, the outlet channel segment (e.g., channel segment 208, reservoir 604, etc.) may be fluidly coupled to a receiving vessel or conduit for the partitioned cells for subsequent processing. Again, this may be a reservoir defined in the body of a microfluidic device, or it may be a fluidic conduit for delivering the partitioned cells to a subsequent process operation, instrument or component.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken, and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

Methods for Forming Gel Matrix

The methods and systems described herein may be used to generate discrete droplets comprising an individual biological particle and polymer molecules configured to be crosslinked under controlled conditions (e.g., click chemistry). In some cases, the crosslinked polymers can be a degradable matrix. In some cases, the crosslinked polymers can be a gel. In some cases, the crosslinked polymers can be a hydrogel matrix. In some cases, the crosslinked polymers can enclose a biological sample, e.g., a cell or a nucleic acid. In some cases, additional reagents can permeate into the crosslinked matrix. In some cases, the crosslink(s) between polymer molecules can be cleavable and the contents enclosed within the matrix can be released after the matrix is cleaved or degraded. In some cases, the crosslinked matrix and/or contents enclosed therein can be barcoded.

Figure 7:
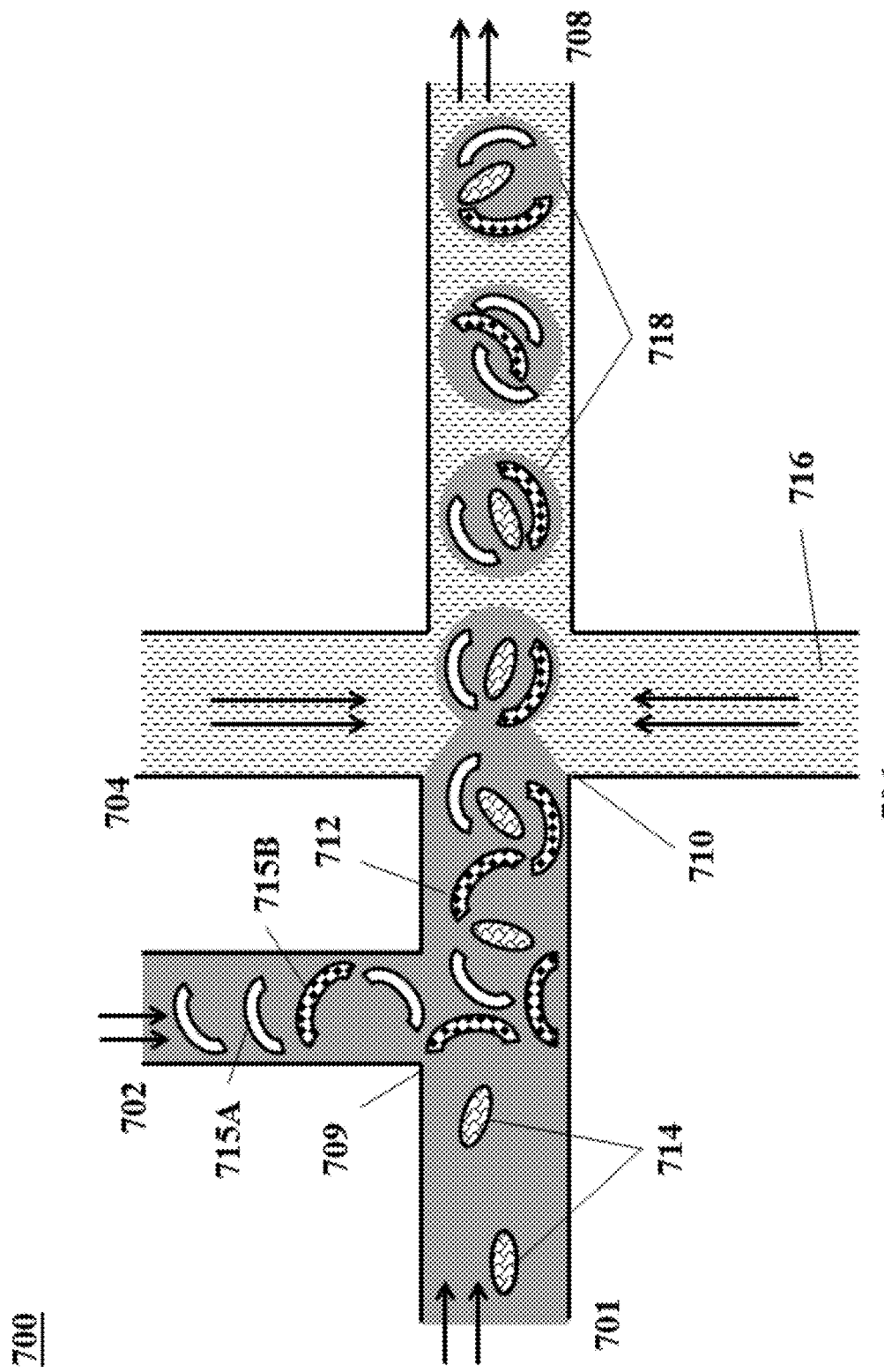
FIG. 7 shows an example of a microfluidic channel structure for co-partitioning biological particles and reagents to form droplets configured to form hydrogels.

FIG. 7 shows an example of a microfluidic channel structure 700 for co-partitioning biological particles and reagents to generate a crosslinked hydrogel matrix. The channel structure 700 can include channel segments 701, 702, 704, 706 and 708. Channel segments 701 and 702 communicate at a first channel junction 709. Channel segments 701, 702, 704, 706, and 708 communicate at a second channel junction 710.

In an example operation, the channel segment 701 may transport an aqueous fluid 712 that includes a plurality of biological particles 714 along the channel segment 701 into the second junction 710. As an alternative or in addition to, channel segment 701 may transport beads (e.g., gel beads). The beads may comprise barcode molecules.

For example, the channel segment 701 may be connected to a reservoir comprising an aqueous suspension of biological particles 714. Upstream of, and immediately prior to reaching, the second junction 710, the channel segment 701 may meet the channel segment 702 at the first junction 709. The channel segment 702 may transport a plurality of reagents 715A (e.g., polymer molecules A) and 715B (e.g., polymer molecules B) suspended in the aqueous fluid 712 along the channel segment 702 into the first junction 709. For example, the channel segment 702 may be connected to a reservoir comprising the reagents 715A and 715B. After the first junction 709, the aqueous fluid 712 in the channel segment 701 can carry both the biological particles 714 and the reagents 715A and 715B towards the second junction

710. In some instances, the aqueous fluid 712 in the channel segment 701 can include one or more reagents, which can be the same or different reagents as the reagents 715A and 715B. A second fluid 716 (e.g., oil) that is immiscible with the aqueous fluid 712 can be delivered to the second junction 710 from each of channel segments 704 and 706. Upon meeting of the aqueous fluid 712 from the channel segment 701 and the second fluid 716 from each of channel segments 704 and 706 at the second channel junction 710, the aqueous fluid 712 can be partitioned as discrete droplets 718 in the second fluid 716 and flow away from the second junction 710 along channel segment 708. The channel segment 708 may deliver the discrete droplets 718 to an outlet reservoir fluidly coupled to the channel segment 708, where they may be harvested.

The second fluid 716 can comprise an oil, such as a fluorinated oil, that includes a fluorosurfactant for stabilizing the resulting droplets, for example, inhibiting subsequent coalescence of the resulting droplets 718.

A discrete droplet generated may include an individual biological particle 714 and/or one or more of reagents 715A and 715B. In some instances, a discrete droplet generated may include a barcode carrying bead (not shown), such as via other microfluidics structures described elsewhere herein. In some instances, a discrete droplet may be unoccupied (e.g., no reagents, no biological particles). As shown below, click chemistry can be used to crosslink polymer molecules trapped in the same discrete droplet to generate hydrogels (e.g., 715A and 715B). In some cases, click chemistry can be used to generate degradable hydrogels (e.g., 715A and 715B).

Gel

As used herein, the term "gel" generally refers to a three-dimensional polymeric matrix; a hydrogel is an example of a gel. A gel can have both liquid and solid characteristics and may exhibit an organized material structure. A hydrogel may be a three-dimensional, hydrophilic, polymeric matrix that is configured to absorb/contain water or biological fluids. In some cases, hydrogels can become swollen with water when water is the dispersion medium. See, e.g., Eur. Polym. J., 2015, 65:252-67 and J. Adv. Res, 2015, 6:105-21, each of which is entirely incorporated herein by reference for all purposes. Hydrogels can take many forms. In some cases, hydrogels can be a water-swollen, cross-linked polymeric network created by cross-linking reactions between monomers. In some cases, hydrogels can be a polymeric material that retaining water within its matrix but may not dissolve in water.

Hydrogels can be synthesized in many ways. In some cases, hydrogels can be synthesized in one-step procedures, e.g., polymerization and concurrent cross-linking reactions of multifunctional monomers. In some cases, hydrogels can be synthesized in multi-steps procedures, e.g., polymerization of monomers first, followed by crosslinking reactions by using orthogonal, reactive groups that can respond to different conditions to allow stepwise approaches.

Hydrogel products can be classified base on their polymeric compositions (homopolymeric hydrogels, copolymeric hydrogels, or multipolymer hydrogels), types of crosslinking (chemically crosslinked or physically crosslinked), physical appearance (matrix, film, or microsphere), network electrical charge (nonionic, ionic, amphoteric or ampholytic, or zwitterionic), and sources (natural (e.g., chitosan) or synthetic (e.g., polyacrylamide)).

Hydrogels can be synthesized by techniques that can create a crosslinked polymer. In some cases, copolymerization/cross-linking free radical polymerizations can be used to produce hydrogels by reacting hydrophilic monomers with multifunctional crosslinking molecules. This can be done by, for example, linking polymer chains via chemical reaction, using ionizing radiation to generate main-chain free radicals which can recombine as crosslinking junctions, or physical interactions such as entanglements, electrostatics, and crystallite formation. Types of polymerization can include bulk, solution, and suspension polymerization.

Suspension polymerization or dispersion polymerization can be employed in water-in-oil or emulsion processes, sometimes called "inversion suspension." In some cases, the monomers and initiators can be dispersed in the oil or hydrocarbon phase as a homogenous mixture. In some cases, two types of polymer molecules can be first produced, each having a reactive, crosslinking moiety for cross-linking purposes. Then these two types of polymer molecules can be enclosed in an emulsion such that the two reactive, crosslinking moieties can react and form crosslinks between the two types of polymers, thereby completing the synthesis of the hydrogel.

In some cases, hydrogels can be synthesized from monomers, polymerization initiators, and crosslinking reagents. After the polymerization reactions are complete, the hydrogels formed can be separated from remaining starting materials and unwanted by-products, etc. The length of the polymer formed can be controlled depending on the desired properties of the hydrogels.

Types of polymerizations employed to synthesize hydrogels can include, but are not limited to, graft polymerization, crosslinking polymerization, networks formation of water-soluble polymers, and radiation crosslinking polymerization, etc.

Polymerization can be initiated by initiators or free-radical generating compounds, such as, for example, benzoyl peroxide, 2,2-azo-isobutyronitrile (AIBN), and ammonium peroxodisulphate, or by using UV-, gamma- or electron beam-radiation.

In some cases, the hydrogels disclosed herein comprise polymers such as poly(acrylic acid), poly(vinyl alcohol), poly(vinylpyrrolidone), poly(ethylene glycol), polyacrylamide, some polysaccharides, or any derivatives thereof. These polymers can be non-toxic, and they can be used in various pharmaceutical and biomedical applications. Thus, in some instances, they may not require their removal from the reaction system, thereby eliminating the need for a purification step after the formation of hydrogels.

Polymers can comprise polymer molecules of a particular length or range of lengths. Polymer molecules can have a length of at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 1,000, 2,000, 5,000, 10,000, 20,000, 50,000, 100,000, 200,000, 500,000, 1,000,000, 2,000,000, 5,000,000, 10,000,000, 20,000,000, 100,000,000, 200,000,000, 500,000,000 or 1,000,000,000 backbone atoms or molecules (e.g., carbons). Polymer molecules can have a length of at most 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 1,000, 2,000, 5,000, 10,000, 20,000, 50,000, 100,000, 200,000, 500,000, 1,000,000, 2,000,000, 5,000,000, 10,000,000, 20,000,000, 100,000,000, 200,000,000, 500,000,000 or 1,000,000,000 backbone atoms or molecules (e.g., carbons). Polymer molecules can have a length of at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 1,000, 2,000, 5,000, 10,000, 20,000, 50,000, 100,000, 200,000, 500,000, 1,000,000, 2,000,000, 5,000,000, 10,000,000, 20,000,000, 100,000,000, 200,000,000, 500,000,000 or 1,000,000,000 monomer units (e.g., vinyl molecules or acrylamide molecules). Polymer molecules can have a length of at most 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 1,000, 2,000, 5,000, 10,000, 20,000, 50,000, 100,000, 200,000, 500,000, 1,000,000, 2,000,000, 5,000,000, 10,000,000, 20,000,000, 100,000,000, 200,000,000, 500,000,000 or 1,000,000,000 monomer units (e.g., vinyl molecules or acrylamide molecules).

Click Chemistry

As used herein, the term "click chemistry," generally refers to reactions that are modular, wide in scope, give high yields, generate only inoffensive byproducts, such as those that can be removed by nonchromatographic methods, and are stereospecific (but not necessarily enantioselective). See, e.g., Angew. Chem. Int. Ed., 2001, 40(11):2004-2021, which is entirely incorporated herein by reference for all purposes. In some cases, click chemistry can describe pairs of functional groups that can selectively react with each other in mild, aqueous conditions.

An example of click chemistry reaction can be the Huisgen 1,3-dipolar cycloaddition of an azide and an alkynes, i.e., Copper-catalyzed reaction of an azide with an alkyne to form a 5-membered heteroatom ring called 1,2,3-triazole. The reaction can also be known as a Cu(I)-Catalyzed Azide-Alkyne Cycloaddition (CuAAC), a Cu(I) click chemistry or a Cu$^+$ click chemistry. Catalyst for the click chemistry can be Cu(I) salts, or Cu(I) salts made in situ by reducing Cu(II) reagent to Cu(I) reagent with a reducing reagent (Pharm Res. 2008, 25(10): 2216-2230). Known Cu(II) reagents for the click chemistry can include, but are not limited to, Cu(II)-(TBTA) complex and Cu(II) (THPTA) complex. TBTA, which is tris-[(1-benzyl-1H-1,2,3-triazol-4-yl)methyl]amine, also known as tris-(benzyltriazolylmethyl)amine, can be a stabilizing ligand for Cu(I) salts. THPTA, which is tris-(hydroxypropyltriazolylmethyl) amine, can be another example of stabilizing agent for Cu(I). Other conditions can also be accomplished to construct the 1,2,3-triazole ring from an azide and an alkyne using copper-free click chemistry, such as by the Strain-promoted Azide-Alkyne Click chemistry reaction (SPAAC, see, e.g., Chem. Commun, 2011, 47:6257-6259 and Nature, 2015, 519 (7544):486-90), each of which is entirely incorporated herein by reference for all purposes.

The present disclosure also contemplates the use of click chemistry reactions resulting in chemical linkages that are not a 1,2,3-triazole. A range of such click chemistry reactions useful for preparing biocompatible gels are well-known in the art. See e.g., Madl and Heilshorn, "Bioorthogonal Strategies for Engineering Extracellular Matrices," *Adv. Funct. Mater.* 2018, 28: 1706046, which is hereby incorporated by reference herein.

An example of a click chemistry reaction useful in the compositions and methods of the present disclosure that is copper-free and does not result in a 1,2,3-triazole linkage is an Inverse-electron demand Diels-Alder (IED-DA) reaction. (See e.g., Madl and Heilshorn 2018.) As described elsewhere herein, in the IED-DA click chemistry reaction, the pair of click chemistry functional groups comprises a tetrazine group and a trans-cyclooctene (TCO) group, or a tetrazine group and a norbonene group. This reaction is copper free and results in a linkage comprising a dihydropyridazine group rather than a 1,2,3-triazole.

Other specific biorthogonal click chemistry reactions that are useful in the compositions and methods of the present disclosure, but which result in a chemical linkage other than a 1,2,3-triazole include a Diels-Alder reaction between a pair of furan and maleimide functional groups, a Staudinger ligation, and nitrile oxide cycloaddition. These click chemistry reactions and others are well-known in the art and described in e.g., Madl and Heilshorn 2018.

Accordingly, in some embodiments the copper-free click chemistry useful in forming crosslinked polymers of the present disclosure can be selected from: (a) strain-promoted azide/dibenzocyclooctyne-amine (DBCO) click chemistry; (b) inverse electron demand Diels-Alder (IED-DA) tetrazine/trans-cyclooctene (TCO) click chemistry; (c) inverse electron demand Diels-Alder (IED-DA) tetrazine/norbonene click chemistry; (d) Diels-Alder maleimide/furan click-chemistry; (e) Staudinger ligation; and (f) nitrile-oxide/norbonene cycloaddition click chemistry.

Figure 8:
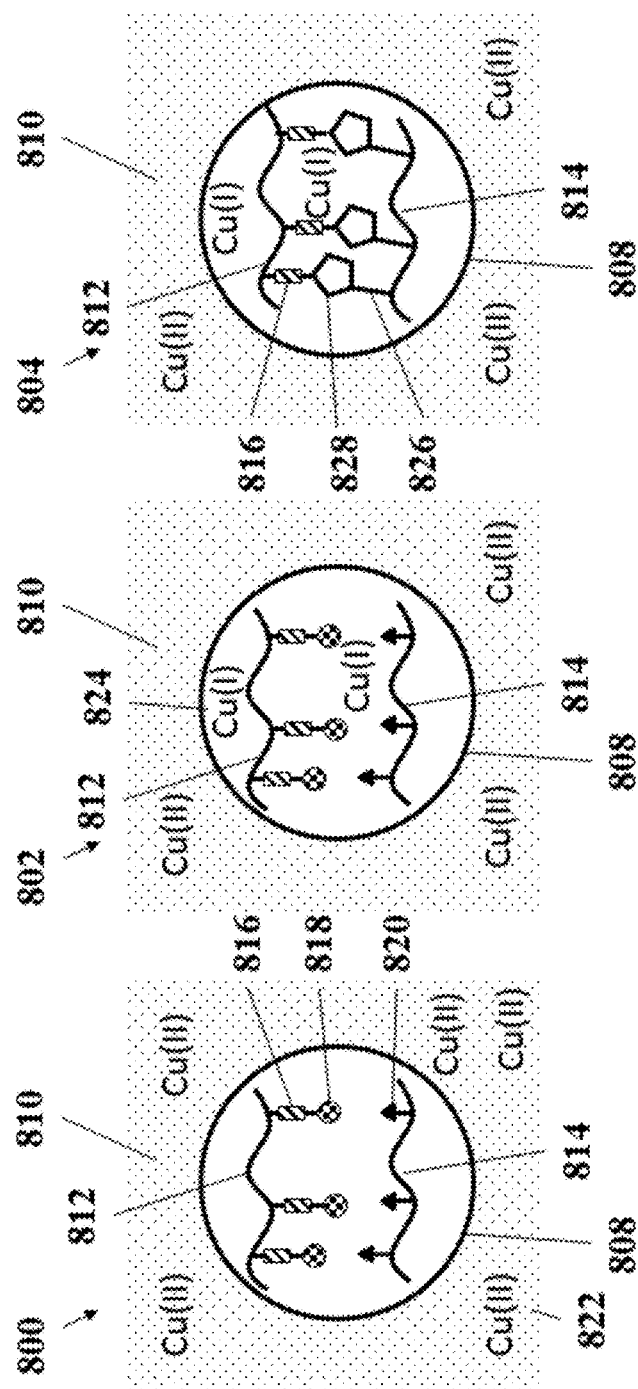
FIG. 8 shows an example hydrogel composition and steps for forming hydrogels in a droplet.

For example, a discrete droplet 718 shown in FIG. 7 can be subject to copper-catalyzed click chemistry conditions shown in FIG. 8. FIG. 8 shows an example process of forming hydrogels via click chemistry in an emulsion system. As shown in FIG. 8, emulsion systems 800, 802 and 804 can represent different stages through which polymer molecules are crosslinked to form a hydrogel. Emulsion system 800 can comprise a discrete droplet 808 (comprising water) immersed in the oil phase 810. Within the discrete droplet 808, two polymer molecules 812 and 814 can be partitioned together. Polymer molecule 812 can comprise a first crosslink precursor comprising a labile bond 816 (e.g., a disulfide bond) and a first click chemistry moiety 818. Polymer molecule 814 can comprise a second click chemistry moiety 820. In addition, in the oil phase 810, there can be other reagents, such as reagent 822 (shown as a copper (II) reagent) which may be required to facilitate the click chemistry reaction between the first click chemistry moiety 818 and the second click chemistry moiety 820, either by itself or by a derivative thereof. Because the reagent 822 remains outside of the discrete droplet 808, generally no click chemistry reaction happens within the discrete droplet 808.

In emulsion system 802, some of the reagent 822 can penetrate into the discrete droplet 808, via physical or chemical processes. In some instances, reagent 822 becomes or is otherwise processed to become reagent 824 (shown as a copper (I) reagent) in the discrete droplet 808. The conversion into reagent 824 can require additional reagents (not shown, e.g., a reducing agent such as sodium ascorbate). In these embodiments, reagent 824 can be the reagent required to initiate the click chemistry reaction between the first click chemistry moiety 818 and the second click chemistry moiety 820. Once in the proximity of both the first click chemistry moiety 818 and the second click chemistry moiety 820, the reagent 824 can initiate a click chemistry reaction, such as a Cu(I)—Catalyzed Azide-Alkyne Cycloaddition (CuAAC), see emulsion system 804.

As shown in the emulsion system 804 of FIG. 8, in the presence of the reagent 824, a crosslink 826 is formed linking the two polymer molecules 812 and 814 together, via the newly formed moiety 828 as a result of the click chemistry reaction between the first click chemistry moiety 818 and the second click chemistry moiety 820. A hydrogel comprising the crosslinked polymer molecules 812 and 814 can thus be formed. Reagents 822 and/or 824 can be removed from the newly formed hydrogel if desired. In some instances, a stimulus (e.g., a chemical, thermal, or photo-stimulus) is applied to labile bond 816 to release the crosslinks 826 and/or degrade the hydrogel.

Copolymer with Click Chemistry Moieties

Scheme 1 below depicts an example synthetic pathway leading to the generation of a pair of polymer molecules comprising click chemistry moieties to be used in a subsequent copolymerization reaction.

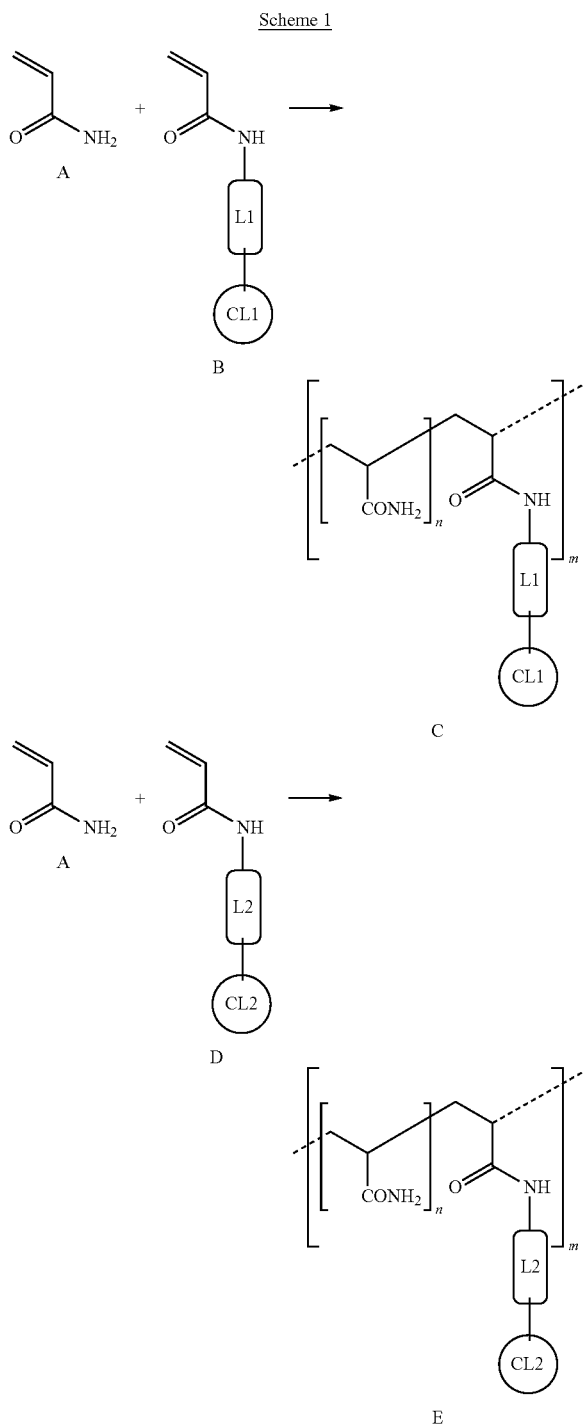

Monomer A can react with monomer B to produce polymer C. Monomer B can comprise a linker L1 between a polymerizable moiety and a click chemistry moiety CL1. By varying the reaction conditions, the polymer C can comprise repeatable units of the formula shown in Scheme 1 in that a stretch of n (n is an integer more than 1) repeating regular polymer units is sandwiched by at least one polymer unit that comprises the click chemistry moiety CL1, and that there will be a total of m (m is a positive integer) units comprising the click chemistry moiety CL1. The relative ratio between the repeating regular polymer unit and the unit bearing the click chemistry moiety can be controlled in various ways, include varying the relative amount of the corresponding monomers A and B. The molecular weight and the length of the polymer C can be controlled by the chain termination conditions. Similarly, monomer A can react with monomer D to produce polymer E. Monomer D can comprise a linker L2 between a polymerizable moiety and a click chemistry moiety CL2. By varying the reaction conditions, the polymer E can comprise repeatable units of the formula shown in Scheme 1 in that a stretch of n (n is an integer more than 1) repeating regular polymer units is sandwiched by at least one polymer unit that comprises the click chemistry moiety CL2, and that there will be a total of m (m is a positive integer) units comprising the click chemistry moiety CL2. The relative ratio between the repeating regular polymer unit and the polymer unit bearing the click chemistry moiety can be controlled in various ways, include varying the relative amount of the corresponding monomers A and D. The molecular weight and the length of the polymer E can be controlled by the chain termination conditions. The integers n and m are independent in each instance in Scheme 1 in that the polymers C and E can have the same or difference integer n's and m's.

The length and/or the chemical composition of the linkers L1 and L2 can vary, depending on the size of the pore of the hydrogel, the rigidity of the linkers, the hydrophilicity of the linkers, etc. Generally, the linkers L1 and L2 can comprise any chemical groups compatible with the desired click-chemistry reaction conditions, the desired polymerization conditions, and/or the desired cell-bead conditions. Accordingly, in some embodiments, the composition of linkers L1 and L2 can comprise chemical groups selected from amine, amide, aryl, imide, carbonate, carbamate, dihydropyridazine, ester, ether, heteroaryl, hydrazone, oxime, phosphodiester, polyethylene glycol (PEG), squarate, thiazole, thiazolidine, thioether, triazole, or any combination thereof. In some embodiments, the composition of linkers L1 and L2 can each comprise alkyl, alkoxy, alkylamino, alkylaminoalkyl, alkoxyalkyl, arylalkyl, arylalkoxy, arylalkylamino, heteroarylalkyl, heteroarylalkoxy, heteroarylalkylamino, or any combinations thereof.

In some embodiments, at least one of the linkers L1 and L2 comprises a copper-chelating chemical group. The presence of a copper-chelating group in the linker L1 or L2 adjacent to the click-chemistry moiety CL1 or CL2 can facilitate an accelerated click chemistry reaction due to the chelating group effectively increasing the concentration of the copper ion at the site of the reaction. See e.g., Uttamapinant et al., "Fast, Cell-compatible Click Chemistry with Copper-chelating Azides for Biomolecular Labeling," *Angew. Chem. Int. Ed. Eng.* 2012 Jun. 11; 51(24): 5852-5856, which is hereby incorporated by reference herein. Additionally, the use of a copper-chelating linker with a click chemistry moiety, such as an azide-picolyl group, can allow for the use of significantly reduced copper concentrations in carrying out a polymer cross-linking reaction as described in the methods of the present disclosure. In some embodiments, the linkers L1 and L2 comprising a copper-chelating group, such as a picolyl group, can allow a reduction of the copper concentration in the click chemistry reaction by an amount of at least 10%, at least 25%, at least 50%, or at least 75% or more. In turn, the use of a lower copper concentration can provide for greatly increased yields of biological molecules, e.g., reduced RNA degradation, in cell-beads and gel-beads made using the low copper reactions. In some embodiments, the use of copper-chelating groups in linkers can result in an increase in genes detected (e.g., in a cell-bead based gene expression measurement) by an amount of at least 10%, at least 25%, at least 50%, or at least 75% or more. The incorporation of the exemplary copper-chelating group, azide-picolyl, in the click chemistry methods of the present disclosure is further described in the Examples.

In some cases, at least one of the linkers L1 and L2 further comprises a labile bond. In some embodiments, linkers L1 and/or L2 can further comprise more than one labile bond(s), including bio-orthogonal labile bond(s). Exemplary types of labile bond(s) that can be included in L1 and/or L2 can group can then undergo a standard CuAAC click chemistry reaction with an azide modified linker on a second polymer to result in a 1,2,3-triazole crosslinked gel matrix as shown in FIG. 34B. This gel matrix crosslinked by a specific polypeptide sequence can then be selectively degraded enzymatically by exposure to a protease selective for a peptide linkage in the sequence. As shown in FIG. 34B, a protease, e.g., Type II collagenase, can selectively cleave an 8-mer polypeptide sequence, e.g., GGRMSMPV, at the peptide linkage between the M and the S amino acid residues.

Specific proteases are well-known that can selectively cleave a specific peptide linkage in a polypeptide sequence. It is also contemplated that the protease used for degrading polymer crosslinks in a gel does not cleave other peptides/proteins that may be present in a cell-bead based biological assay system, such as a polymerase or reverse transcriptase. Exemplary proteases that are highly selective for specific polypeptide sequence and may be used in embodiments related to selectively degrading a hydrogel matrix in the presence of biological particles and other macromolecular constituents are provided below in Table 1.

TABLE 1

| Enzyme Name | Cleavage Tag Name | Cleavage Sequence/Site |
| --- | --- | --- |
| Human Rhinovirus (HRV) 3C Protease | 3C ('PreScission') cleavage tag | LEVLFQ/GP (/ = main cleavage site) |
| Enterokinase | EKT (Enterokinase) cleavage tag | DDDDK/ (/ = main cleavage site) |
| Type II Collagenase | — | GGRM/SMPV (/ = main cleavage site) | include a chemically labile bond, a thermally labile bond, a photo-labile bond, an enzymatically labile bond, or a combination thereof. More specific examples of labile bonds that may be part of L1 and L2 can include a disulfide bond, an ester linkage, a carbamate linkage, a vicinal diol linkage, a Diels-Alder linkage, a sulfone linkage, a silyl ether linkage, a glycosidic linkage, a peptide linkage, or a phosphodiester linkage. The labile bond also can be a bond cleavable by a nucleic acid targeting enzyme, such as restriction enzyme.

In some embodiments, the linkers L1 and L2 further comprise a disulfide bond. The ability to cleave disulfide bonds with the reductant dithiothreitol (DTT) is well-known in the art. The incorporation of labile disulfide bonds in linkers L1 and L2 in embodiments of the present disclosure are further described in the Examples.

In some cases, however, it is desirable to have DTT present in a reagent mix for a cell-bead based reaction yet still be able to cleave linkers L1 and L2 selectively. Accordingly, in some embodiments, the linkers L1 and L2 can further comprise a labile bond that is a carbamate linkage. A carbamate linkage is not labile in the presence of DTT but can be selectively cleaved by diethylenetriamine (DETA) and heat. In some embodiments, the linkers L1 and L2 can further comprise a labile bond that is a carbamate linkage, and not comprise a disulfide linkage. An exemplary labile linker comprising a carbamate group and methods of cleaving the carbamate and use in the cell-bead based methods of present disclosure are further described in the Examples.

Figure 34A:
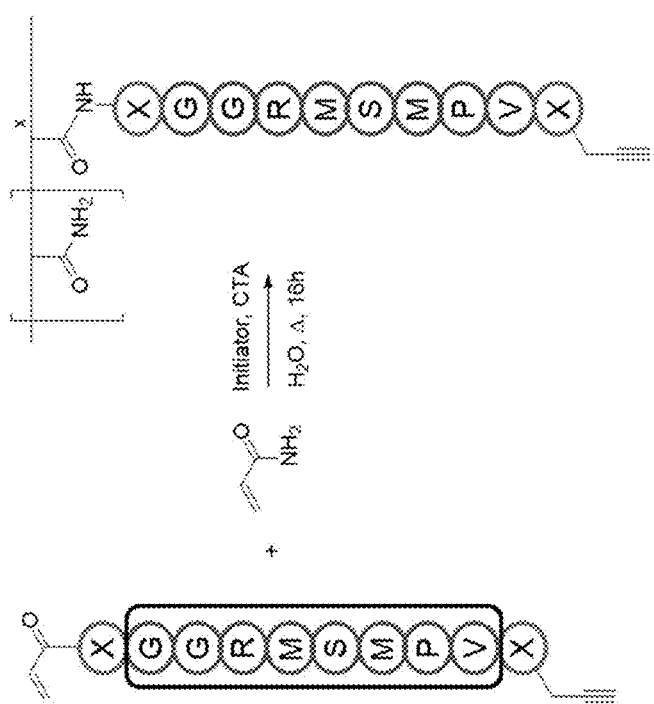
FIG. 34A shows an exemplary propargyl-polypeptide linker that can form a protease cleavable crosslink via click chemistry.

In some cases, the linkers L1 and L2 can further comprise a labile bond that is an enzymatically labile bond. For example, the linkers L1 and L2 can include a polypeptide with a sequence that is specifically cleaved by a particular protease. A linker comprising a specific polypeptide sequence with a terminal propargyl moiety can be incorporated into a polymer as shown in FIG. 34A. The propargyl For example, HRV 3C protease is a highly specific protease that cleaves between the Q and G residues of the "3C" polypeptide cleavage tag LEVLFQGP and is commercially available "PreScission protease" or "PSP." Another exemplary highly specific protease is enterokinase. Enterokinase is an intestinal enzyme normally involved in the protease cleavage of trypsin that specifically cleaves the peptide linkage after the K of the "EKT" recognition sequence, DDDDK. Similarly, as noted above, Type II collagenase specifically cleaves the peptide linkages between M and S in the sequence GGRMSMPV.

In some embodiments, the linker L1 and L2 can comprise a peptide linkage selectively cleavable by a protease. In some embodiments, the linker L1 and L2 can comprise a polypeptide comprising a peptide linkage selectively cleavable by a protease, optionally wherein the polypeptide has a sequence selected from GGRMSMPV, LEVLFQGP, and DDDDK. In some embodiments, the protease is selected from HRV 3C protease, enterokinase, and Type II collagenase.

As described elsewhere herein, a wide range of click chemistry reactions can be used in generating the polymers for use in the compositions and methods of the present disclosure. The useful click-chemistry reactions include the well-known copper-catalyzed reactions, such as CuAAC, as well as copper free click chemistry reactions. Accordingly, the moieties CL1 and CL2 can comprise any pair of chemical groups that undergo a click chemistry reaction. In some cases, one of the click chemistry moieties (CL1 or CL2) comprises an azide while the other comprises an alkyne. In some cases, one of the click chemistry moieties (CL1 or CL2) comprises an azide, while the other comprises a dibenzocyclooctyne (DBCO) group.

Both the azide-alkyne CuAAC reaction and the strain-promoted Cu free azide-DBCO reaction result in a click chemistry linkage comprising a 1,2,3-triazole moiety. However, as described elsewhere herein, the present disclosure also contemplates gel compositions and methods of making them wherein the linkers and associated click chemistry reactions for a linkage that does not comprise a 1,2,3-triazole. Such alternative click chemistry reactions and resulting linkages are well-known in the art. See e.g., Madl and Heilshorn, "Bioorthogonal Strategies for Engineering Extracellular Matrices," *Adv. Funct. Mater.* 2018, 28: 1706046, which is hereby incorporated by reference herein. Accordingly, in some cases, it is contemplated that the click chemistry reaction is an Inverse-electron demand Diels-Alder reaction wherein one of the click chemistry moieties (CL1 or CL2) comprises a tetrazine group, while the other group comprises a trans-cyclooctene (TCO) group or a norbonene group. In both cases, the use of tetrazine with either TCO or norbonene, the click chemistry reaction results in a linkage comprising a dihydropyridazine group rather than a 1,2,3-triazole.

Other click chemistry moieties and reactions that do not result in a 1,2,3-triazole but can be used in the gel compositions and methods of making them described herein include the furan-maleimide Diels-Alder reaction. Accordingly, in some embodiments, one of the click chemistry moieties (CL1 or CL2) comprises a furan moiety and the other a maleimide moiety.

In some cases, the integers n and m are chosen based on the properties of the polymers C and E produced. Such properties can include viscosity of the polymers before/after crosslinking, stability, pore sizes of the hydrogels formed, gelation rate, purity, purification procedures, compatibility of the click chemistry moieties with the polymerization conditions, procedures required to remove the initiators, etc.

Click Chemistry Conditions

As shown in FIG. 8, in some embodiments, a copper (II) species (reagent 822) is present in the oil phase outside the discrete droplets which comprise polymers to be cross-linked. However, in these embodiments, copper (I) species (reagent 824) is the catalyst to enable the click chemistry reaction inside the discrete droplets. In these instances, the copper (II) species initially existing in the outside oil phase can be exchanged into the aqueous phase inside the discrete droplets, and then reduced by a reductant (e.g., sodium ascorbate) in the aqueous phase to produce the copper (I) species in the aqueous phase inside the discrete droplet.

In some cases, the exchange process can be shown in Scheme 2. To form the copper (II) species in the oil phase, the first step can be an exchange reaction between copper (II) acetate salt and a fluorinated carboxylic acid denoted as Krytox-COOH, which comprises a perfluorinated alkyl chain to make the compound/complex a stable suspension in perfluorinated oil phase and an acidic carboxylic group to complex the copper (II). A perfluorinated compound or polymer, such as a poly(perfluoro-propyleneoxide) can be the type of compounds with a name of KRYTOX® and produced by DuPont.

Then the Krytox-COO⁻ complexed copper (II) salt can further combine with a perfluorinated surfactant Krytox-PEG-Krytox to form an emulsion droplet of copper (II) inside the aqueous phase of the droplet. As to the composition of the droplet thus formed, the surfactant Krytox-PEG-Krytox remain at the interface of the aqueous phase (inside) and the perfluorinated oil phase (outside) with the PEG component of the surfactant facing the inside aqueous phase and the perfluorinated arms pointing toward the outside oil phase. In this way, an oil-phase suspension of copper (II) species is formed and the oil-phase suspension copper (II) species is stable in the oil phase during the time of the click chemistry reactions. Furthermore, naked copper (II) species and/or the oil-phase suspension copper (II) species can be removed by filtration when desired, for example, before or after the click chemistry reaction is completed.

In some cases, the order of mixing the above reagents (copper (II) acetate, Krytox-COOH, and surfactant Krytox-PEG-Krytox) can be important. For example, direct mixing of all three components may not afford the desired suspension of copper (II) species in the oil phase. A stepwise procedure of mixing the copper (II) acetate and Krytox-COOH first, followed by the addition of the surfactant, together with stirring/mixing, etc., can produce the desired suspension.

Scheme 2.

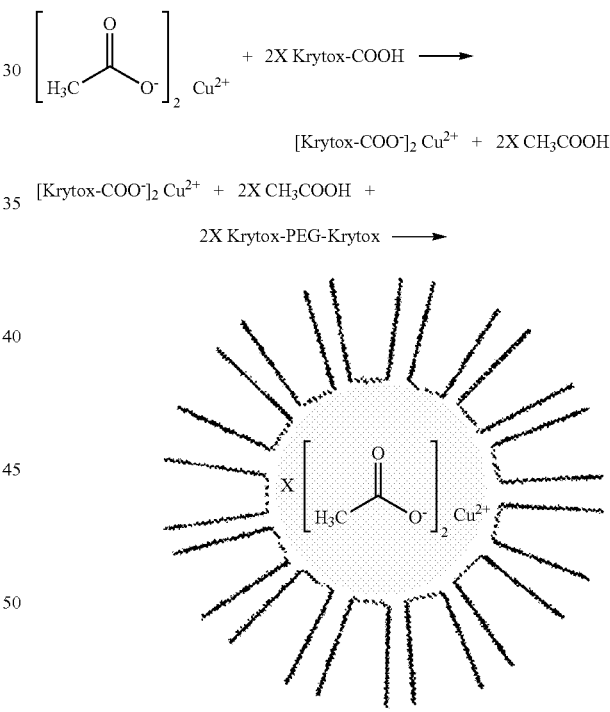

A fluorosurfactant having two fluorophilic tails and one hydrophilic head group (Formula I, hereinafter "tri-block surfactant") can reduce the coalescence of emulsion droplets and provide stability for emulsion systems, including, for example, gel bead-in-emulsion systems. In addition, a fluorosurfactant having one fluorophilic tail and one hydrophilic head group (Formula II, hereinafter "di-block surfactant" or "di-block copolymer") may also be used to provide stability for emulsion systems. Both n and m are integers greater than 1. Krytox-PEG-Krytox is an example of tri-block surfactant.

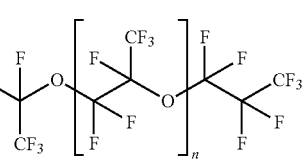

Formula I

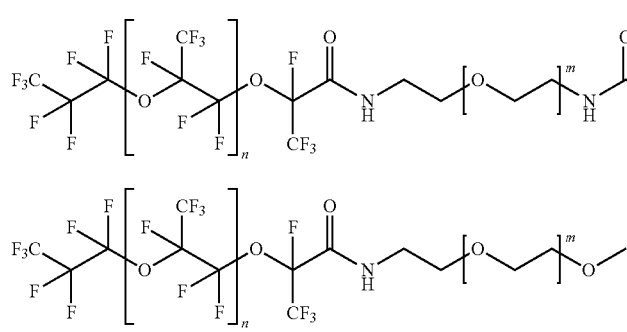

Formula II

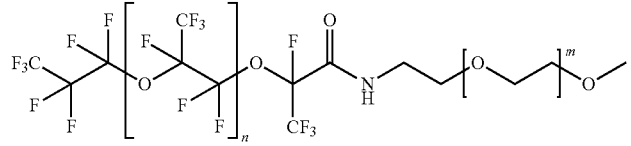

The second step can be the transport/phase transfer of the dissolved copper (II) species into droplets containing polymers to be crosslinked. Various factor can influence the transport/phase transfer, including, but not limited to, the concentration of respective ligands (e.g., THPTA or TBTA) in the oil phase and/or the aqueous phase, other aqueous components in the aqueous phase (e.g., surfactant, magnetic particles, solvents such as water, surfactants such as SYN-PERONIC® F-108, the type and quantity of the reducing agent used (disulfide such as dithiothreitol (DTT) or sodium ascorbate, polymers, and the v/v ratio between the oil phase and the aqueous phase during preparation).

The third step can be the reduction of copper (II) species to copper (I) species inside the aqueous phase of the droplet. The reducing reagent, such as, for example, sodium ascorbate, can be chosen based on its chemical properties as a reducing agent and its compatibility with other parts of the polymers and/or linker groups and/or other reagents that are present inside the aqueous phase of the droplet. For example, when the linker groups (e.g., click chemistry moieties CL1 or CL2) comprise a disulfide bond, using DTT as the copper reducing agent may interfere with the integrity of the polymers or hydrogels because the disulfide bond within the linker groups can be cleaved during the reduction of copper (II) species, thereby preventing the desired hydrogels from being generated.

The fourth step can be the click chemistry reaction catalyzed by the copper (I) species inside the droplet. In some cases, there can be at least a pair of polymers bearing the two click chemistry moieties 818 and 820, respectively, inside the droplet for the click chemistry reaction to occur. In some cases, there can be multiple pairs of such polymers. The number of pairs of such polymers inside one droplet can be controlled during the droplet formation process depicted in FIG. 7. Because crosslinking is involved, there can be cases wherein one polymer crosslinks with more than one other polymers to form the hydrogels.

Factors that can be considered during the click chemistry step may include, but are not limited to, size of the droplets, length/numbers/types/ratio of polymers enclosed in each droplet, ratio of reducing agent to the copper (I)/copper(II) species inside the aqueous phase of the droplet, ratio of copper (I) species to the click chemistry moieties on the polymers, effect of the ligand (e.g., THPTA or TBTA), time and temperature of the reaction, whether there is external influence (e.g., shaking or vortexing, microwaving, etc.), dissolved oxygen, and how to separate unwanted reagents/by-products after the click chemistry reaction is completed.

In some cases, the click chemistry reaction can be run under inert gas conditions. For example, the reaction can be performed under $N_2$ or Ar such that oxygen- or air-oxidation of copper (I) species is reduced. In some cases, the amount of reducing agent added is increased to counter the side-reaction of this oxygen- or air-oxidation of copper (I) species. In some cases, instead of starting from copper (II) species, a copper (I) species is added in the aqueous fluid as the catalyst for the azide-alkyne cycloaddition. In some cases, when a copper (I) species is the catalyst initially added in the aqueous fluid for the azide-alkyne cycloaddition, an oxygen-free system is provided for the reaction.

In some cases, solvent exchange can be conducted to remove unwanted reagents from the hydrogels formed.

In some cases, further transformations can be performed with the hydrogels by adding additional reagents into or removing some reagents from the hydrogels.

In some cases, a biological sample (e.g., a cell or nucleus or a nucleic acid) is enclosed inside the pores of the hydrogel formed during the click chemistry reaction. In some cases, the biological sample can be modified or characterized inside the hydrogel by reacting the biological sample with reagents transported into the hydrogel (e.g., through the hydrogel pores).

In some cases, copper nanoparticles can be complexed to a cell which is enclosed inside a hydrogel. In these instances, the copper nanoparticles are used to catalyze a click chemistry reaction thereby forming the hydrogel. Copper nanoparticles may be used as an alternative to, or in addition to, copper (II) or copper (I) species. For example, cells may be complexed with copper nanoparticles prior to partitioning (e.g., into droplets). Cells comprising the copper nanoparticles are then partitioned (e.g., into droplets) with the click chemistry polymers described herein, thereby generating a cross-linked hydrogel. The use of cell-complexed copper nanoparticles may allow for selective gelation of a hydrogel, such that a click chemistry reaction is performed only in droplets comprising a copper-complexed cell.

In some cases, during the crosslinking reaction between crosslink precursors, the labile bond (e.g., disulfide bond) in the crosslink precursors or the crosslink thus formed remains intact (i.e., not broken). In some cases, about 55%, 60%, 65%, 70%, 75%, 80%, 85%, 90%, 95%, 96%, 97%, 98%, 99%, or greater of the labile bond can remain intact during the crosslinking reaction. In some cases, at least about 55%, 60%, 65%, 70%, 75%, 80%, 85%, 90%, 95%, 96%, 97%, 98%, 99%, or greater of the labile bond can remain intact during the crosslinking reaction.

In some case, the labile bond (e.g., disulfide bond) in the crosslinks can be broken by treating with a reagent (e.g., a reducing agent, such as DTT, TCEP, etc.) such that the biological sample enclosed inside the hydrogel is released and/or the pores of the hydrogel are expanded such that one or more reagents capable of reacting with the biological sample can now gain access to the biological sample.

Figure 9:
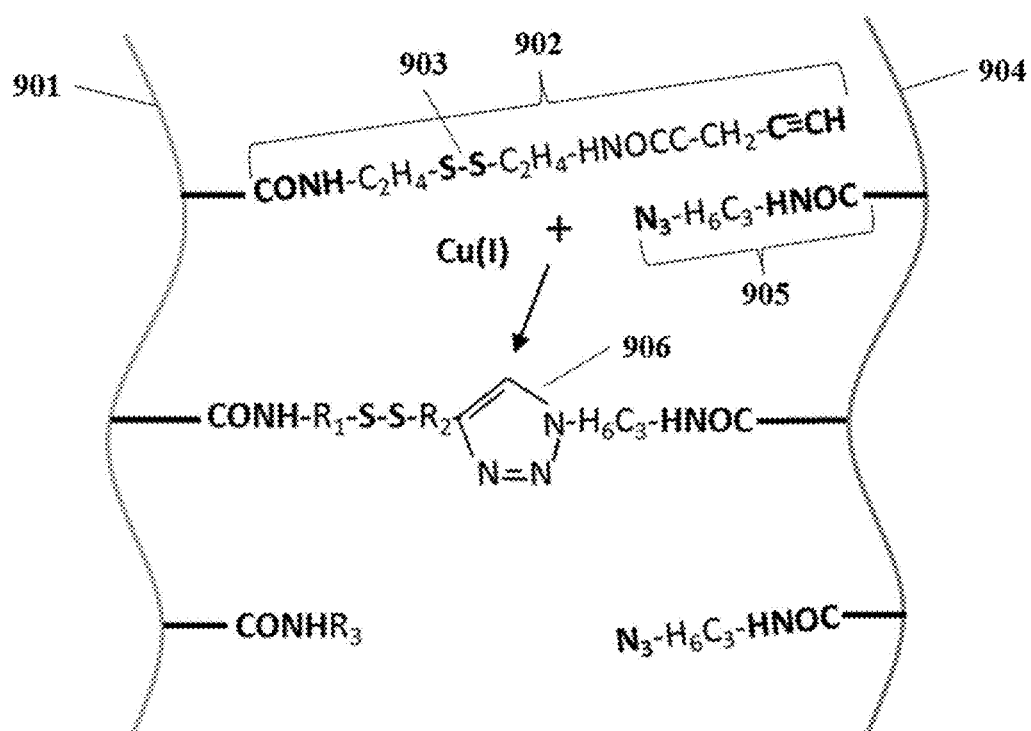
FIG. 9 shows an example method for generating a click chemistry polymer network.

FIG. 9 shows a schematic of an example hydrogel generated using click chemistry. A first co-polymer 901 comprises an alkyne moiety 902, and a second co-polymer 904 comprises an azide moiety 905. Alkyne moiety 902 may comprise a degradable linker (e.g., disulfide bond 903). Alternatively, or in addition, azide moiety 905 may comprise a degradable linker. Alkyne moiety 902 may react with azide moiety 905 in the presence of Cu(I) to generate an interchain linker comprising 1,2,3-triazole moiety 906.

Methods for Cell Bead Generation

Figure 10:
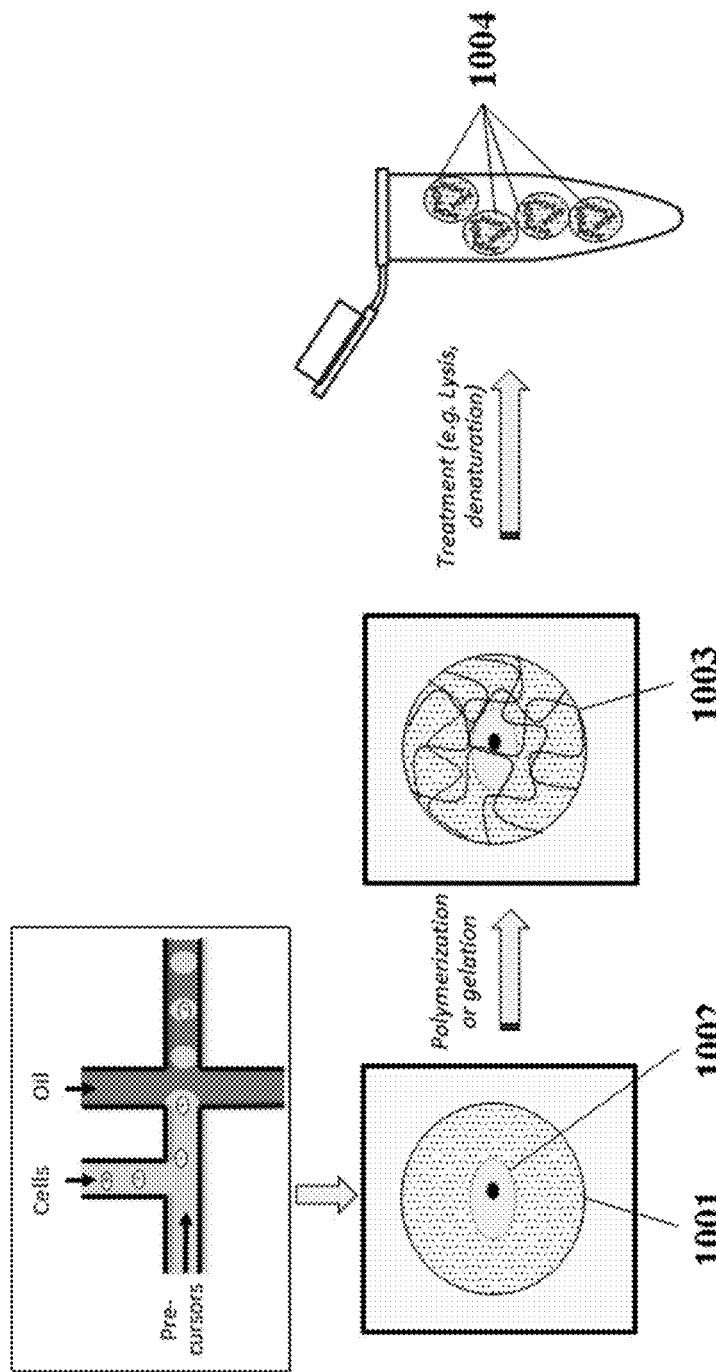
FIG. 10 illustrates an example method for generating a cell bead of the present disclosure.

Methods of the present disclosure may comprise generation of one or more cell beads comprising one or more of the polymers disclosed herein. FIG. 10 shows an example method for generating a cell bead. In this example, cells and polymer or gel precursors are mixed with an immiscible fluid (e.g., an oil), thereby generating a plurality of aqueous droplets, including droplet 1001 comprising cell 1002. Droplet 1001 may comprise a charged species, as described herein. Droplet 1001 is subjected to conditions sufficient for polymerization or gelation of the polymer or gel precursors to generate a cell bead 1003 comprising cell 1002. Gelation may comprise any of the gelation mechanisms and polymers described herein, including those utilizing a click chemistry reaction, as described elsewhere herein. In some instances, cell bead 1003 is subjected to treatment conditions sufficient to lyse cell 1002, releasing components of the cell into the cell bead. In other embodiments, cell 1002 is lysed in droplet 901 prior to polymerization or gelation of the polymer or gel precursors to generate cell bead 1003. In still other embodiments, cell 1002 is permeabilized before or after polymerization or gelation of the polymer or gel precursors. Cell beads are collected in an aqueous phase to generate a plurality of cell beads 1004. Cell beads may be stored for further processing. In some cases, charged species may be attached to the cell beads subsequent to polymerization or gelation of the polymer or gel precursor. For instance, polymer or gel precursors may comprise one or more functional groups that facilitate the attachment of the charged species subsequent to polymerization or gelation of the polymer or gel precursors. In other embodiments, the polymer or gel precursors comprise functional groups comprising the charged species, which are incorporated into the cell bead during polymerization or gelation of the polymer or gel precursors.

In an aspect, the present disclosure provides methods for generating a cell bead comprising a charged species. First, a partition may be generated comprising a cell from a plurality of cells, a polymeric or gel precursor, and a charged species. Next, the partition may be subjected to conditions sufficient to react the polymeric or gel precursor to generate a polymer or gel network comprising the cell or a derivative thereof and the charged species, thereby generating a cell bead. The partition may be subjected to conditions sufficient to polymerize or gel the polymeric or gel precursors. Conditions sufficient to polymerize or gel polymeric or gel precursors are described elsewhere herein. In some embodiments, the cell is lysed to release components of the cell into the cell bead. The cell may be lysed prior to polymerization or gelling of the polymeric or gel precursors, concurrently with polymerization or gelling of the polymeric or gel precursors, or subsequent to polymerization or gelling of the polymeric or gel precursors. In other embodiments, the cell in the cell bead is not lysed, but is permeabilized to allow access to components within the nucleus.

In another aspect, the present disclosure provides methods for generating a cell bead comprising a charged species. First, a partition may be generated comprising a nucleus isolated from a cell, a polymeric or gel precursor, and a charged species. Next, the partition may be subjected to conditions sufficient to react the polymeric or gel precursors to generate a polymer or gel network comprising the nucleus and the charged species, thereby generating a cell bead. The partition may be subjected to conditions sufficient to polymerize or gel the polymeric or gel precursors. Conditions sufficient to polymerize or gel polymeric or gel precursors are described elsewhere herein. For example, a copper catalyst may be used to catalyze a click chemistry reaction, thereby generating a hydrogel. In some embodiments, the nucleus is lysed to release components of the nucleus into the cell bead. The nucleus may be lysed prior to polymerizing or gelling the polymeric or gel precursors, concurrently with polymerizing or gelling the polymeric or gel precursors, or subsequent to polymerizing or gelling the polymeric or gel precursors. In other embodiments, the nucleus in the cell bead is not lysed, but is permeabilized to allow access to nuclear components within the nucleus.

A charged species may be a positively charged species. A positively charged species may be a reagent comprising a positive charge. A positively charged species may comprise trimethylammonium. A positively charged species may be (3-Acrylamidopropyl)-trimethylammonium. A charged species may be a negatively charged species. A negatively charged species may comprise phosphate. A charged species may be attached to the polymer or gel network. A charged species may be incorporated into a polymer or gel network during polymerization. A cell bead may comprise one or more chemical cross-linkers. A chemical cross-linker may be a disulfide bond. A charged species may be attached to one or more chemical cross-linkers. A derivative of a cell may be a component from a cell (e.g., DNA, RNA, protein, etc.). A method of generating a cell bead may comprise lysing a cell within a partition (e.g., a droplet) to release a component from the cell. A component may be a nucleic acid. A nucleic acid may be DNA (e.g., genomic DNA) or RNA (e.g., mRNA, siRNA). A component may be a protein. A component may be a negatively charged component, for example, DNA, RNA, or miRNA. A component may be a positively charged component, for example, a protein. A component from a cell may interact with a charged species. A component from a cell may be non-covalently attached to a charged species.

In some embodiments, a negatively charged component from or derived from a cell (e.g., DNA) interacts with a positively charged species (e.g., ((3-Acrylamidopropyl)-trimethylammonium) of the cell bead (e.g., a positively charged functional group of the cell bead polymers) via ionic interactions. In other embodiments, a positively charged component from or derived from a cell (e.g., a protein) interacts with a negatively charged species (e.g., phosphate) of the cell bead (e.g., a negatively charged functional group of the cell bead polymers) via ionic interactions. In still other embodiments, a negatively charged component from or derived from a cell (e.g., DNA) interacts with a positively charged species (e.g., ((3-Acrylamidopropyl)-trimethylammonium) of the cell bead (e.g., a positively charged functional group of the cell bead polymers) and a positively charged component from or derived from a cell (e.g., a protein) interacts with a negatively charged species (e.g., phosphate) of the cell bead (e.g., a negatively charged functional group of the cell bead polymers). Thus, one or more components from a cell may be capable of being retained within the cell bead, for example, due to electrostatic interactions with a charged species of a cell bead. A component from a cell may be capable of being retained within the cell bead for about 1 hour, about 2 hours, about 3 hours, about 4 hours, about 5 hours, about 6 hours, about 12 hours, about 24 hours, about 48 hours, about 72 hours, or more. A component from a cell may be capable of being retained within the cell bead for at least 1 hour, at least 2 hours, at least 3 hours, at least 4 hours, at least 5 hours, at least 6 hours, at least 12 hours, at least 24 hours, at least 48 hours, at least 72 hours, or more. A component from a cell may be capable of being retained within the cell bead for at most 1 hour, at most 2 hours, at most 3 hours, at most 4 hours, at most 5 hours, at most 6 hours, at most 12 hours, at most 24 hours, at most 48 hours, or at most 72 hours.

In an aspect, the present disclosure provides methods for generating a cell bead comprising an electrically charged polymer or gel network (e.g., a cell bead comprising a charged species). First, a partition may be generated comprising a cell from a plurality of cells and a polymeric or gel precursor. Next, the partition may be subjected to conditions sufficient to react said electrically charged polymeric or gel precursor to generate an electrically charged polymer or gel network comprising the cell or a derivative thereof, thereby providing the cell bead comprising the charged species. The reaction may be such that the net charge on the polymer or gel precursor is changed, thereby generating an electrically charged polymer or gel network. The reaction may be such that the net charge on the polymer or gel network is changed, thereby generating an electrically charged polymer or gel network.

The polymer or gel precursor may be positively charged. The polymer or gel precursor may comprise chitosan. The polymer or gel precursor may comprise polyethyleneimine (PEI). The polymer or gel precursor may be negatively charged. The polymer or gel precursor may comprise alginate. A derivative of a cell may be a component from a cell (e.g., DNA, RNA, protein, etc.). A method of generating a cell bead may comprise lysing a cell within a partition (e.g., a droplet) to release a component from the cell. A component may be a nucleic acid. A nucleic acid may be DNA (e.g., genomic DNA) or RNA (e.g., mRNA, siRNA). A component may be a protein. A component may be a negatively charged component, for example, DNA, RNA, or miRNA. A component may be a positively charged component, for example, a protein. A component from a cell may interact with the electrically charged polymer or gel network. A component from a cell may be non-covalently attached to the polymer or gel network of a cell bead comprising a charged species. In some embodiments, a negatively charged component from or derived from a cell (e.g., DNA) interacts with a positively charged species of the cell bead (e.g., a positive charged polymer or gel network) via ionic interactions. In other embodiments, a positively charged component from or derived from a cell (e.g., a protein) interacts with a negatively charged species of the cell bead (e.g., a negatively charged polymer or gel network) via ionic interactions. In still other embodiments, a negatively charged component from or derived from a cell (e.g., DNA) interacts with a positively charged species of the cell bead (e.g., a positive charged polymer or gel network) and a positively charged component from or derived from a cell (e.g., a protein) interacts with a negatively charged species of the cell bead (e.g., a negatively charged polymer or gel network). Thus, one or more components from a cell may be capable of being retained within the cell bead, for example, due to electrostatic interactions with a charged species of a cell bead. A component from a cell may be capable of being retained within the cell bead, for example, due to interactions with an electrically charged polymer or gel network. A component from a cell may be capable of being retained within the cell bead for about 1 hour, about 2 hours, about 3 hours, about 4 hours, about 5 hours, about 6 hours, about 12 hours, about 24 hours, about 48 hours, about 72 hours, or more. A component from a cell may be capable of being retained within the cell bead for at least 1 hour, at least 2 hours, at least 3 hours, at least 4 hours, at least 5 hours, at least 6 hours, at least 12 hours, at least 24 hours, at least 48 hours, at least 72 hours, or more. A component from a cell may be capable of being retained within the cell bead for at most 1 hour, at most 2 hours, at most 3 hours, at most 4 hours, at most 5 hours, at most 6 hours, at most 12 hours, at most 24 hours, at most 48 hours, or at most 72 hours.

In an aspect, the present disclosure provides methods for generating a cell bead comprising a charged species. First, a partition may be generated comprising a cell from a plurality of cells and a polymeric or gel precursor. Next, the partition may be subjected to conditions sufficient to react the polymeric or gel precursor to generate a polymer or gel network comprising the cell or a derivative thereof. Next, a charged species may be coupled to the polymer or gel network, thereby providing the cell bead comprising the charged species. The partition may be subjected to conditions sufficient to polymerize or gel the polymeric or gel precursors. Conditions sufficient to polymerize or gel polymeric or gel precursors are described elsewhere herein. For example, a copper catalyst may be used to catalyze a click chemistry reaction, thereby generating a hydrogel. In some cases, the cell is lysed to release cellular components. The cell may be lysed prior to polymerizing or gelling the polymeric or gel precursors, concurrently with polymerizing or gelling the polymeric or gel precursors, or subsequent to polymerizing or gelling the polymeric or gel precursors.

A polymer or gel network can be a degradable polymer or gel network, as described herein, such that a cell bead is a degradable cell bead. Any number of cell beads may be generated by generating a plurality of partitions. In some cases, about 1, about 2, about 3, about 4, about 5, about 10, about 50, about 100, about 500, about 1000, about 5000, about 10000, about 20000, about 50000, about 100000, or more cell beads are generated, thereby generating a plurality of cell beads. A cell bead may be partitioned together with a barcode bead (e.g., a gel bead) for analysis of a cell or components thereof.

Compositions for Cellular Analysis

Disclosed herein are compositions comprising a cell bead comprising a polymerized or cross-linked polymer network comprising a cell or a lysed cell generated from the cell, wherein the polymerized or cross-linked polymer network is electrically charged. The cell bead may comprise a component from a cell. A component may be a nucleic acid. A nucleic acid may be DNA (e.g., genomic DNA) or RNA (e.g., mRNA, miRNA). A component may be a protein. The polymer network may be positively charged. The polymer network may comprise chitosan. The polymer network may comprise PEI. The polymer network may be negatively charged. The polymer network may comprise alginate. A component from a cell may be capable of being retained within the cell bead for about 1 hour, about 2 hours, about 3 hours, about 4 hours, about 5 hours, about 6 hours, about 12 hours, about 24 hours, about 48 hours, about 72 hours, or more. A component from a cell may be capable of being retained within the cell bead for at least 1 hour, at least 2 hours, at least 3 hours, at least 4 hours, at least 5 hours, at least 6 hours, at least 12 hours, at least 24 hours, at least 48 hours, at least 72 hours, or more. A component from a cell may be capable of being retained within the cell bead for at most 1 hour, at most 2 hours, at most 3 hours, at most 4 hours, at most 5 hours, at most 6 hours, at most 12 hours, at most 24 hours, at most 48 hours, or at most 72 hours.

Also disclosed herein are compositions comprising a cell bead comprising a polymerized or cross-linked polymer network comprising a cell or a lysed cell generated from the cell and a charged species. The cell bead may comprise a component from the cell. A component may be a nucleic acid. A nucleic acid may be DNA (e.g., genomic DNA) or RNA (e.g., mRNA, miRNA). A component may be a protein. The charged species may be positively charged. The charged species may comprise trimethylammonium. The charged species may be (2-Aminoethyl)trimethylammonium. The charged species may be (3-Acrylamidopropyl) trimethylammonium. The charged species may be negatively charged. The charged species may comprise phosphate. A component from a cell may be capable of being retained within the cell bead for about 1 hour, about 2 hours, about 3 hours, about 4 hours, about 5 hours, about 6 hours, about 12 hours, about 24 hours, about 48 hours, about 72 hours, or more. A component from a cell may be capable of being retained within the cell bead for at least 1 hour, at least 2 hours, at least 3 hours, at least 4 hours, at least 5 hours, at least 6 hours, at least 12 hours, at least 24 hours, at least 48 hours, at least 72 hours, or more. A component from a cell may be capable of being retained within the cell bead for at most 1 hour, at most 2 hours, at most 3 hours, at most 4 hours, at most 5 hours, at most 6 hours, at most 12 hours, at most 24 hours, at most 48 hours, or at most 72 hours.

FIG. 11A shows example cell beads of the present disclosure comprising positively charged species attached to a polymer or gel network. Cell beads 1101 comprise positively charged species 1103 attached to the polymer or gel network. Cell Beads 1101 comprising positively charged species 1103 can be generated using any of the methods disclosed herein, including polymerization or gelling of electrically charged polymeric or gel precursors (e.g., gel precursors comprising charged functional groups). Cell beads 1101 also comprise a negatively charged cell component 1102 (e.g., nucleic acid, such as DNA) from a single cell. Positively charged species 1103 interacts with the negatively charged cell component 1102, thereby retaining the negatively charged cell component 1102 in the cell beads 1101. Cell beads 1101 are stored with little to no diffusion of the negatively charged cell component 1102 out of the cell beads over time.

FIG. 11B shows an example cell bead of the present disclosure comprising negatively charged species attached to a polymer or gel network. Cell beads 1111 comprise negatively charged species 1113 attached to the polymer or gel network. Cell Beads 1111 comprising negatively charged species 1113 can be generated using any of the methods disclosed herein, including polymerization or gelling of electrically charged polymeric or gel precursors (e.g., gel precursors comprising charged functional groups). Cell beads 1111 also comprise a positively charged cell component 1112 (e.g., a protein or polypeptide comprising a region of net positive charge) from a single cell. Negatively charged species 1113 interact with the positively charged cell component 1112, thereby retaining the positively charged cell component 1112 in the cell beads 1111. Cell beads 1111 are stored with little to no diffusion of the positively charged cell component 1112 out of the cell beads.

Figure 12A:
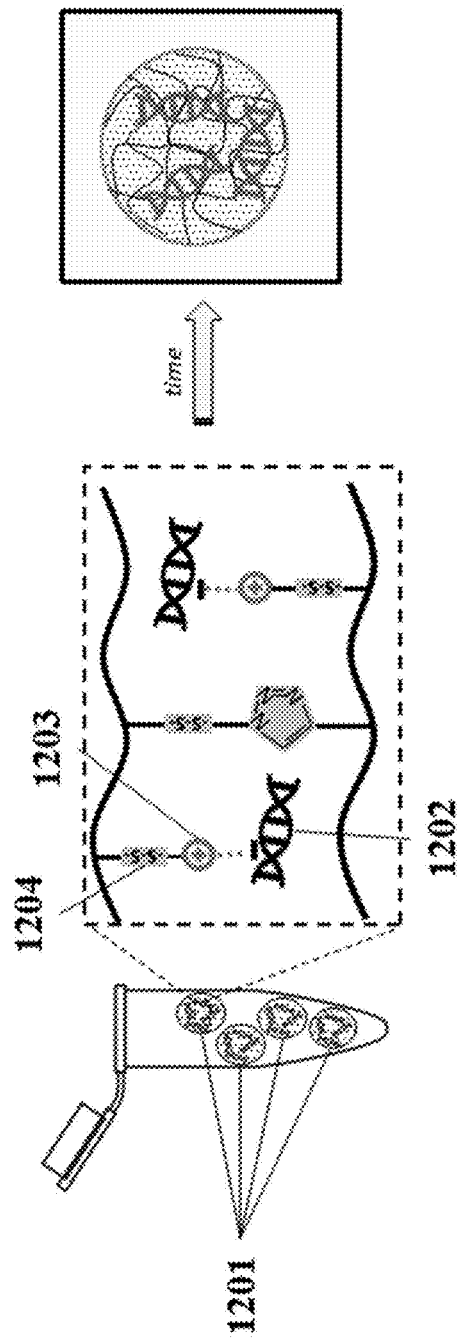
FIGS. 12A-B show an additional example charged hydrogel polymer network.

FIG. 12A shows example cell beads of the present disclosure comprising positively charged species attached to releasable chemical cross-linkers. Cell beads 1201 comprise positively charged species 1203 attached to releasable chemical cross-linkers 1204 (e.g., disulfide bonds). Cell beads 1201 comprising positively charged species 1203 attached to releasable chemical cross-linkers 1204 can be generated using any of the methods disclosed herein, including polymerization or gelling of gel precursors comprising charged functional groups attached to releasable chemical cross-linkers. In other embodiments, cell beads 1201 comprising positively charged species 1203 attached to releasable chemical cross-linkers 1204 are generated by polymerization or gelling of gel precursors, followed by functionalization of the polymerized or gelled cell bead with charged functional groups using a cross-linking agent. Cell beads 1201 also comprise a negatively charged cell component 1202 (e.g., nucleic acid, such as DNA) from a single cell. Positively charged species 1203 interacts with the negatively charged cell component 1202, thereby retaining the negatively charged cell component 1202 in the cell beads 1201. Cell beads 1201 are stored with little to no diffusion of the negatively charged cell component 1202 out of the cell beads over time.

Figure 12B:
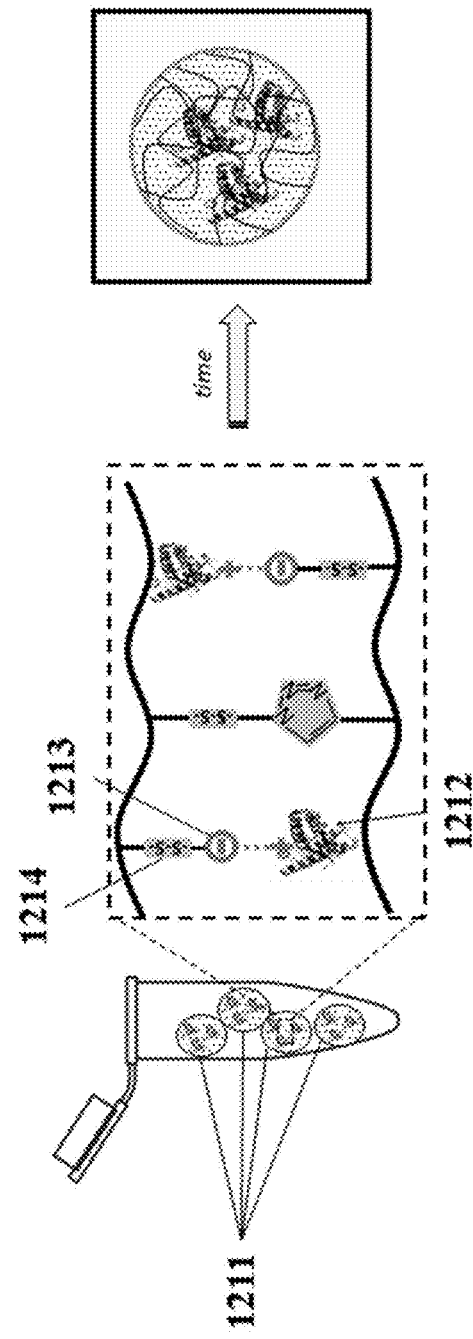

FIG. 12B shows an example of a cell bead of the present disclosure comprising negatively charged species attached to releasable chemical cross-linkers. Cell beads 1211 comprise negatively charged species 1213 attached to releasable chemical cross-linkers 1204 (e.g., disulfide bonds). Cell beads 1211 comprising negatively charged species 1213 attached to releasable chemical cross-linkers 1214 can be generated using any of the methods disclosed herein, including polymerization or gelling of gel precursors comprising charged functional groups attached to releasable chemical cross-linkers. In other embodiments, cell beads 1211 comprising negatively charged species 1213 attached to releasable chemical cross-linkers 1214 are generated by polymerization or gelling of gel precursors, followed by functionalization of the polymerized or gelled cell bead with charged functional groups using a cross-linking agent. Cell beads 1211 also comprise a positively charged cell component 1212 (e.g., a protein or polypeptide comprising a region of net positive charge) from a single cell. Negatively charged species 1213 interacts with a positively charged cell component 1212, thereby retaining the positively charged cell component 1212 in the cell beads 1211. Cell beads 1211 are stored with little to no diffusion of positively charged cell component 1212 out of the cell beads over time.

The charged cell beads and charged hydrogels of the present disclosure (e.g., FIG. 11A-B, FIG. 12A-B) can also comprise any of the crosslinked polymers (e.g., click chemistry polymers, such as in FIG. 8) as disclosed elsewhere herein.

Cell Beads

In an aspect, the present disclosure provides methods and systems for the generation of cell beads, which may be useful in processing different components from single cells. Cell beads may be generated by methods as described herein, for example by polymerization of molecular precursors (e.g., polymer or gel precursors) in a partition comprising a cell or constituents from a cell. Cell beads can comprise one or more different types of components from a cell, including, for example, DNA (e.g., gDNA, chromatin, etc.), RNA (e.g., mRNA, miRNA), proteins, and/or metabolites. Components may be comprised in and/or attached to cell beads. Cell beads can be generated by encapsulating a cell in a polymer or gel matrix and lysing the cell in the gel or polymer matrix, lysing the cell while it is being encapsulated in the polymer or gel matrix, or lysing the cell so that its constituents are encapsulated in the polymer or gel matrix. The polymer or gel matrix may comprise one or more charged species configured to interact with a component from a cell (e.g., DNA, RNA, proteins, etc.).

The partition used in generating a cell bead may comprise one or more reagents for conducting one or more reactions. Species may include, for example, reagents for a nucleic acid amplification or extension reaction (e.g., primers, polymerases, nucleotides, co-factors (e.g., ionic co-factors), buffers, etc.) including those described herein, reagents for enzymatic reactions (e.g., enzymes, co-factors, substrates, buffers, etc.), reagents for nucleic acid modification reactions, such as polymerization, ligation, or digestion, and/or reagents for template preparation.

Reagents may comprise reagents for minimizing damage of nucleic acids resulting from a click chemistry reaction. For example, a radical scavenger may be added to a partition, thereby reducing the risk of damage to nucleic acids caused by free radicals generated during a click chemistry reaction. In some cases, the radical scavenger comprises dimethyl sulfoxide (DMSO). DMSO may be added to a partition used in generating a cell bead at a sufficient concentration for preventing nucleic acid damage. In some embodiments, DMSO is added to a partition at an amount of at least about 1%, about 2%, about 3%, about 4%, about 5%, about 6%, about 7%, about 8%, about 9%, about 10%, or greater.

One or more reagents within a partition may be attached to precursors (e.g., polymer or gel precursors). Reagents may be covalently attached to precursors. Reagents may be reversibly or irreversible attached to precursors. Reagents may be attached to precursors via an acrydite moiety.

In some cases, oligonucleotides may be attached to the precursors. Oligonucleotides attached to precursors may be useful in, for example, capturing RNA and/or performing a reverse transcription reaction. Oligonucleotides may comprise a poly-T sequence or a poly-U sequence (e.g., may be a poly-T primer). In some embodiments, a poly-T sequence is used to hybridize to a poly-A sequence, for example, from mRNA of a cell. In some embodiments, a poly-U sequence is used to hybridize to a poly-A sequence, for example, from mRNA of a cell.

Figure 35:
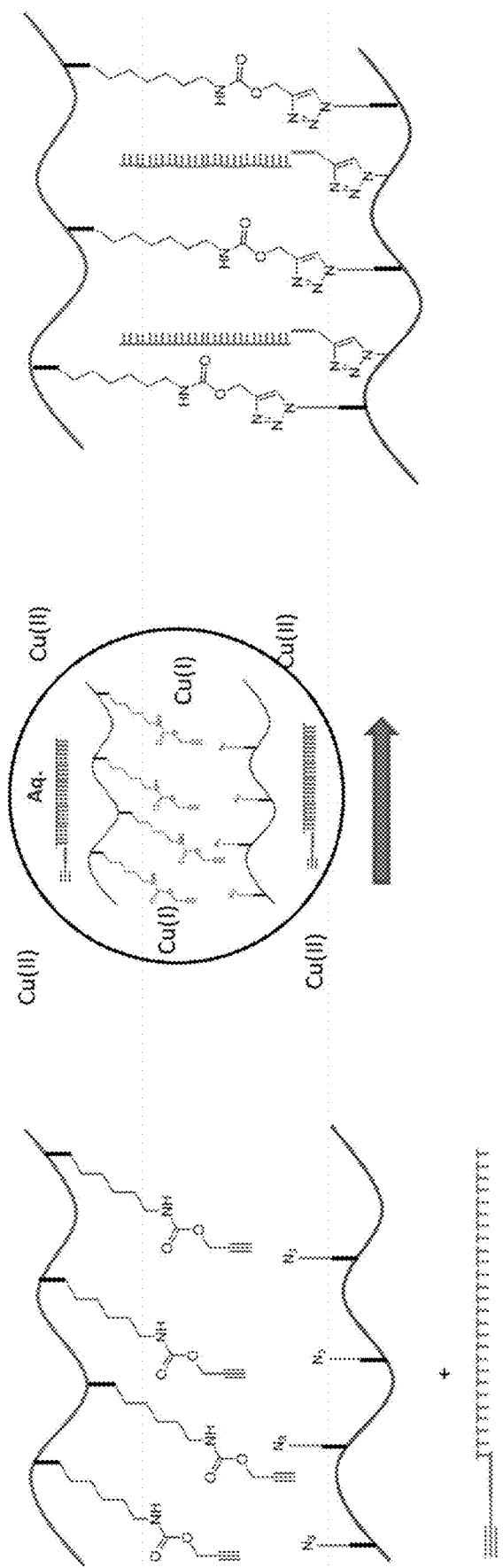
FIG. 35 shows an exemplary reaction forming via click chemistry crosslinked polymers with one of the polymers modified with a poly-T oligonucleotide capture reagent attached via click chemistry.

In some cases, an oligonucleotide, such as a poly-T sequence, can be attached to a precursor (e.g., polymer) via an irreversible click chemistry reaction. In some embodiments, this click chemistry attachment of an oligonucleotide can be carried out during the crosslinking of the polymers that results in a gel matrix. For example, as depicted in FIG. 35, a propargylated poly-T oligonucleotide introduced into an emulsion droplet together with the polymers modified with azide and alkyne click chemistry groups is attached via CuAAC click chemistry resulting in a 1,2,3-triazole linkage with some of the azide-modified linker sites of the azide-modified polymer. The other sites form crosslinks with the alkyne-modified polymers resulting in a gel matrix comprising covalently attached poly-T reagents capable of capturing polyadenylated RNA transcripts.

A partition used in generating a cell bead may comprise one or more particles (e.g., magnetic particles). One or more reagents within a partition may be attached to the particle. Reagents may be covalently attached to the particle. Reagents may be reversibly or irreversibly attached to the particle. Regents may be attached to the particle via an acrydite moiety. In some cases, oligonucleotides may be attached to the particle. Oligonucleotides attached to the particle may be useful in, for example, capturing RNA and performing a reverse transcription reaction. In some embodiments, the particles (which are optionally magnetic particles) comprise oligonucleotides attached thereto that comprise a poly-T sequence capable of hybridizing to a poly-A sequence, for example, from mRNA of a cell.

A cell within a partition may be lysed as described herein, thereby releasing constituents from the cell into the partition. Constituents may include multiple types of cellular components, including proteins, metabolites, and/or nucleic acid molecules (e.g., DNA, RNA (e.g. messenger RNA), etc.). Alternatively, or in addition, a cell within a partition may by permeabilized. Permeabilization may allow for transfer of certain reagents, species, constituents, etc. into and/or out of a cell with or without complete cellular lysis. In some embodiments, the cell is lysed or permeabilized prior to the polymerization or gelling of the cell bead. In other embodiments, the cell is lysed or permeabilized concurrent with the polymerization or gelling of the cell bead. In some embodiments, the cell is lysed or permeabilized subsequent to the polymerization or gelling of the cell bead. In still other embodiments, the cell is not lysed or permeabilized while in the cell bead.

Reagents can be included within a partition, including reagents attached to precursors, particles, etc., and may be used to perform one or more reactions on the cell or constituents from or derived from a cell. A reaction may be, for example, amplification, reverse transcription, or deamination reaction. In some embodiments, the one or more reactions are performed prior to the polymerization or gelling of the cell bead. In some embodiments, the one or more reactions are performed concurrent with the polymerization or gelling of the cell bead. In some embodiments, the one or more reactions are performed subsequent to the polymerization or gelling of the cell bead. In some cases, oligonucleotides (e.g., primers) are used to perform a reverse transcription reaction on messenger RNA from a cell, thereby generating complementary DNA (cDNA). Reverse transcription may comprise the addition of additional nucleotides, e.g., a polynucleotide such as polyC, to the cDNA. In some cases, template switching may be performed to further extend the cDNA. Template switching may append one or more additional sequences to the cDNA. Additional sequences may, in some cases, be used to facilitate nucleic acid extension/amplification and/or barcoding, as described herein. cDNA may be attached to precursors and/or particles. In some cases, oligonucleotides are used to capture messenger RNA from a cell, (e.g., via hybridization) prior to generation of a cell bead.

Figure 13:
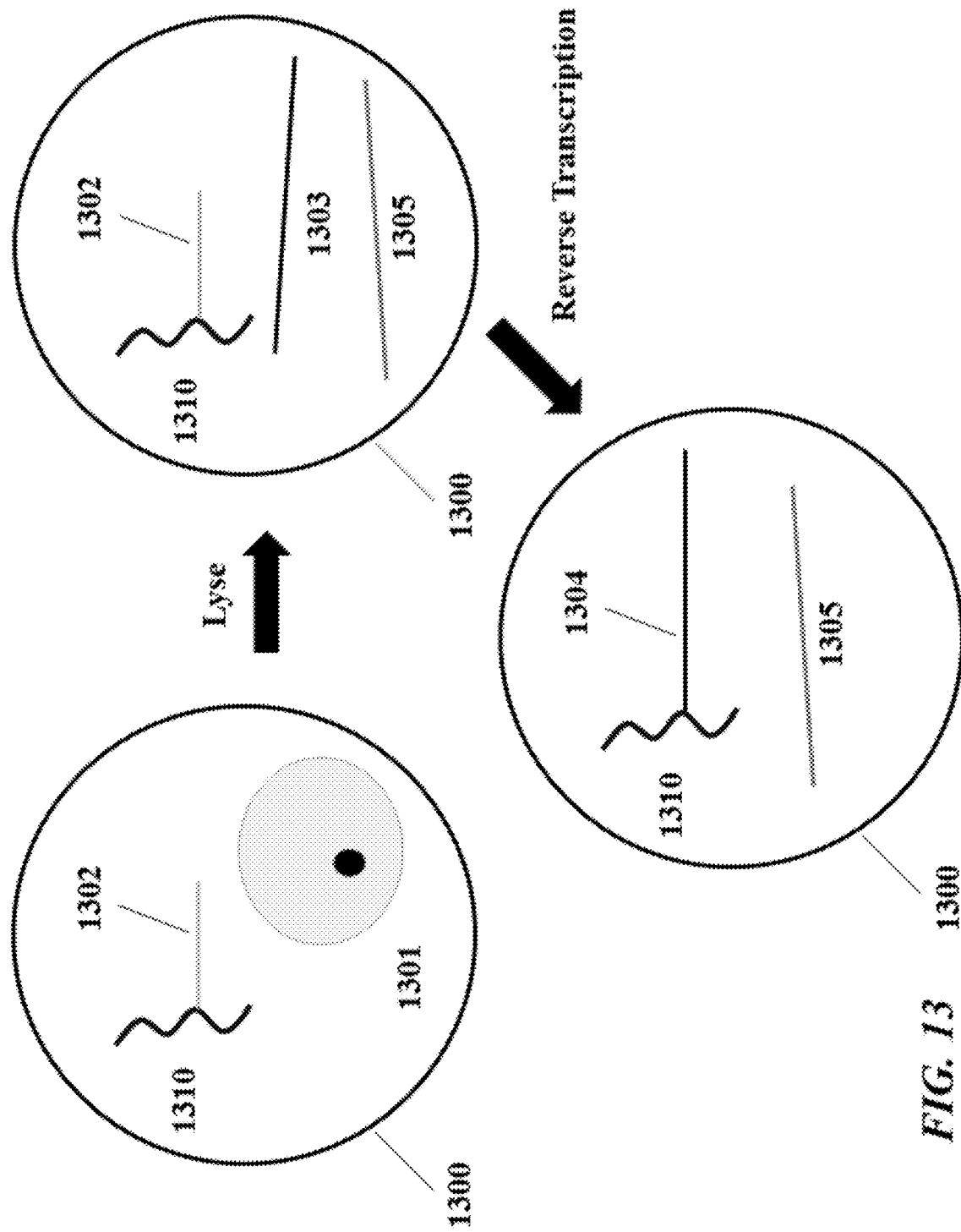
FIG. 13 illustrates an example process for generating droplets comprising constituents from a cell.

FIG. 13 illustrates an example method for generating cDNA from cellular mRNA and attaching the cDNA to a polymeric precursor. A partition 1300 (e.g., an aqueous droplet in an emulsion) may comprise a cell 1301 and an oligonucleotide 1302 attached to a polymeric precursor 1310. In some embodiments, the oligonucleotide 1302 comprises a poly-T sequence, random N-mer, targeted capture/primer sequence, and/or any other additional sequences, such as the functional sequences described elsewhere herein. In some instances, the partition 1300 further comprises one or more reagents, such as reagents for performing one or more reactions on one or more components of the cell (e.g., a reverse transcriptase enzyme, buffer, cofactors, etc.) or reagents for polymerizing or gelling the polymeric precursor 1310. The partition 1300 can also optionally comprise a template switching oligonucleotide (not shown). Cell 1301 is lysed or permeabilized, thereby releasing or otherwise allowing access to multiple types of cellular constituents including messenger RNA (mRNA) 1303 and genomic DNA (gDNA) 1305. Oligonucleotide 1302 may be used to perform reverse transcription (RT) of the mRNA, thereby generating complementary DNA (cDNA) 1304 attached to polymeric precursor 1310. In some instances, a template switching reaction can be performed using the template switching oligonucleotide to, e.g., append additional sequences to the cDNA. The polymeric precursor 1310 comprising the cDNA can then be polymerized or gelled to generate a cell bead comprising cDNA 1304 and gDNA 1305. In some embodiments, the polymeric precursor 1310 is polymerized or gelled to form a cell bead comprising mRNA 1303 (which may be hybridized to oligonucleotide 1302) and gDNA 1305 and cDNA 1304 is generated in the cell bead. In some embodiments, the oligonucleotide 1302 is releasably attached to the gel precursor 1310 via a labile bond.

Figure 14:
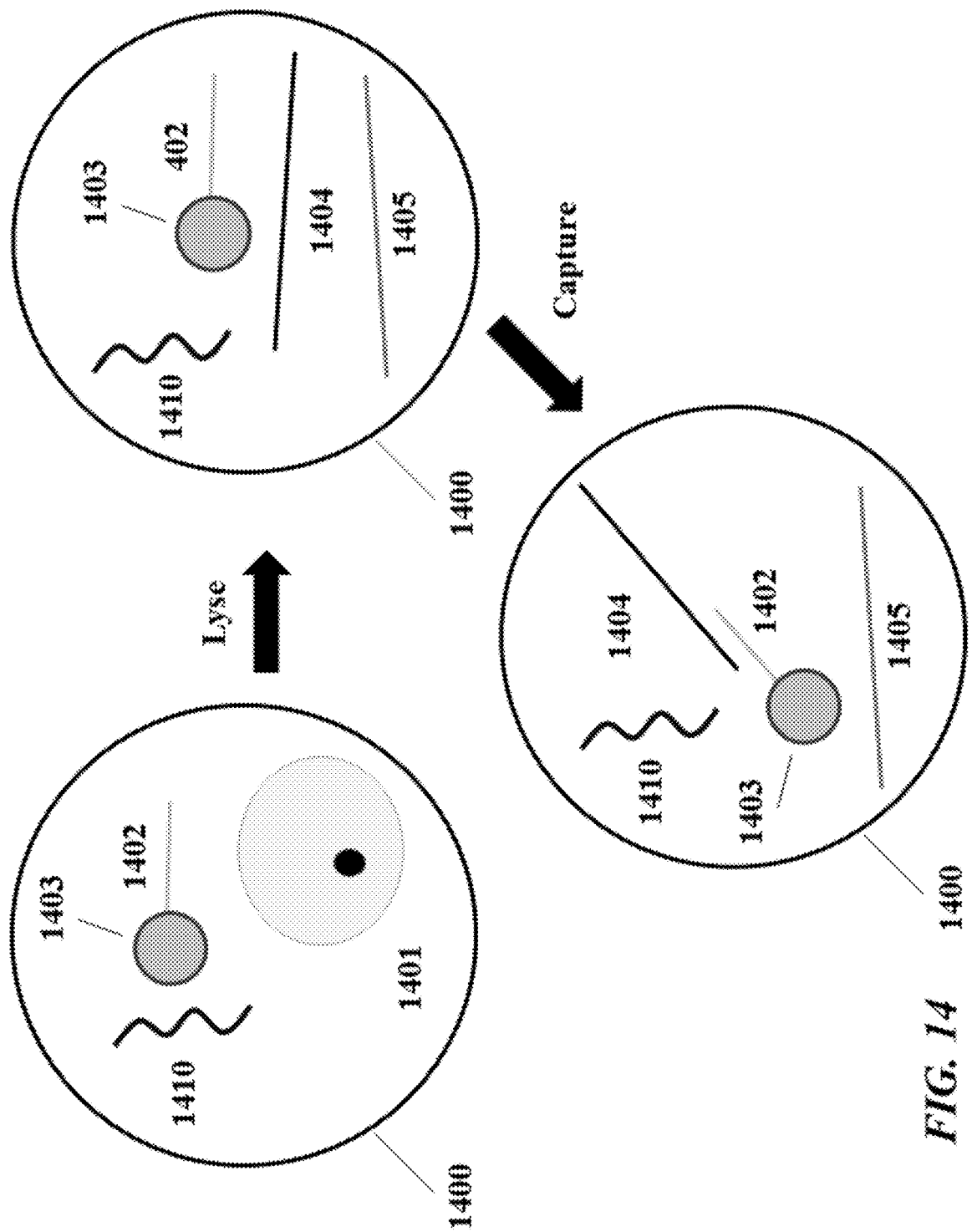
FIG. 14 illustrates another example process for generating droplets comprising constituents from a cell.

FIG. 14 illustrates an example method for capturing cellular mRNA or generating cDNA using an oligonucleotide attached to a magnetic particle. A partition 1400 (e.g., an aqueous droplet in an emulsion) may comprise a cell 1401, an oligonucleotide 1402 attached to a particle 1403 (e.g., a bead or magnetic particle), and a polymeric precursor 1410. In some embodiments, the oligonucleotide 1402 comprises a poly-T sequence, random N-mer, targeted capture/primer sequence, and/or any other additional sequences, such as the functional sequences described elsewhere herein. In some instances, the partition 1400 further comprises one or more reagents, such as reagents for performing one or more reactions on one or more components of the cell (e.g., a reverse transcriptase enzyme, buffer, cofactors, etc.) or reagents for polymerizing or gelling the polymeric precursor 1410. Cell 1401 may be lysed or permeabilized, thereby releasing or otherwise allowing access to multiple types of cellular constituents including mRNA 1404 and genomic DNA (gDNA) 1405. The mRNA 1404 is then subjected to conditions such that it hybridizes to the oligonucleotide 1402 (e.g., via a poly-T sequence), thereby capturing the mRNA. In some embodiments, the hybridized mRNA 1404 is converted into cDNA. The polymeric precursor 1410 can then be polymerized or gelled to generate a cell bead comprising the particle attached mRNA 1404 (or cDNA) and gDNA 1405. Thus, the captured mRNA 1404 (e.g., hybridized to the oligonucleotide 1402 coupled to the particle 1403) is incorporated into the cell bead. In some instances, the captured mRNA 1404 or cDNA can be purified away from the partition 1400 and processed separately.

In some embodiments, a partition is subjected to conditions sufficient to generate a cell bead comprising one or more reagents. For example, a partition droplet comprising polymer precursors attached to reagents (e.g., primers, nucleic acid molecules, etc.) may be polymerized or gelled such that the reagents are attached to the polymer or gel matrix (i.e., attached to a cell bead). In some instances, the reagents are releasably attached to the gel precursor via a labile bond (e.g., a chemically labile bond, thermally labile bond, or photo-labile bond). Reagents may be covalently attached to a cell bead. Reagents may be reversible or irreversibly attached to a cell bead. Reagents may be attached to the surface of a gel bead. Reagents may be attached to the inside of a cell bead. In some cases, mRNA is attached to a cell bead. For example, polymer precursors attached to mRNA from a cell may be polymerized or gelled to generate a cell bead such that the mRNA is attached to the cell bead. In some cases, cDNA is attached to a cell bead. For example, polymer precursors attached to cDNA derived from a cell may be polymerized to generate a cell bead such that the cDNA is attached to the cell bead. In some cases, one or more oligonucleotides are attached to a cell bead. For example, polymer precursors attached to the oligonucleotides may be polymerized or gelled to generate a cell bead such that the oligonucleotides are attached to the cell bead.

Figure 15:
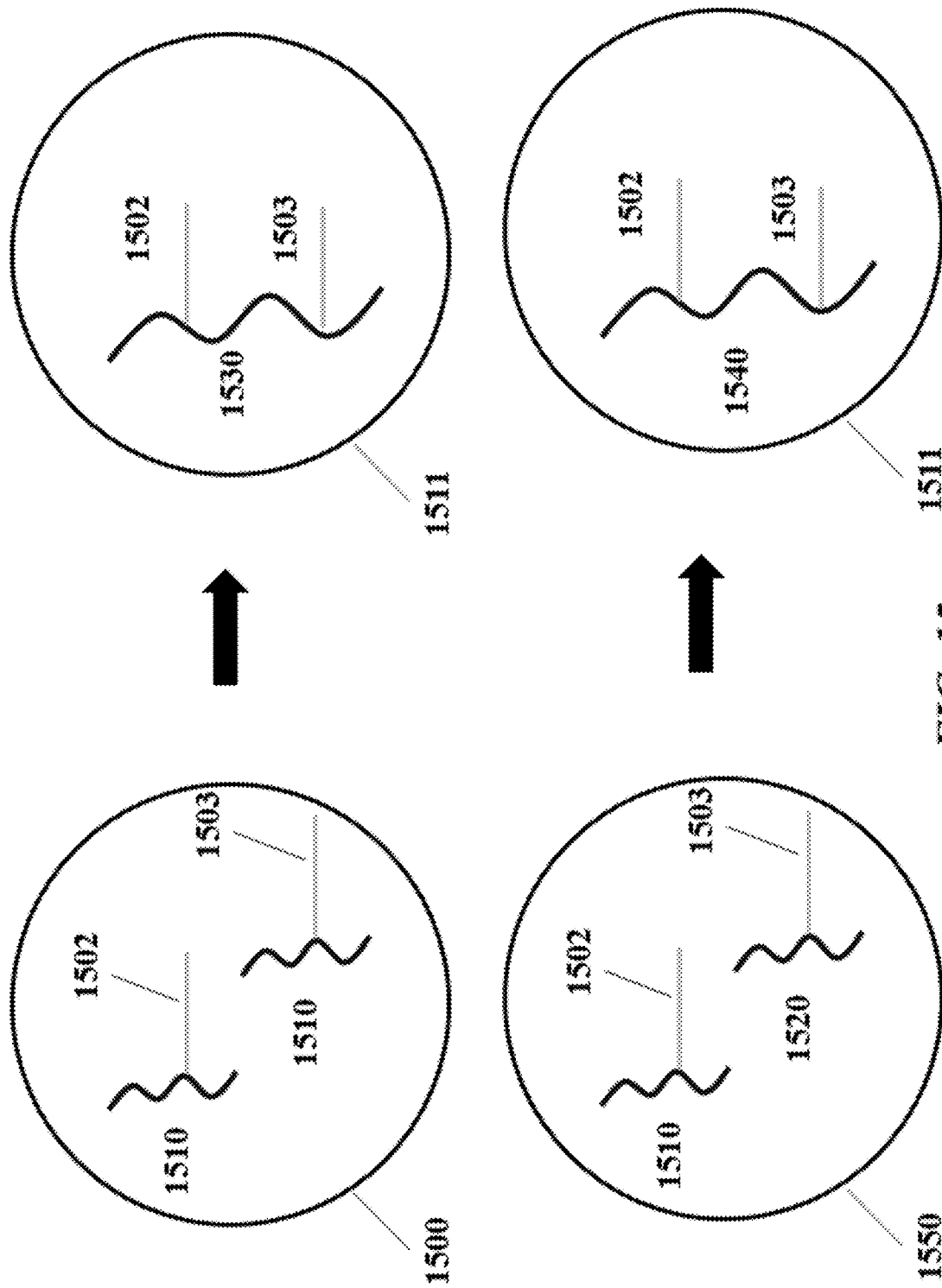
FIG. 15 illustrates an example process for generating cell beads comprising complementary deoxyribonucleic acid.

FIG. 15 illustrates an example of generating cell beads comprising reagents attached to a polymer matrix. A partition 1500 comprising polymer precursors 1510 attached to nucleic acid molecules 1502 and 1503 (e.g., mRNA, cDNA, primers, etc.) may be subjected to conditions sufficient to polymerize the polymer precursors, thereby generating a cell bead 1511 comprising nucleic acid molecules 1502 and 1503 attached to the polymer matrix 1530. In some instances, a partition 1550 comprises a first type of polymer precursor 1510 and a second type of polymer precursor 1520 and a cell bead 1511 is generated comprising a co-polymer 1530 of polymer precursors 1510 and 1520. In some instances, a nucleic acid molecule is attached to the first and/or second polymer precursors. For instance, a nucleic acid molecule 1502 can be attached to the first type of polymer precursor 1510 and a nucleic acid molecule 1503 can be attached to the second type of polymer precursor 1520 and a cell bead 1511 is generated comprising nucleic acid molecules 1502 and 1503 attached to the polymer matrix 1540. In some instances, nucleic acid molecule 1502 and nucleic acid molecule 1503 are identical. In some instances, nucleic acid molecule 1502 and nucleic acid molecule 1503 are the same type of molecule (e.g., mRNA or cDNA), but may contain different sequences. In other instances, nucleic acid molecule 1502 and nucleic acid molecule 1503 are different.

Attaching macromolecular constituents (e.g., nucleic acid molecules, protein, etc.) to a cell bead or a particle within a cell bead may be useful in preparing the species for further processing. For example, nucleic acid molecules attached to a cell bead or particle may be processed while remaining attached to the cell bead or particle. Following processing, a nucleic acid may be released (e.g., released into a partition) from a cell bead and/or particle for analysis. In some cases, it may be useful to attach one type of cellular component or derivative thereof (e.g., mRNA, cDNA) to a cell bead or a particle within a cell bead, while encapsulating but not attaching another type of cellular component (e.g., genomic DNA). This may be useful in, for example, facilitating separate processing of multiple types of components. For example, following cell bead formation, cell beads may be transferred to an aqueous solution and subjected to additional processing as described herein. For example, cell beads may be subjected, in bulk, to reverse transcription to generate cDNA from captured mRNA (e.g., hybridized to an oligonucleotide attached to the cell bead matrix or a particle, such as a magnetic particle).

Partitioning Cell Beads

Figure 16A:
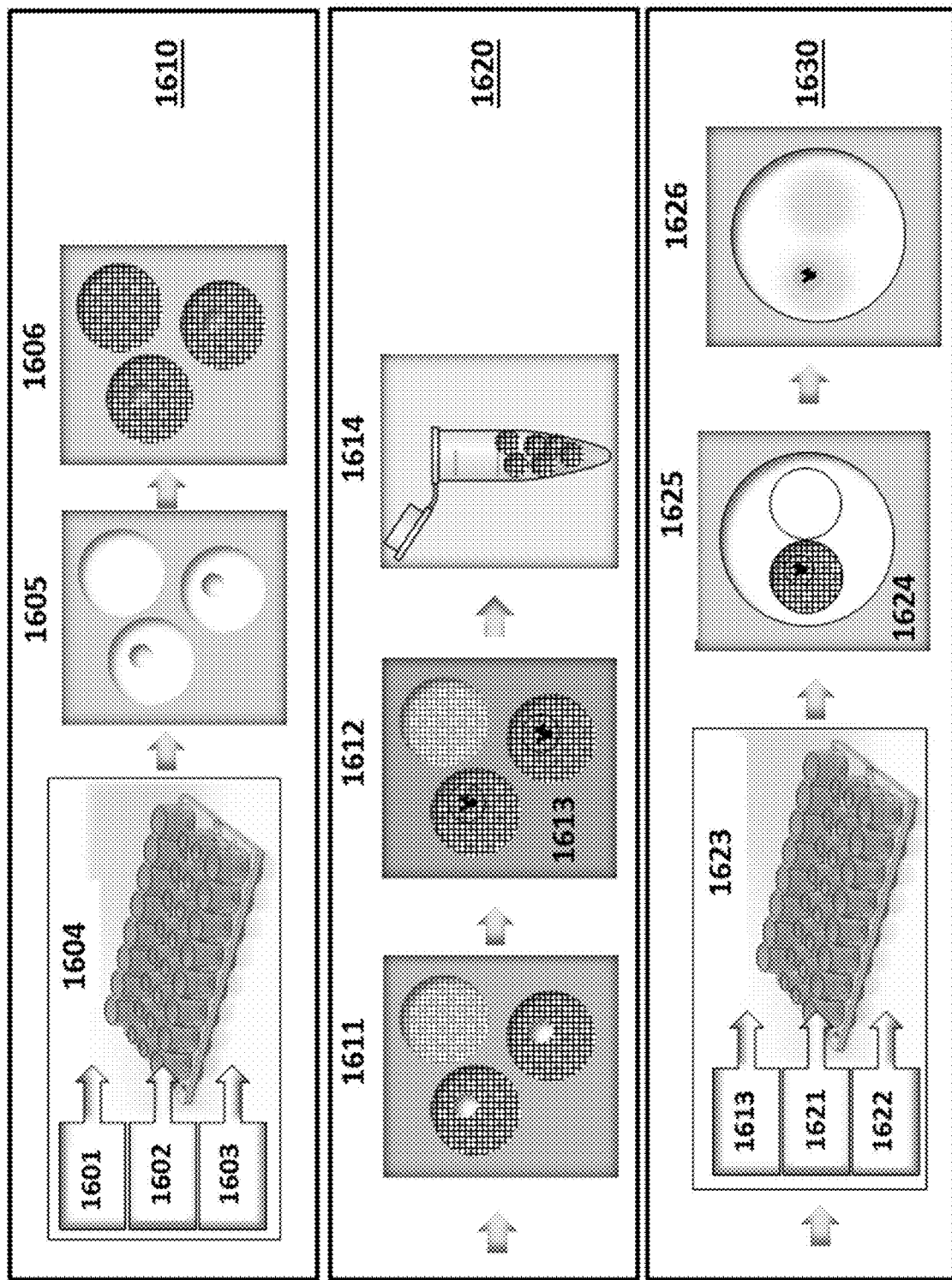
FIG. 16A schematically illustrates an example method for generating droplets comprising a barcoded bead and a cell bead.

Cell beads may be partitioned together with nucleic acid barcode molecules and the nucleic acid molecules of or derived from the cell bead (e.g., mRNA, cDNA, gDNA, etc.) can be barcoded as described elsewhere herein. In some embodiments, cell beads are co-partitioned with barcode carrying beads (e.g., gel beads) and the nucleic acid molecules of or derived from the cell bead are barcoded as described elsewhere herein. An overview of an example method for generating droplets comprising cell beads and nucleic acid barcode molecules is schematically depicted in FIG. 16A. The method described in FIG. 16A comprises three phases 1610, 1620, and 1630; with each respective phase comprising:

(1) generation of cell beads (1610); (2) cell bead solvent exchange and processing (1620); and (3) co-partitioning of cell beads and barcodes for subsequent tagging (e.g., barcoding) of one or more constituents of (or derived from) the cell bead (1630).

With continued reference to FIG. 16A, phase 1610 comprises providing an oil 1601, polymeric or gel precursors 1602, and cells or nuclei 1603 (e.g., a cell, a fixed cell, a cross-linked cell, a nuclei, a permeabilized nuclei, etc.) to a microfluidic chip 1604 for droplet generation. The polymeric or gel precursors may be electrically charged as described in, e.g., FIGS. 11-12. Charged species (not shown in FIG. 16A), such as those described elsewhere herein, may be further provided to microfluidic chip 1604 for co-partitioning. As detailed in FIG. 16B, the microfluidic chip 1604 comprises a plurality of reservoirs comprising the oil 1601, polymeric or gel precursors 1602 and cells 1603. Microfluidic chip 1604 may also comprise one or more additional reservoirs (not shown) comprising one or more additional reagents. Polymeric or gel precursors 1602 and cells 1603 are flowed (e.g., via the action of an applied force, such as negative pressure via a vacuum or positive pressure via a pump) from their reservoirs to a first channel junction and combine to form an aqueous stream. This aqueous stream is then flowed to a second channel junction, in which oil 1601 is provided. The aqueous stream provided from the first channel junction is immiscible with the oil 1601 resulting in the generation of a suspension of aqueous droplets in the oil 1605, which then flow to a reservoir for collection. Flow can be controlled within the microfluidic chip 1604 via any suitable method, including the use of one or more flow regulators in a channel or various channels, dimensioning of microfluidic channels, etc., as described elsewhere herein. As shown in both FIG. 16A and FIG. 16B, the product comprises droplets 1605 comprising a cell from the cells 1603 and polymeric or gel precursors 1602. In some cases, at least some of the droplets of droplets 1625 comprise a single cell.

In some cases, the droplets 1605 are subjected to conditions sufficient to lyse the cells or nuclei comprised therein, releasing cellular macromolecular constituents into the droplets 1605. The macromolecular constituents (e.g., nucleic acids, proteins, etc.) may be subjected to one or more reactions for additional processing. Processing of macromolecular constituents is described in more detail elsewhere herein. In other embodiments, the droplets 1605 are subjected to conditions sufficient to permeabilize the cells (or nuclei) thereby facilitating access to one or more macromolecular constituents of the cell (or nucleus) for further processing. The droplets 1605 are then be subjected to conditions suitable to polymerize or gel the polymeric or gel precursors 1602 in the droplets 1605, to generate cell beads 1606.

Continuing with FIG. 16A, the droplets 1605 are then subjected to conditions suitable to polymerize or gel the polymeric or gel precursors 1602 in the droplets 1605, which generates cell beads 1606 that encapsulate the cells (or nuclei) 1603. As the resulting cell beads 1606 are suspended in oil, phase 1620 is initiated which comprises a solvent exchange configured to resuspend the cell beads 1606 in an aqueous phase 1611. Additional details and examples regarding solvent exchange are provided elsewhere herein.

The resuspended aqueous cell beads 1611 can then, in bulk, be optionally processed 1612 to prepare the cell beads for analysis of one or more cellular components. For example, in 1612, cell beads 1611 can be subjected conditions suitable to lyse or permeabilize cells (or nuclei) in the cell beads 1613, thereby releasing or otherwise allowing access to one or more cellular constituents (e.g., nucleic acids, such as mRNA and gDNA, proteins, etc.). Separately or contemporaneously from cell lysis, cell beads (e.g., 1611 or 1613) are also subjected, in bulk, to conditions to denature nucleic acids derived from the cells (e.g., gDNA) associated with the cell beads 1611. The polymeric matrix of the cell beads 1613 effectively hinders or prohibits diffusion of larger molecules, such as nucleic acids and/or proteins, from the cell beads 1613. In addition, in cases where charged species are introduced into the polymer matrix, the electric charge (e.g., positive charge) of the cell beads effectively prevents diffusion of molecules of opposite charge (e.g., nucleic acid). The cell beads 1613 are sufficiently porous to facilitate diffusion of denaturation agents into the cell bead matrix to contact the nucleic acids within the cell beads 1613. In some cases, the cell beads (1611 or 1613) can then be subjected, in bulk, to conditions suitable for performing one or more reactions on nucleic acids or other analytes derived from the cells associated with the cell beads (1611 or 1613). For example, antibodies may be washed into and/or out of the resuspended cell beads (1611 or 1613). After processing 1612, the resulting cell beads 1613 are then collected 1614 and can be stored prior to initiation of phase 1630.

In phase 1630, droplets comprising the cell beads (1611 or 1613) and barcode beads 1622 (e.g., gel beads comprising nucleic acid barcode molecules attached thereto) are generated. As shown in FIG. 16A, an oil 1621, the cell beads 1613, and barcode beads 1622 each comprising a barcode sequence (e.g., each bead comprising a unique barcode sequence) are provided to a microfluidic chip 1623. An example microfluidic chip 1623 is shown in FIG. 16C. As shown in FIG. 16C, the microfluidic chip 1623 comprises a plurality of reservoirs comprising the oil 1621, cell beads 1613 and barcode beads 1622 (e.g., gel beads). The chip also includes additional reservoirs 1627 and 1628 that may be used to supply additional reagents (e.g., reagents for nucleic acid amplification, reagents that can degrade or dissolve cell beads and/or gel beads, reagents that degrade linkages between barcodes and gel beads, etc.). Cell beads 1613 and barcode beads 1622 are flowed (e.g., via the action of an applied force, such as negative pressure via a vacuum or positive pressure via a pump) from their reservoirs to a first channel junction and form an aqueous mixture. Materials from reservoirs 1627 and 1628 can also be provided to the aqueous mixture at the first channel junction.

Alternatively, cell beads and gel beads can be mixed before introduction into the microfluidic chip. In this case, a single reservoir of the microfluidic chip 1623 comprises a mixture of cell beads and gel beads. The ratio of cell beads to gel beads in the mixture can be varied to alter the number of droplets generated that comprise a single cell bead and a single gel bead. The mixture of cell beads and gel beads may be flowed (e.g., via the action of an applied force, such as negative pressure via a vacuum or positive pressure via a pump) from the reservoir to a first channel junction, in some cases together with materials from reservoirs 1627 and/or 1628. As an alternative or in addition to, cells may be mixed with gel beads. For example, a collection of cells and cell beads may be mixed with gel beads, or a collection of cells may be mixed with gel beads.

In some embodiments, the aqueous mixture comprising cell beads 1613, barcode beads 1621, and in some cases additional reagents is then flowed to a second channel junction, to which oil 1621 is provided. The aqueous mixture provided from the first channel junction is immiscible with the oil 1621 resulting in the generation of a suspension of aqueous droplets 1625 in the oil which then flow to a reservoir for collection. The microfluidic chip can also include a reservoir 1629 that can accept excess oil from the stream emerging from the second channel Flow can be controlled within the microfluidic chip 1623 via any suitable strategy, including the use of one or more flow regulators (see FIGS. 16C and 16D) in a channel or that connect channels, use of various channels, dimensioning of channels, etc. As shown in both FIG. 16A and FIG. 16C, the droplets 1625 comprise a cell bead 1613 and a barcode bead 1622 (e.g., a gel bead), in addition to any other reagents provided by reservoirs 1627 and 1628. In some cases, at least some droplets of droplets 1625 comprise a single cell bead and a single barcode bead (e.g., a single gel bead).

Where reagents that degrade or dissolve the cell beads 1613, barcoded beads 1622 (e.g., gel beads) and/or linkages between barcodes and barcoded beads 1622 (e.g., gel beads) are present in droplets, these reagents can release the nucleic acids trapped in the cell beads 1613 from the cell beads 1613 and/or release the barcodes from the barcode beads 1622. The nucleic acid barcode molecules then interact with the released cellular components (e.g., cellular nucleic acids) to generate barcoded nucleic acid molecules for nucleic acid sequencing as described elsewhere herein. In embodiments where the barcode bead (e.g., gel bead) is degraded or nucleic acid barcode molecules are releasably attached to the barcode bead (e.g., gel bead), the barcoded cellular components (e.g., barcoded cDNA or gDNA fragments) are not attached to the bead. Where a given droplet comprises a single cell bead and a single barcoded bead comprising nucleic acid barcode molecules comprising a common barcode sequence, the barcoded cellular components (or derivatives thereof) can be associated with the cell (or other biological sample, such as a bacterium or virus) of the given cell bead via the common barcode sequence.

Figure 16B:
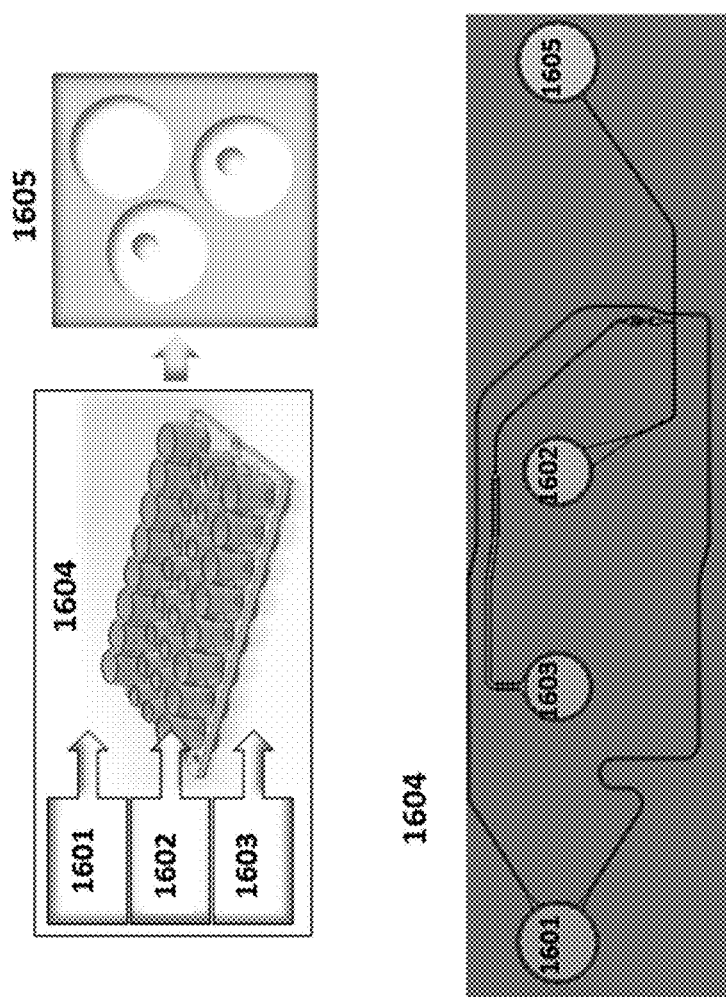
FIG. 16B illustrates an example microfluidic architecture for generating cell beads.
Figure 16C:
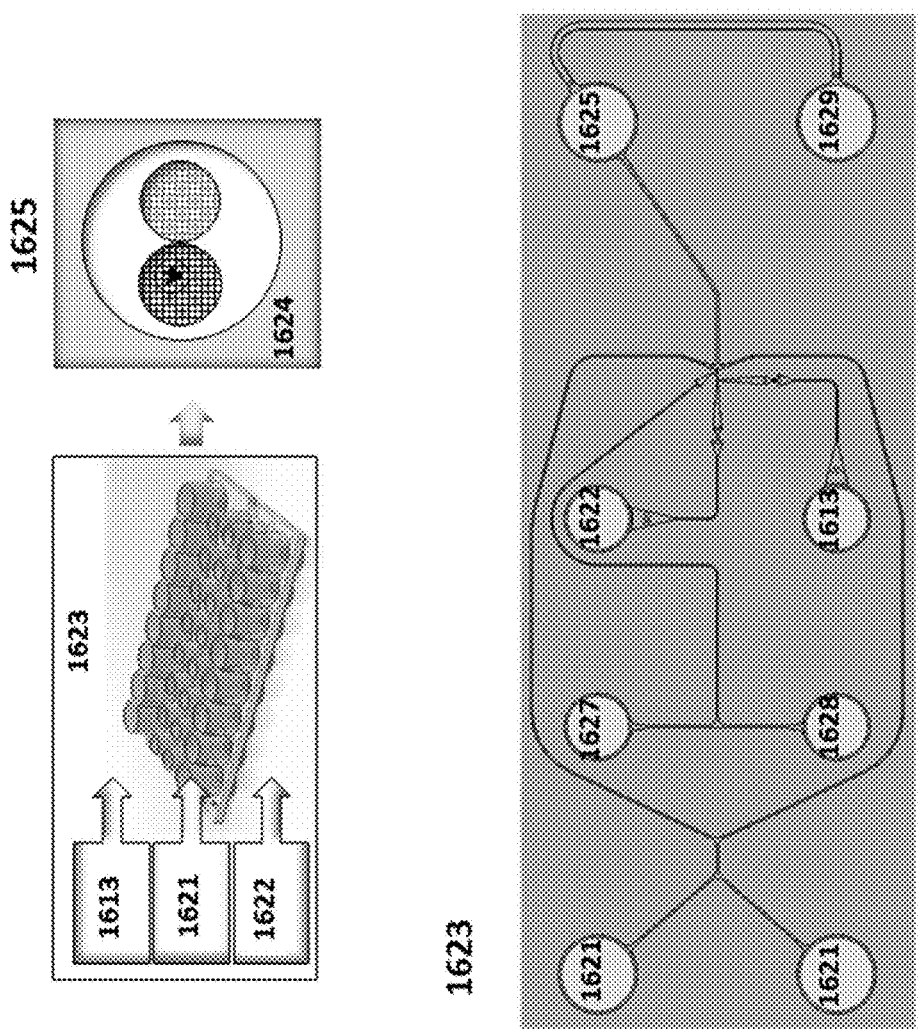
FIG. 16C illustrates an example microfluidic architecture for generating droplets comprising barcoded beads and cell beads.
Figure 16D:
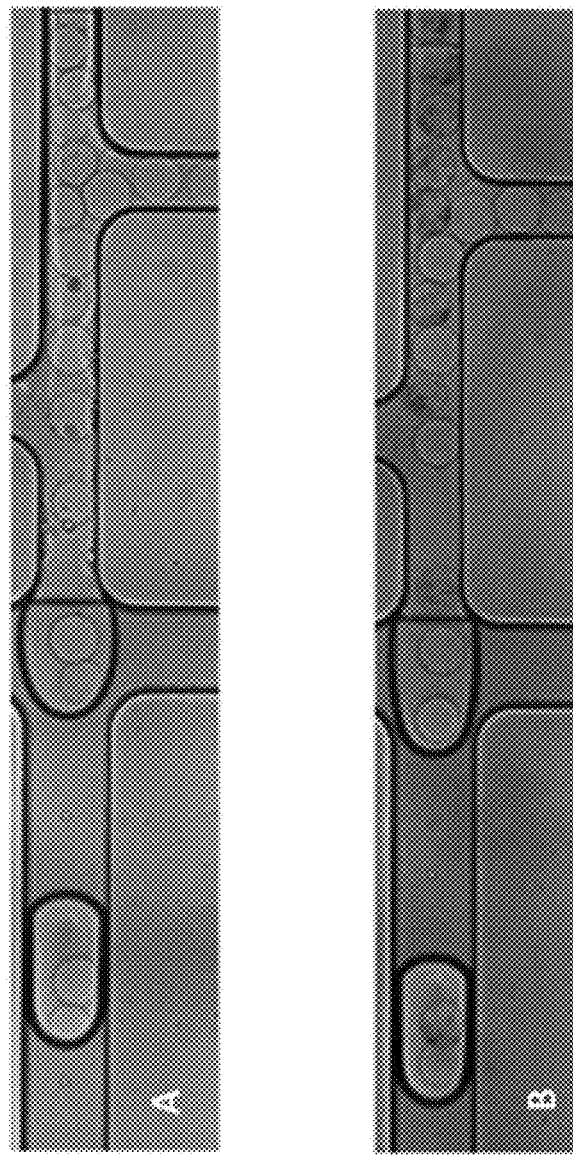
FIG. 16D illustrates an example droplet generation process generating droplets comprising a barcoded bead and a cell bead using the architecture shown in FIG. 16C.

FIG. 16D depicts two example microfluidic reactions demonstrating the generation of droplets 1625 comprising cell beads and gel beads using the method of FIG. 16A and the microfluidic devices depicted in FIGS. 16B and 16C. FIG. 16D (panel A) shows droplets comprising cell beads and gel beads while FIG. 16D (panel B) shows droplets comprising cell beads comprising magnetic materials (e.g., magnetic particles) and gel beads.

Figure 17:
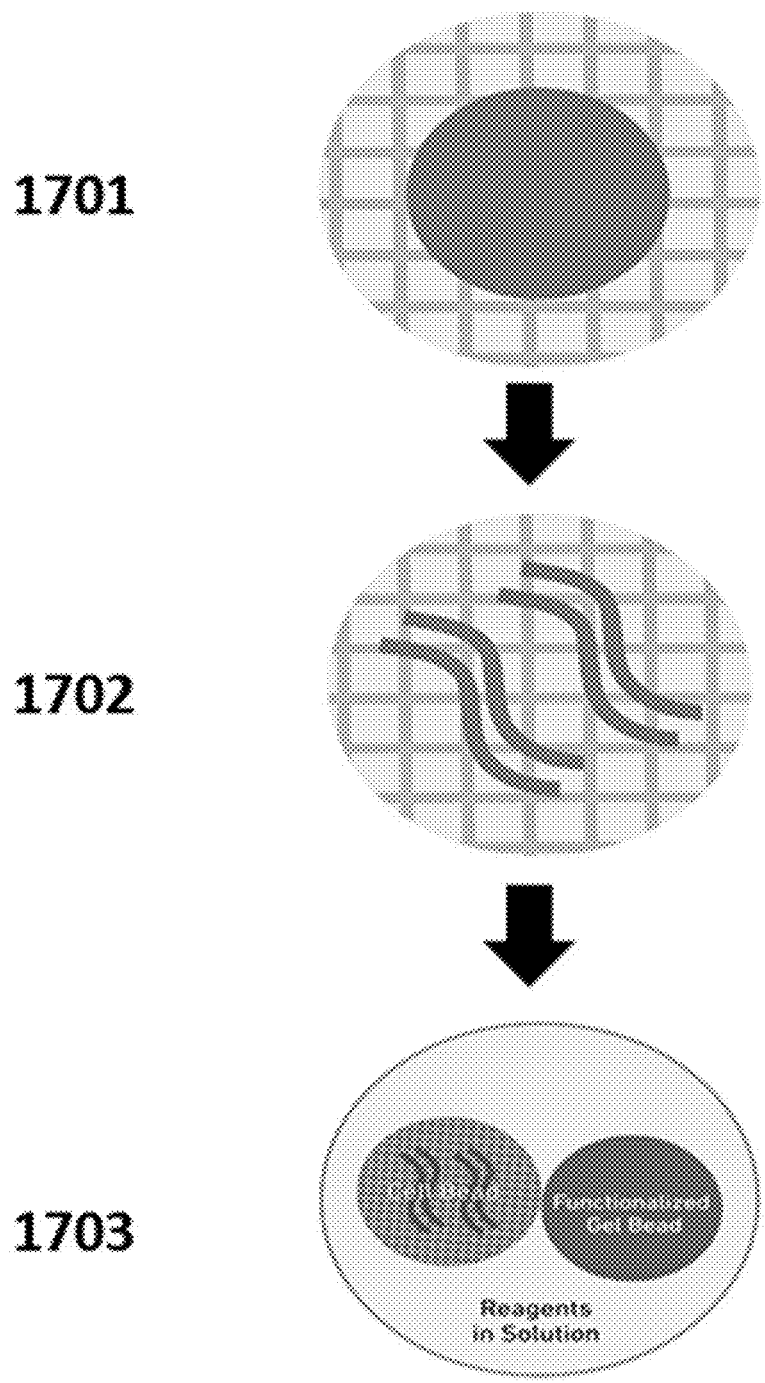
FIG. 17 shows an example process for generating a cell bead and a partition comprising a cell bead and a gel bead.

Partitions comprising a barcode bead (e.g., a gel bead) associated with barcode molecules and a bead encapsulating cellular constituents (e.g., a cell bead) such as cellular nucleic acids can be useful in constituent analysis as is described in U.S. Patent Publication No. 2018/0216162, which is herein incorporated by reference in its entirety for all purposes. Generation of a partition comprising a barcode bead and a cell bead is schematically depicted in FIG. 17. The cell bead is generated in operation 1701 by encapsulating a cell in a polymer matrix to form the cell bead. The cell is then lysed in operation 1702 such that the nucleic acids, and other constituents of the cell, are released from the cell and entrapped by the cell bead polymer matrix. The cell bead is then processed in conditions suitable to, e.g., digest proteins and/or denature nucleic acids (e.g., via an alkaline reagent) in operation 1703. The cell beads can then be washed and isolated for further processing.

Computer Systems

Figure 18:
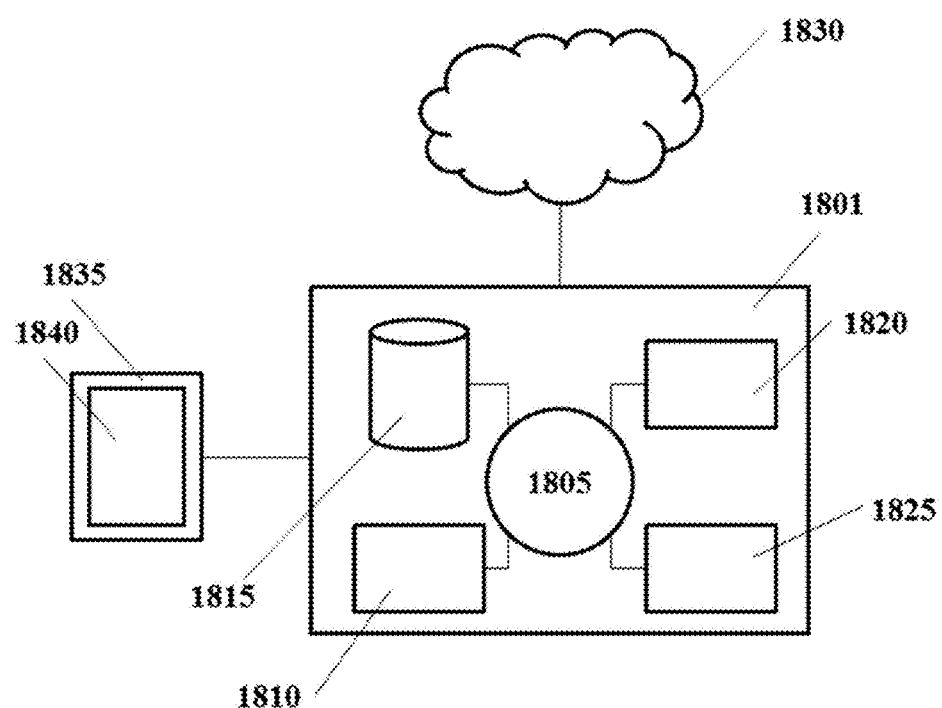
FIG. 18 shows an example computer system that is programmed or otherwise configured to implement methods and systems provided herein.

The present disclosure provides computer systems that are programmed to implement methods of the disclosure. FIG. 18 shows a computer system 1801 that is programmed or otherwise configured to (i) control a microfluidics system during the formation of the droplets, e.g., the rate of adding each component at different channels, (ii) control the reaction conditions for the click chemistry reaction inside droplets, and (iii) perform sequencing applications. The computer system 1801 can regulate various aspects of the present disclosure, such as, for example, regulating the rate of adding various reagents, e.g., the reducing agent, and regulating the fluid flow rate in one or more channels in a microfluidic structure when forming the droplets. The computer system 1801 can be an electronic device of a user or a computer system that is remotely located with respect to the electronic device. The electronic device can be a mobile electronic device.

The computer system 1801 includes a central processing unit (CPU, also "processor" and "computer processor" herein) 1805, which can be a single core or multi core processor, or a plurality of processors for parallel processing. The computer system 1801 also includes memory or memory location 1810 (e.g., random-access memory, read-only memory, flash memory), electronic storage unit 1815 (e.g., hard disk), communication interface 1820 (e.g., network adapter) for communicating with one or more other systems, and peripheral devices 1825, such as cache, other memory, data storage and/or electronic display adapters. The memory 1810, storage unit 1815, interface 1820 and peripheral devices 1825 are in communication with the CPU 1805 through a communication bus (solid lines), such as a motherboard. The storage unit 1815 can be a data storage unit (or data repository) for storing data. The computer system 1801 can be operatively coupled to a computer network ("network") 1830 with the aid of the communication interface 1820. The network 1830 can be the Internet, an internet and/or extranet, or an intranet and/or extranet that is in communication with the Internet. The network 1830 in some cases is a telecommunication and/or data network. The network 1830 can include one or more computer servers, which can enable distributed computing, such as cloud computing. The network 1830, in some cases with the aid of the computer system 1801, can implement a peer-to-peer network, which may enable devices coupled to the computer system 1801 to behave as a client or a server.

The CPU 1805 can execute a sequence of machine-readable instructions, which can be embodied in a program or software. The instructions may be stored in a memory location, such as the memory 1810. The instructions can be directed to the CPU 1805, which can subsequently program or otherwise configure the CPU 1805 to implement methods of the present disclosure. Examples of operations performed by the CPU 1805 can include fetch, decode, execute, and writeback.

The CPU 1805 can be part of a circuit, such as an integrated circuit. One or more other components of the system 1801 can be included in the circuit. In some cases, the circuit is an application specific integrated circuit (ASIC).

The storage unit 1815 can store files, such as drivers, libraries and saved programs. The storage unit 1815 can store user data, e.g., user preferences and user programs. The computer system 1801 in some cases can include one or more additional data storage units that are external to the computer system 1801, such as located on a remote server that is in communication with the computer system 1801 through an intranet or the Internet.

The computer system 1801 can communicate with one or more remote computer systems through the network 1830. For instance, the computer system 1801 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1801 via the network 1830.

Methods as described herein can be implemented by way of machine (e.g., computer processor) executable code stored on an electronic storage location of the computer system 1801, such as, for example, on the memory 1810 or electronic storage unit 1815. The machine executable or machine readable code can be provided in the form of software. During use, the code can be executed by the processor 1805. In some cases, the code can be retrieved from the storage unit 1815 and stored on the memory 1810 for ready access by the processor 1805. In some situations, the electronic storage unit 1815 can be precluded, and machine-executable instructions are stored on memory 1810.

The code can be pre-compiled and configured for use with a machine having a processor adapted to execute the code or can be compiled during runtime. The code can be supplied in a programming language that can be selected to enable the code to execute in a pre-compiled or as-compiled fashion.

Aspects of the systems and methods provided herein, such as the computer system 901, can be embodied in programming Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example; a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1801 can include or be in communication with an electronic display 1835 that comprises a user interface (UI) 1840 for providing, for example, the extent of hydrogels formation and the swell ratio of the hydrogels. Examples of UIs include, without limitation, a graphical user interface (GUI) and web-based user interface. Methods and systems of the present disclosure can be implemented by way of one or more algorithms. An algorithm can be implemented by way of software upon execution by the central processing unit 1805. The algorithm can, for example, performing sequencing, and adjusting the addition of various reagents according to the extent of certain reactions.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) form a single cell. For example, a biological particle (e.g., a cell or cell bead) is partitioned in a partition (e.g., droplet), and multiple analytes from the biological particle are processed for subsequent processing. The multiple analytes may be from the single cell. This may enable, for example, simultaneous proteomic, transcriptomic and genomic analysis of the cell.

Example 1: Syntheses of Monomers and Polymers with Click Chemistry Moieties

In some cases, a carboxylic acid group is introduced into a polymer as an anchor to attach click chemistry moieties/precursors. As shown in Scheme 3, an acid-containing polymer 1C can be made by reaction of monomer 1A with monomer 1B in the presence of an initiator. Integers m and n are greater than 1.

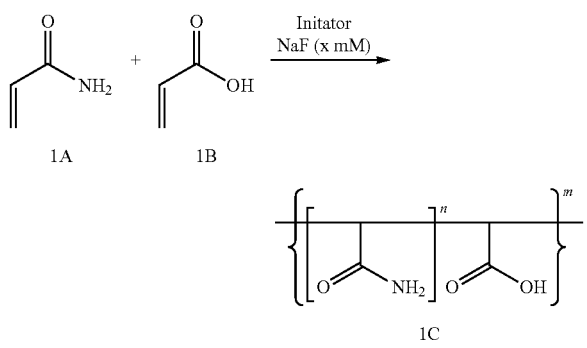

When about 1 wt % of monomer 1B is used relative to monomer 1A in the presence of about 1.6 M of NaF (about 1:1 ratio of NaF: total monomers) and a thermal initiator (e.g., 2,2'-azobis[2-(2-imidazolin-2-yl)propane] dihydrochloride, VA-044 from Wako, about 0.1 wt %) at temperatures of from about 30° C. to about 50° C., a polymer of number average molar mass ($M_n$) of about 156K can be obtained with a polydispersity index ($MW/M_n$) of about 1.786.

According to Scheme 4A, polymer 1C can couple with propargyl amine 1D to afford polymer 1E, which can bear a plurality of click chemistry moieties (alkynes). The coupling agent can be any coupling agent to form an amide bond from an acid and an amine. For example, EDCI, HOBt, or HATU. The reaction can be conducted under controlled pH, such as, for example, from about pH 5.0 to about pH 9.0, from about pH 6.0 to about pH 8.0, from about pH 6.5 to about pH 7.5, about pH 5.0, about pH 5.5, about pH 6.0, about pH 6.5, about pH 7.0, about pH 7.5, about pH 8.0, about pH 8.5, or about pH 9.0.

-continued

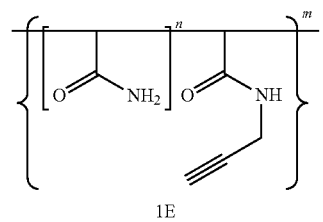

1E

Syntheses of azide-containing polymers can take at least two different routes as well. One route, similar to Scheme 4A for propargyl-containing polymers, is to couple the carboxylic acid of polymer 1C to a primary amine 1DD bearing an azide functionality using an amide coupling agent to provide an azide-containing polymer 1EE, as shown in Scheme 4B.

Scheme 4A

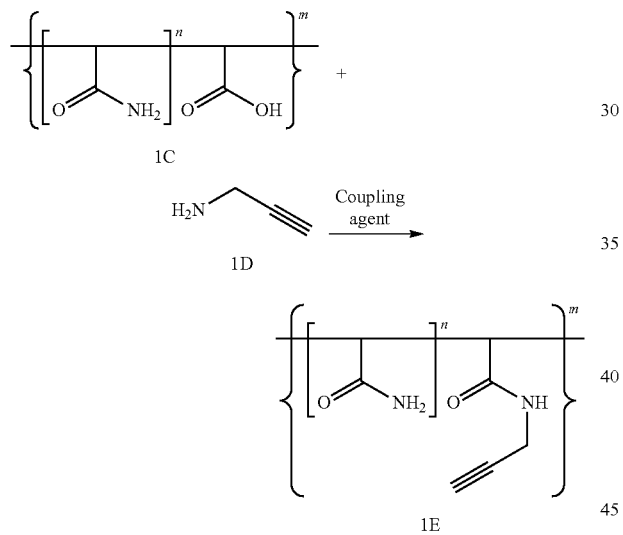

Alternatively, polymer 1E can be formed from monomer 1A and monomer 1F in a polymerization reaction shown in Scheme 5. The monomer 1F can be formed by a coupling reaction between monomer 1A and propargyl amine 1D in the presence of a coupling reagent similar to the one used in Scheme 4. In some cases, about 1.5 wt % of monomer 1F relative to monomer 1A in presence of about 0.1 wt % of AIBN and 1.2 M of NaF at 30 C can form polymer 1E.

Scheme 4B

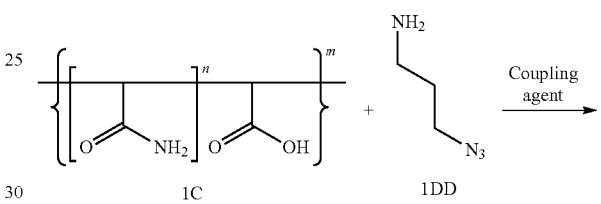

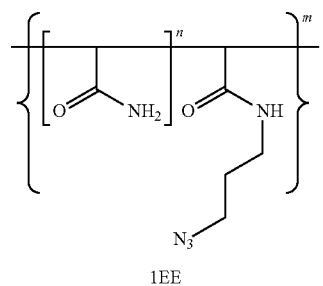

1EE

Alternatively, the primary amine bearing an azide functionality can be an p-azido-picolyl compound 1DP which can be coupled to polymer 1C using an amide coupling agent to provide p-azido-picolyl containing polymer 1EF, as shown in Scheme 4C.

Scheme 5

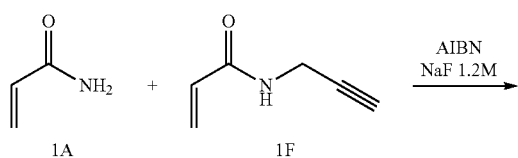

Scheme 4C

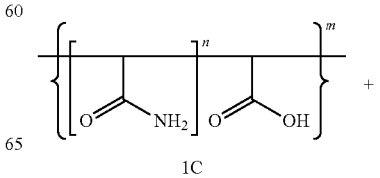

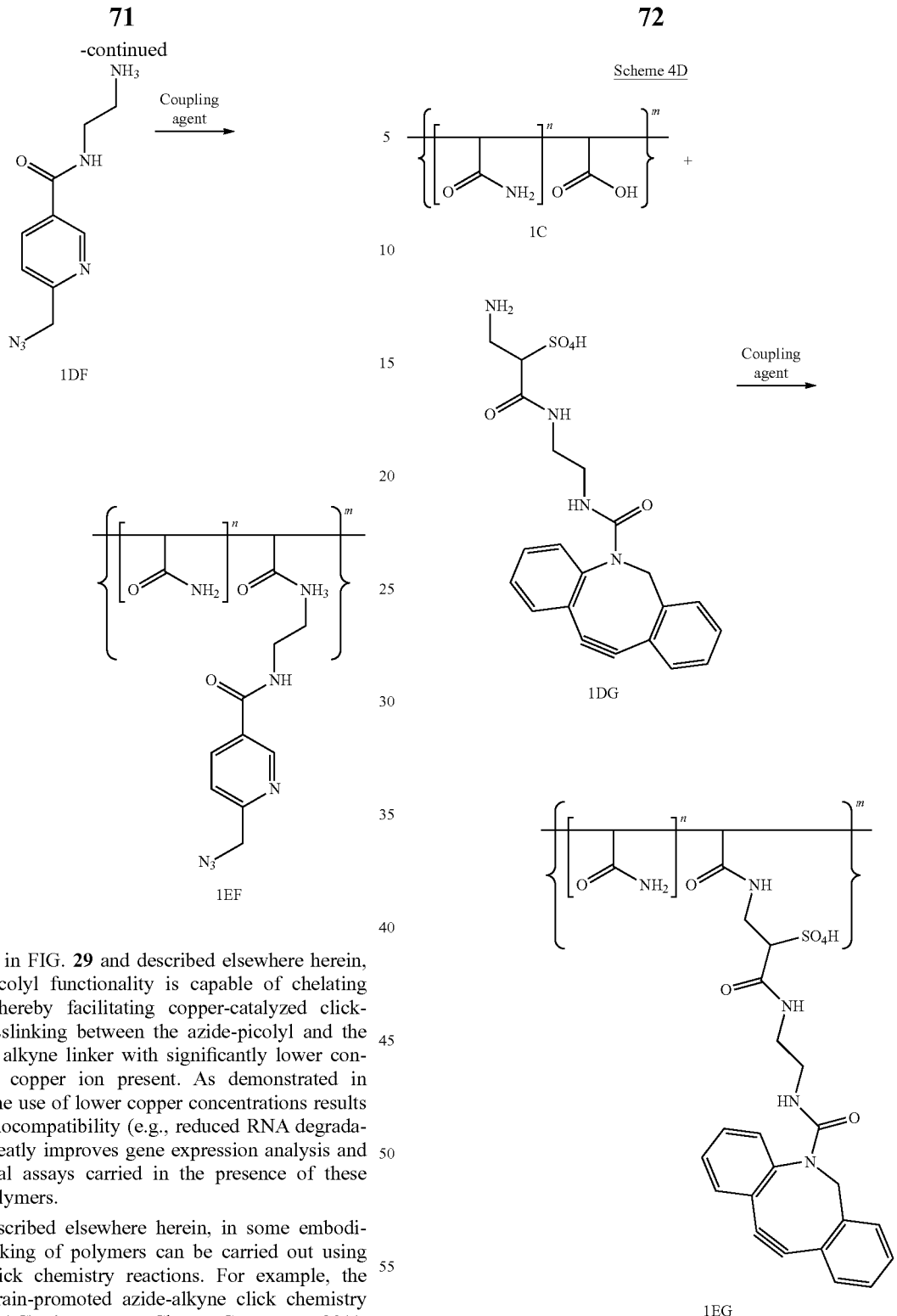

Figure 29:
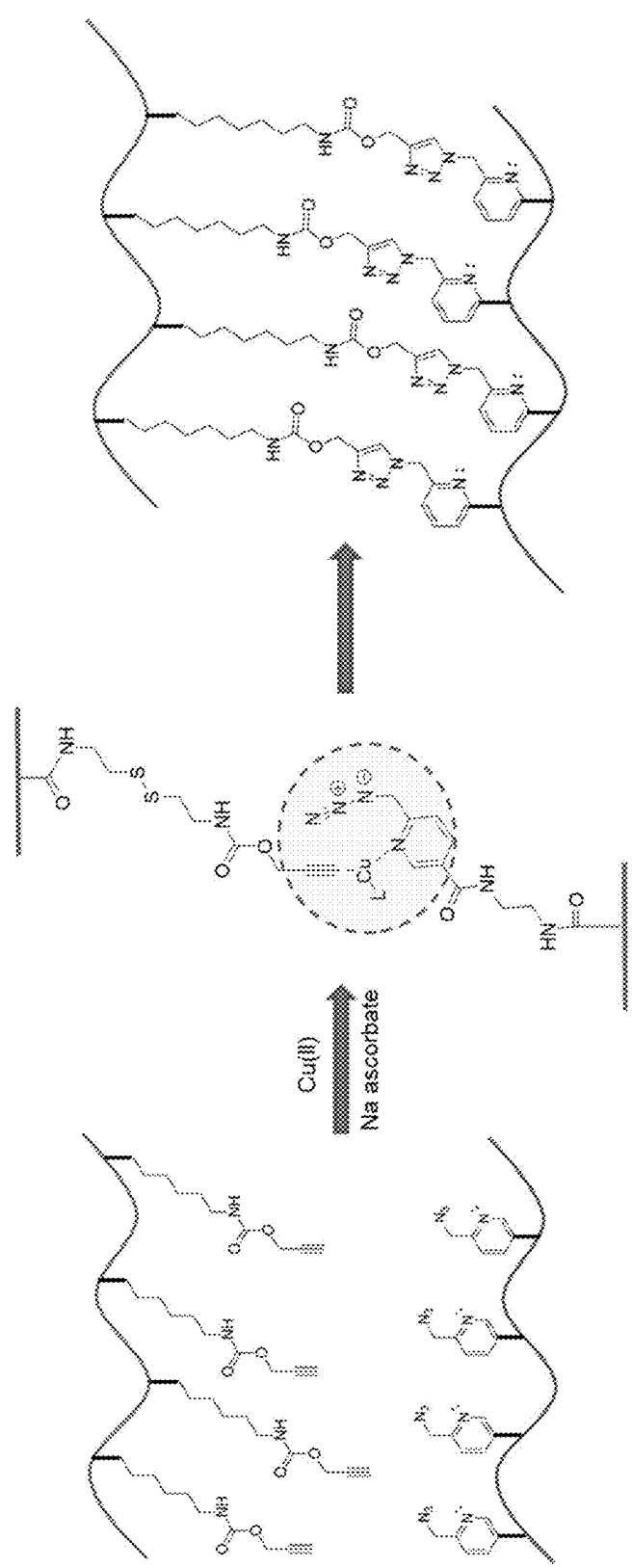
FIG. 29 shows an exemplary low-copper concentration click chemistry crosslinking reaction using an azide-picolyl modified linker.

As depicted in FIG. 29 and described elsewhere herein, the p-azido-picolyl functionality is capable of chelating Cu(I)/Cu(II) thereby facilitating copper-catalyzed click-chemistry crosslinking between the azide-picolyl and the corresponding alkyne linker with significantly lower concentrations of copper ion present. As demonstrated in Example 11, the use of lower copper concentrations results in improved biocompatibility (e.g., reduced RNA degradation) which greatly improves gene expression analysis and other biological assays carried in the presence of these crosslinked polymers.

Also, as described elsewhere herein, in some embodiments crosslinking of polymers can be carried out using copper-free click chemistry reactions. For example, the copper-free strain-promoted azide-alkyne click chemistry reaction (SPAAC) (see, e.g., Chem. Commun., 2011, 47:6257-6259 and Nature, 2015, 519(7544):486-90) can be used in which an azide-modified linker reacts with a dibenzocyclooctyne-amine (DBCO)-modified linker to form a click chemistry linkage as shown in FIG. 30. An azide-modified linker 1EE attached to polyacrylamide polymer can be used as described above in Scheme 4B. The DBCO-modified linker attached to a polyacrylamide 1EG can be prepared using a sulfonated DBCO-analogue 1DG as shown in Scheme 4D.

Another route is to polymerize monomer 1A with an azide-containing acrylamide. Common to both syntheses can be an amine reagent 1H as shown in Scheme 6. The amine reagent 1H can couple with polymer 1C to afford azide-containing polymer 1J. Additionally, the amine reagent 1H can couple with acryloyl chloride to produce monomer 1I, which can polymerize with monomer 1A to give polymer 1J containing an azide group.

Scheme 6

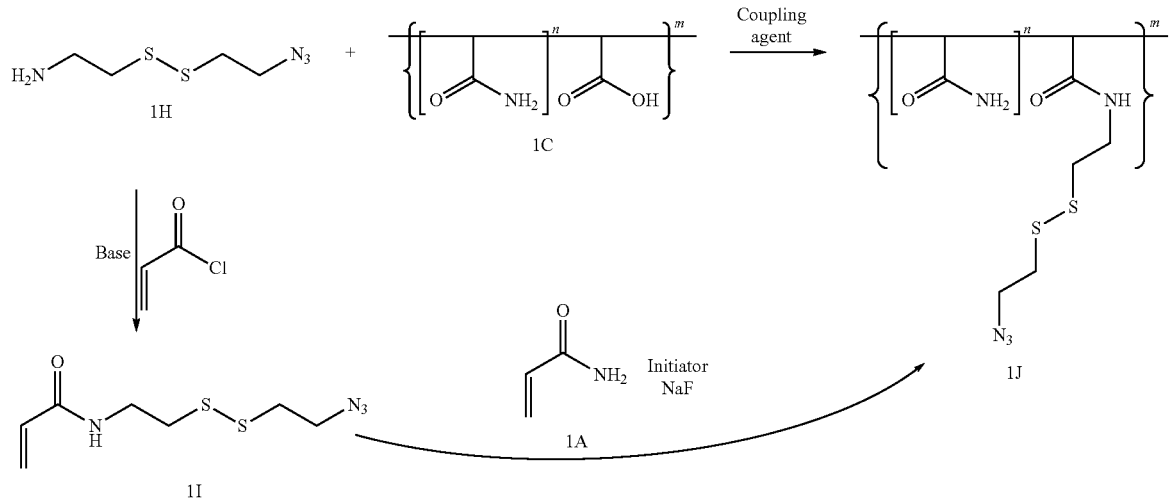

A propargyl-containing monomer 1M can be synthesized as shown in Scheme 7A. Propargyl alcohol can react with carbonyl-diimidazole to afford propargylating agent 1K. Mono-propargylation of cystamine 1L with propargylating agent 1K can provide mono-propargylated cystamine 1KL, which can be further acylated on the free amine to provide disulfide-linked, propargylated monomer 1M. Monomer 1M is a degradable alkyne-containing monomer.

Scheme 7A

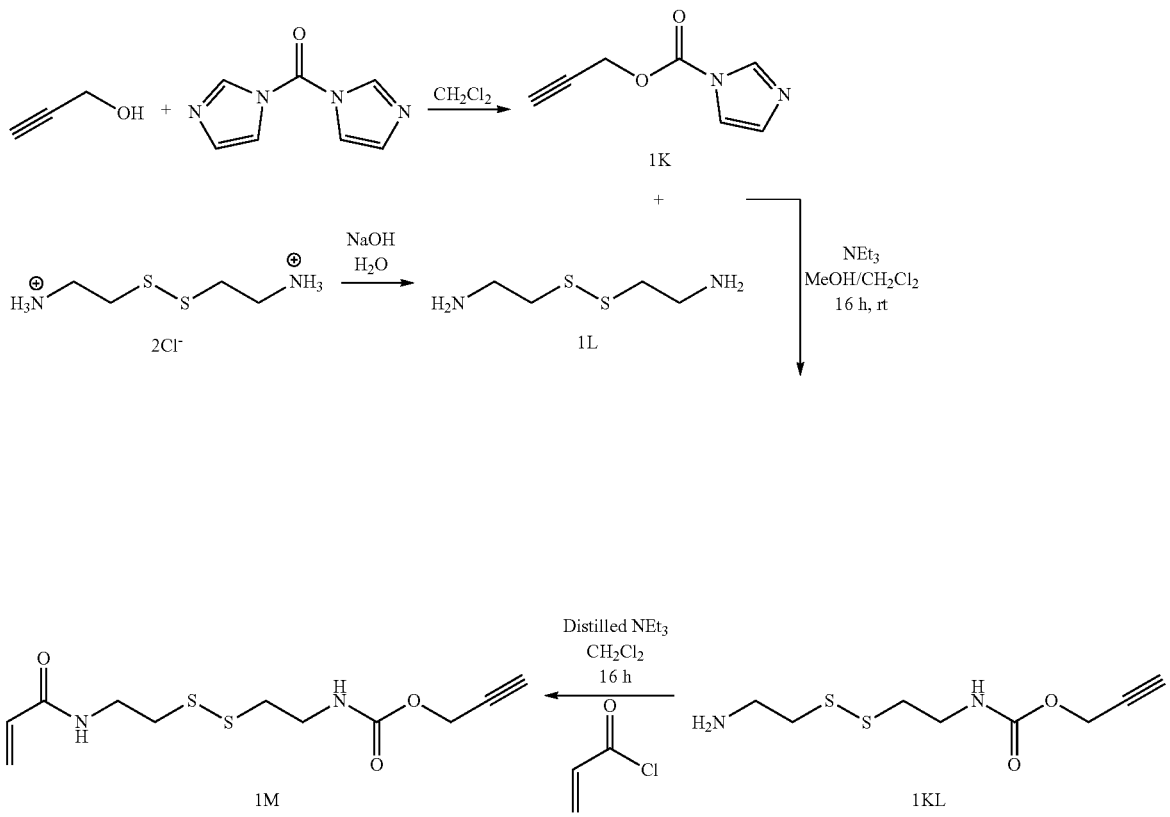

Alternatively, a propargyl-containing monomer 1Q that does not include a disulfide linkage can be synthesized as shown in Scheme 7B. The monomer 1Q, however, contains a carbamate linkage that is labile. As described elsewhere herein, the monomer 1Q can be used in to form crosslinked polymers that do not degrade in the presence of DTT but can be selectively degraded in the presence of DETA and heat.

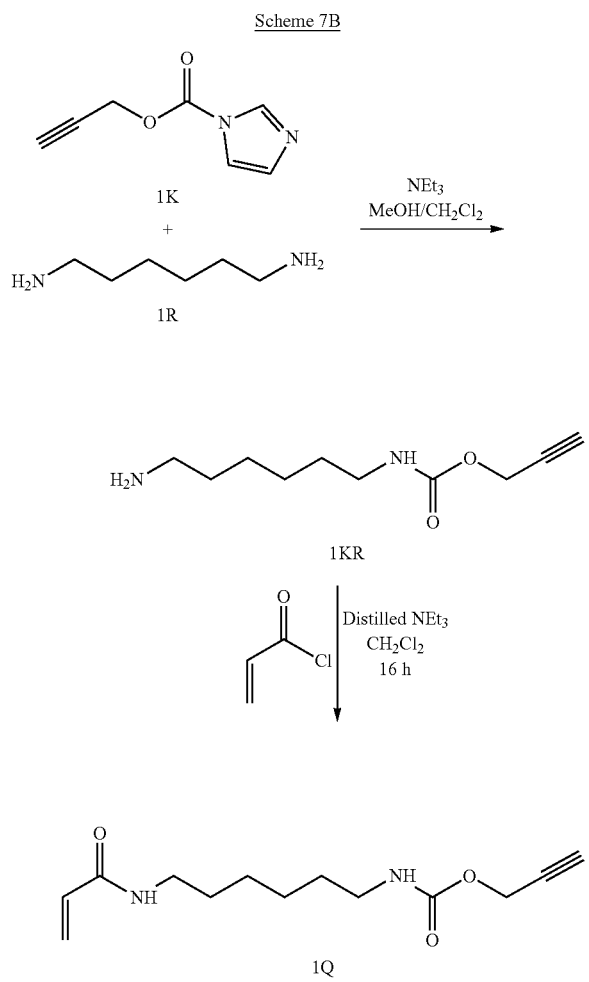

The synthesis of Scheme 7B is essentially the same as Scheme 7A, however the reagent 1,6-dihexylamine 1R, rather than cystamine 1L, is reacted with propargylating agent 1K to provide a mono-propargylated hexylamine carbamate 1KR. The free amine of 1KR can then be further acylated on to provide the carbamate-linked, propargylated monomer 1Q.

An azide-containing monomer 1N can be made from p-azidoaniline via acylation as shown in Scheme 8.

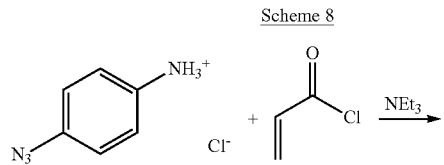

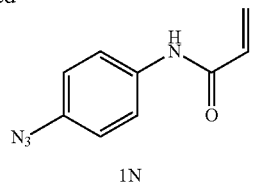

Each of the monomers 1M, 1N can undergo polymerization with monomer 1A to produce the corresponding polymers bearing click chemistry moieties.

Experiment 1: Preparation of Copper (II) Reagent in the Oil Phase.

1) Suspension of copper (II) salt. About 2.50 mM Krytox-COOH and about 1.25 mM Cu(OAc)$_2$ are stirred in HFE-7500 for about 48 hours at room temperature.

2) Preparation of GB Oil. GB Oil can be prepared by mixing about 2.50 mM bis-Krytox-ethylene glycol-polymer (Krytox-PEG-Krytox or BKEP or Formula I) and about 0.25 mM Krytox in solvent HFE-7500 engineered oil. GB Oil can be pre-formulated in bulk.

3) Preparation of the oil phase solution CB Oil. The suspension of copper (II) salt and the GB oil can be combined together in v/v=1:1 ratio, and the resulting mixture can be stirred at room temperature for about 1 hour and filtered through a 0.22 μm PES filter to remove insoluble copper (II) salts. The filtrate is CB Oil comprising 1.25 mM BKEP, about 1.375 mM Krytox-COOH, and about 0.625 mM copper (II) in HFE-7500. Concentration of copper (II) in aqueous layer can be analyzed using UV-vis absorption spectroscopy (maximum absorbance wavelength at about 286 nm).

Experiment 2: Preparation of the Aqueous Phase Solution.

A stock solution 1 of the aqueous phase solution can be prepared by mixing polymer pairs of azide-containing and alkyne-containing polymers (3.5% w/v), F-108 (0.5% w/v), magnetic particles (0.12% w/v), THPTA (0.25 mM) in water.

A stock solution 2 of the aqueous phase solution can be prepared by mixing polymer pairs of azide-containing and alkyne-containing polymers (3.5% w/v), F-108 (0.5% w/v), magnetic particles (0.12% w/v), THPTA (0.25 mM), and sodium ascorbate (156 mM) in water.

Experiment 3: Click Chemistry and Gelation in the Absence of Cells.

To make emulsions of discrete droplets, an equipment setup similar to that depicted in FIG. 7 can be employed. Specifically, Stock solution 1 (30 μL from Experiment 2) can be fed through channel 701; stock solution 2 (40 μL, from Experiment 2) can be fed through channel 702; and CB Oil (200 μL, from Experiment 1) can be fed through channel 704. A collection of water-in-oil emulsions of droplets can be obtained in a collecting well. The emulsions of droplets can be kept in the well (with a cover) for about 60 minutes. Subsequent solvent exchange can convert the oil phase into an aqueous phase. Gelation can be observed visually and under microscope. Swell ratio of the gels can be measured by comparing size data between monodisperse in aqueous phase (100 minutes) and monodisperse in NaOH phase (5 minutes) under microscope.

Experiment 4: Click Chemistry and Gelation in the Presence of Cells.

Figure 19:
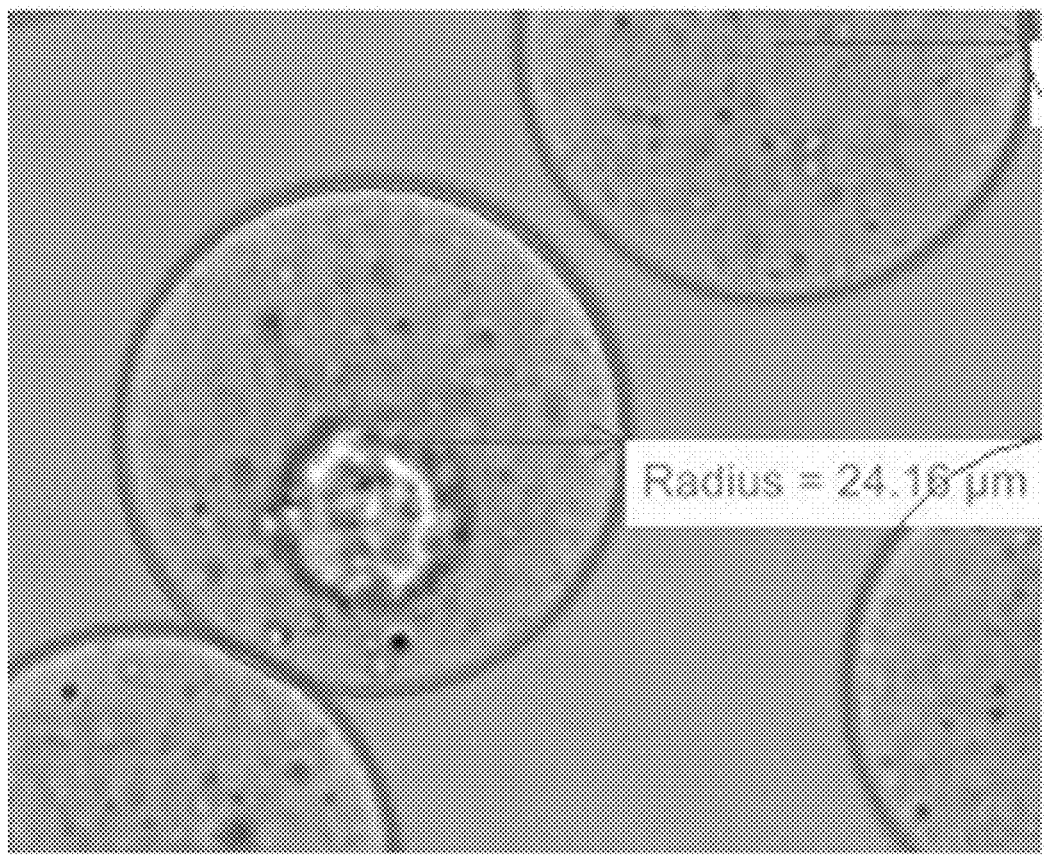
FIG. 19 shows a representative microscope image of a cell bead enclosing a cell.

To make emulsions of discrete droplets, an equipment setup similar to that depicted in FIG. 7 can be employed. Specifically, Stock solution 1 (30 μL, from Experiment 2) can be fed through channel 701; stock solution 2 (40 μL, from Experiment 2) and cells (100 cells/µL) can be fed through channel 702; and CB Oil (200 µL, from Experiment 1) can be fed through channel 704. A collection of water-in-oil emulsions of droplets can be obtained in a collecting well. The emulsions of droplets can be kept in the well (with a cover) for about 60 minutes. Subsequent solvent exchange can convert the oil phase into an aqueous phase (5 mM EDTA). Gels can be washed by phosphate-buffered-saline (3×). Gelation can be observed. Single cell trapped gels can be observed under microscope (e.g., FIG. 19). Swell ratio of the gels can be measured by comparing size data between monodisperse droplets in oil phase (100 minutes) and monodisperse beads in aqueous phase (5 minutes).

Experiment 5: Polymerization Using AIBN as Initiators

A copolymer poly(acrylamide) with click chemistry precursors attached can be synthesized through free radical solution polymerizations as follows: acrylamide monomers (50 mmol, a mixture of acrylamide and a derivative thereof comprising click chemistry moieties), NaF (1.6 M) and 2,2'-azobis[2-(2-imidazolin-2-yl)propane] dihydrochloride (VA-044, 0.05 mmol) can be dissolved in water. The mixture can be bubbled by nitrogen for half an hour and subjected to 30° C. to 40° C. for 24 hours. After cooling down to room temperature, the desired product can be obtained based on the solubility thereof in aqueous vs. organic solvents (hexane, EtOAc, and EtOH, etc.).

Example 2: Syntheses of a Propargylated Monomer and Co-Polymer

A propargyl-containing monomer 2D was synthesized as shown in Scheme 9. Propargyl alcohol was reacted with carbonyl-diimidazole to afford propargylating agent 2A, as shown. Mono-propargylation of cystamine 2B with propargylating agent 2A provided mono-propargylated cystamine 2C, which was further acylated on the free amine to provide disulfide-linked, propargylated monomer 2D. Monomer 2D is a degradable alkyne-containing monomer.

Copolymers with click chemistry precursors attached were synthesized through free radical solution polymerizations as following (see Scheme 10 and Scheme 11).

For a first co-polymer, acrylamide monomers (50 mmol, a mixture of acrylamide and monomer 2D), NaF (1.6 M) and 2,2'-azobis[2-(2-imidazolin-2-yl)propane] dihydrochloride (AIBN, 0.05 mmol) were dissolved in water. The mixture was bubbled with nitrogen for 30 minutes, then subjected to 30° C. to 40° C. for 24 hours. After cooling to room temperature, the desired product was obtained based on the solubility thereof in aqueous vs. organic solvents (hexane, EtOAc, EtOH, etc.).

Scheme 10

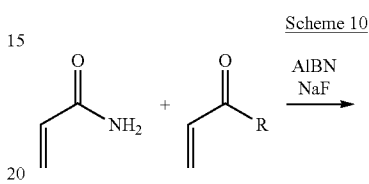

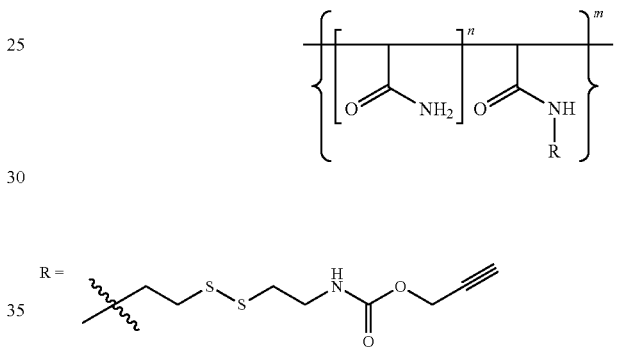

Scheme 9

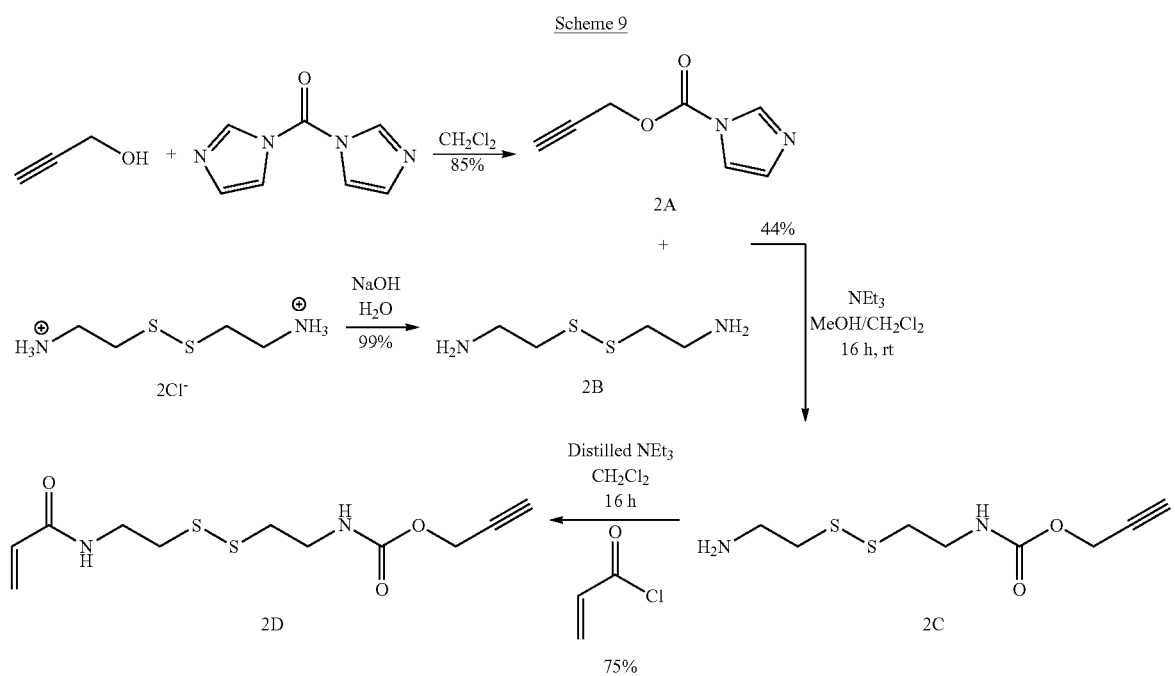

For a second co-polymer, poly(acrylamide) polymers and DMTMM were dissolved in water and the pH corrected to 7.5 with NaOH. 3-azido-1-propanamine was added and the solution was stirred at room temperature, protected from light, for about 16 hours. The product was purified by dialysis and lyophilized to afford the target co-polymer as a white solid.

Scheme 11

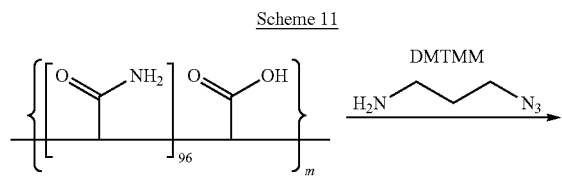

Example 3: Use of Cell Beads Generated with Click Chemistry for Single Cell DNA Sequencing Synthesis of azide and alkyne polymers was performed as described in Example 2.

Preparation of Copper (II) Reagent in the Oil Phase

1) Suspension of copper (II) salt. About 1.375 mM Krytox-COOH and about 1.25 mM Cu(OAc)$_2$ were stirred in HFE-7500 for about 48 hours at room temperature.

2) Preparation of GB Oil. GB Oil was prepared by mixing about 2.50 mM bis-Krytox-ethylene glycol-polymer (Krytox-PEG-Krytox or BKEP or Formula I) and about 0.25 mM Krytox in solvent HFE-7500 engineered oil. GB Oil was pre-formulated in bulk.

3) Preparation of the oil phase solution CB Oil. The suspension of copper (II) salt and the GB Oil were combined together in v/v=1:1 ratio, and the resulting mixture was stirred at room temperature for about 1 hour and filtered through a 0.22 μm PES filter to remove insoluble copper (II) salts. The filtrate was CB Oil comprising 1.25 mM BKEP, about 1.375 mM Krytox-COOH, and about 0.625 mM copper (II) in HFE-7500.

Preparation of the Aqueous Phase Solution

Stock solutions comprising sodium ascorbate were prepared by mixing polymer pairs of azide-containing (1.75% w/v) and alkyne-containing polymers (1.75% w/v), F-108 (0.5% w/v), magnetic particles (as indicated in Table 2), THPTA (1.00 mM) in water, sodium ascorbate (10.00 mM), and optionally DMSO (as indicated in Table 2) in water. Corresponding stock solutions without sodium ascorbate were generated for each sample type for use in cell bead generation (see below).

TABLE 2

| Sample Name | ST240_0.12 | ST240_0.12_DMSO | ONT500_0.12 | ONT500_0.12_DMSO | AN400_0.06 | AN400_0.06_DMSO |
|---|---|---|---|---|---|---|
| Magnetic Particles (type) | Sphere™ Carboxyl Magnetic Particles | Sphere™ Carboxyl Magnetic Particles | Ocean Nanotech-Mono Mag | Ocean Nanotech-Mono Mag carboxylic acid beads | AccuNano Bead™ COOH Magnetic Nanobeads | AccuNano Bead™ COOH Magnetic Nanobeads |
| Magnetic Particles (% w/v) | .12 | .12 | .12 | .12 | .06 | .06 |
| DMSO (% w/v) | 0 | 5 | 0 | 5 | 0 | 5 |

-continued

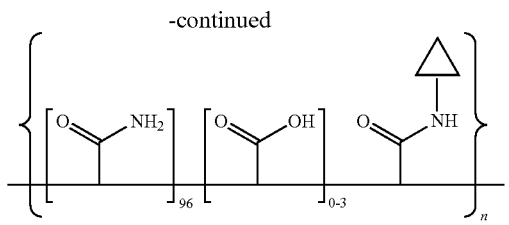

Click Chemistry and Gelation in the Presence of Cells

To make emulsions of discrete droplets, an equipment setup similar to that depicted in FIG. 7 can be employed. Specifically, stock solutions with sodium ascorbate (60 μL) and BJ cells (ATCC) were fed through a first channel (e.g., 701); the corresponding stock solution without sodium ascorbate (40 μL) was fed through a second channel (e.g., 702); and Copper-free oil (270 μL) was fed through a third channel (e.g., 704). A collection of water-in-oil emulsions of droplets was obtained in a collecting well. The emulsions of droplets were kept in the well (with a cover) for about 15 minutes with shaking at 1000 rpm. Then, CB Oil was added to a final copper concentration of 0.9 mM. The emulsions of droplets were kept in the well for an additional 45 minutes with shaking at 1000 rpm. Subsequent solvent exchange was used to convert the oil phase into an aqueous phase (5 mM EDTA). Gels were washed in phosphate-buffered-saline (3×), thereby generating cell beads. Gelation was observed visually and under microscope.

DNA Sequencing

Resultant cell beads were processed for DNA sequencing as described elsewhere herein. Briefly, cell beads were partitioned into droplets with barcode beads, lysed, and DNA from the cells was barcoded. Resultant barcoded DNA was isolated and subjected to nucleic acid sequencing. Nucleic acid sequencing results for each sample were analyzed and compared to target specifications for optimal cell bead performance. Results of this analysis are shown in Table 3.

TABLE 3

| Sample Description | Target Spec | ST240_0.12 | ST240_0.12_DMSO | ONT500_0.12 | ONT500_0.12_DMSO | AN400_0.06 | AN400_0.06_DMSO |
|---|---|---|---|---|---|---|---|
| Cells detected | | 131 | 125 | 224 | 183 | 165 | 169 |
| Fraction Observed Barcodes on Whitelist | ≥0.85 | 0.85 | 0.87 | 0.85 | 0.84 | 0.85 | 0.86 |
| Total Wasted Data | ≤0.40 | 0.71 | 0.83 | 0.65 | 0.69 | 0.51 | 0.46 |
| Fraction Reads in Empty Barcodes | ≤0.10 | 0.16 | 0.22 | 0.12 | 0.16 | 0.09 | 0.08 |
| Amp Rate Cell Barcodes Median | ≥0.11 | 0.04 | 0.03 | 0.03 | 0.04 | 0.08 | 0.14 |
| Amp Rate CV | | 0.43 | 0.45 | 0.42 | 0.49 | 0.49 | 0.44 |
| DPCV Cell Barcodes Median Unnormalized | ≤0.13 | 0.11 | 0.11 | 0.1 | 0.11 | 0.1 | 0.1 |
| Fraction of cells with dpcv < 0.2 | ≥0.97 | 0.98 | 0.97 | 0.99 | 0.98 | 0.97 | 0.97 |
| Fraction of cells dpcv < 0.15 | ≥0.90 | 0.91 | 0.94 | 0.96 | 0.9 | 0.95 | 0.92 |
| Technical noise fraction | ≤0.15 | 0.05 | 0.08 | 0.05 | 0.11 | 0.1 | 0.11 |
| GC bias metric (cells only) | ≤0.08 | 0.04 | 0.03 | 0.03 | 0.03 | 0.04 | 0.03 |
| Diffusion Dup Rate Full Coverage | ≤0.10 | 0.08 | 0.09 | 0.08 | 0.08 | 0.07 | 0.06 |
| Dup Ratio Cell Barcodes Median | | 1.43 | 1.56 | 1.39 | 1.39 | 1.19 | 1.13 |
| Fraction reads non-whitelist barcodes | | 0.15 | 0.13 | 0.15 | 0.16 | 0.15 | 0.14 |
| Median mapQ 30 fraction in cells | | 0.6 | 0.55 | 0.61 | 0.62 | 0.72 | 0.76 |

Figure 20:
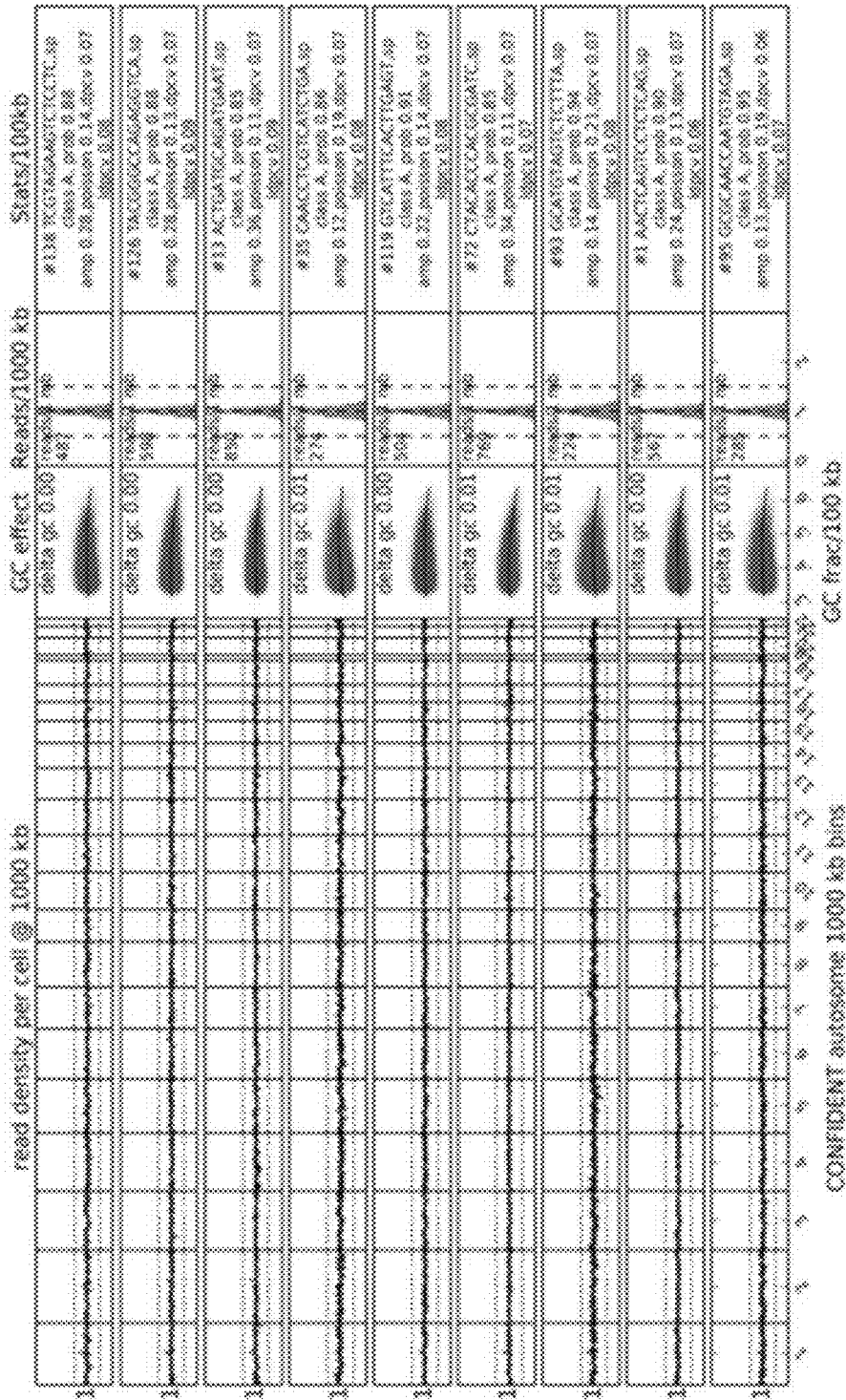
FIG. 20 shows experimental sequencing results from DNA obtained from a cell comprised in a cell bead.

FIG. 20 shows sequencing results from one sample, AN400_0.06_DMSO, demonstrating high quality sequencing results using these conditions.

Example 4: Cell Centering

Synthesis of azide and alkyne polymers was performed as described in Example 2.

Preparation of Copper (II) Reagent in the Oil Phase

1) Suspension of copper (II) salt. About 1.375 mM Krytox-COOH and about 1.25 mM Cu(OAc)$_2$ were stirred in HFE-7500 for about 48 hours at room temperature.

2) Preparation of GB Oil. GB Oil was prepared by mixing about 2.50 mM bis-Krytox-ethylene glycol-polymer (Krytox-PEG-Krytox or BKEP or Formula I) and about 0.25 mM Krytox in solvent HFE-7500 engineered oil. GB Oil was pre-formulated in bulk.

3) Preparation of the oil phase solution CB Oil. The suspension of copper (II) salt and the GB Oil were combined together in v/v=1:1 ratio, and the resulting mixture was stirred at room temperature for about 1 hour and filtered through a 0.22 μm PES filter to remove insoluble copper (II) salts. The filtrate was CB Oil comprising 1.25 mM BKEP, about 1.375 mM Krytox-COOH, and about 0.625 mM copper (II) in HFE-7500.

Preparation of the Aqueous Phase Solution

Stock solutions comprising sodium ascorbate were prepared by mixing polymer pairs of azide-containing (1.75% w/v) and alkyne-containing polymers (1.75% w/v), F-108 (0.5% w/v), magnetic particles (0.12% w/v), THPTA (1.00 mM) in water, and sodium ascorbate (150.00 mM) in water. Corresponding stock solutions without sodium ascorbate were generated for each sample type for use in cell bead generation (see below).

Click Chemistry and Gelation in the Presence of Cells

Figure 21A:
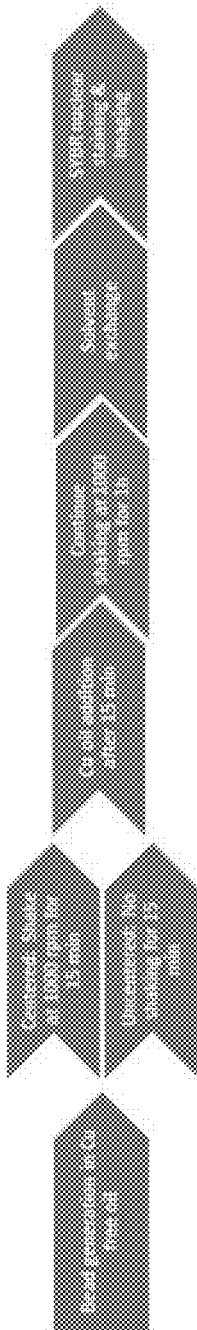
FIG. 21A diagrams an example workflow for generating cell beads.
Figure 21C:
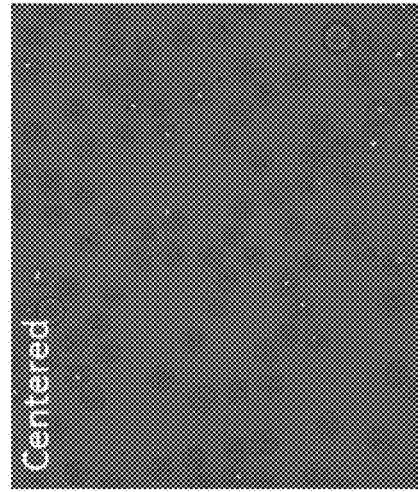
FIG. 21C shows imaging results from cell beads generated with cell centering.

To make emulsions of discrete droplets, an equipment setup similar to that depicted in FIG. 7 can be employed. Specifically, stock solutions with sodium ascorbate (60 μL)

and peripheral blood mononuclear cells (PBMCs) obtained from a subject were fed through a first channel (e.g., 701); the corresponding stock solution without sodium ascorbate (40 µL) was fed through a second channel (e.g., 702); and Copper-free oil (270 µL) was fed through a third channel (e.g., 704). A collection of water-in-oil emulsions of droplets was obtained in a collecting well. The emulsions of droplets were separated into two sets of wells and processed via the workflow shown in FIG. 21A. One set of emulsions was covered for about 15 minutes with shaking at 1000 rpm to facilitate cell centering. The second set was covered for about 15 minutes with no shaking. Then, CB oil was added to a final copper concentration of 0.625 mM. The emulsions of droplets were kept in the wells for an additional 45 minutes with shaking at 1000 rpm. Subsequent solvent exchange was used to convert the oil phase into an aqueous phase (5 mM EDTA). Gels were washed in phosphate-buffered-saline (3×), thereby generating cell beads. Gelation was observed visually and under microscope.

Nuclear Staining and Imaging

Figure 21B:
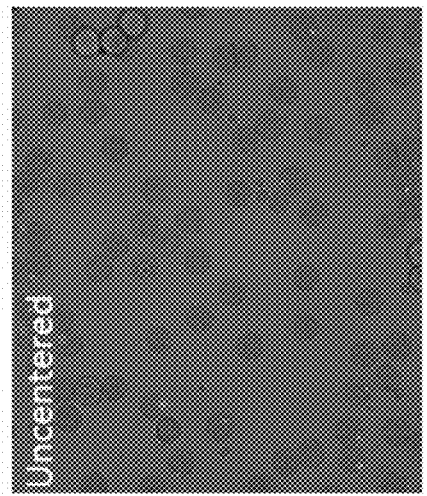
FIG. 21B shows imaging results from cell beads generated without cell centering.
Figure 22:
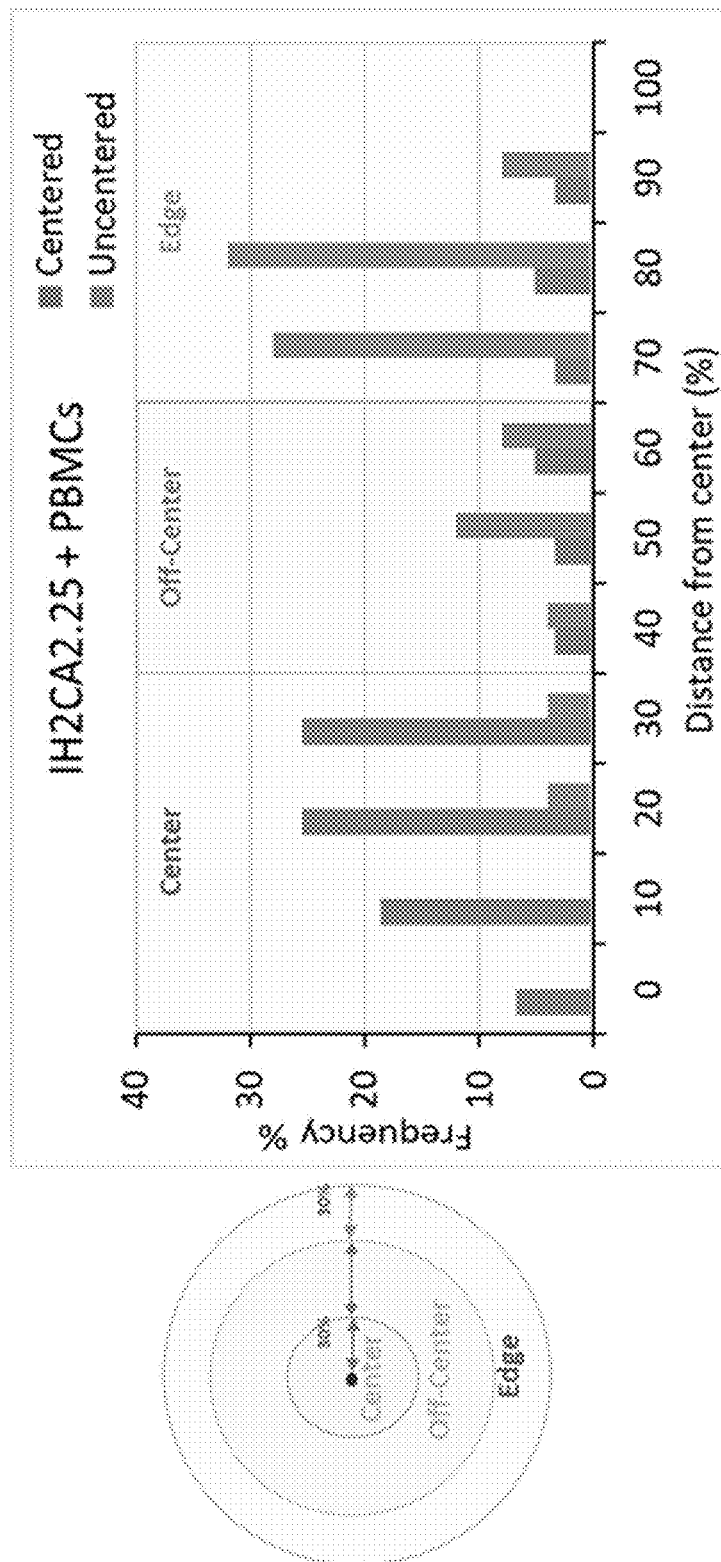
FIG. 22 shows a graph of results from the cell centering experiments of Example 4.

Cell beads were stained with SYBR® nuclear staining and imaged using a fluorescent microscope. Imaging results are shown in FIG. 21B (uncentered) and 21C (centered). FIG. 22 shows the results of cell centering analysis, demonstrating that the emulsions which underwent the centering procedure (shaking) generated a greater number of cell beads with cells near the center of the bead as compared with those that did not undergo the centering procedure.

Example 5: Cell Bead Generation Parameters Impact DNA Degradation

Figure 23:
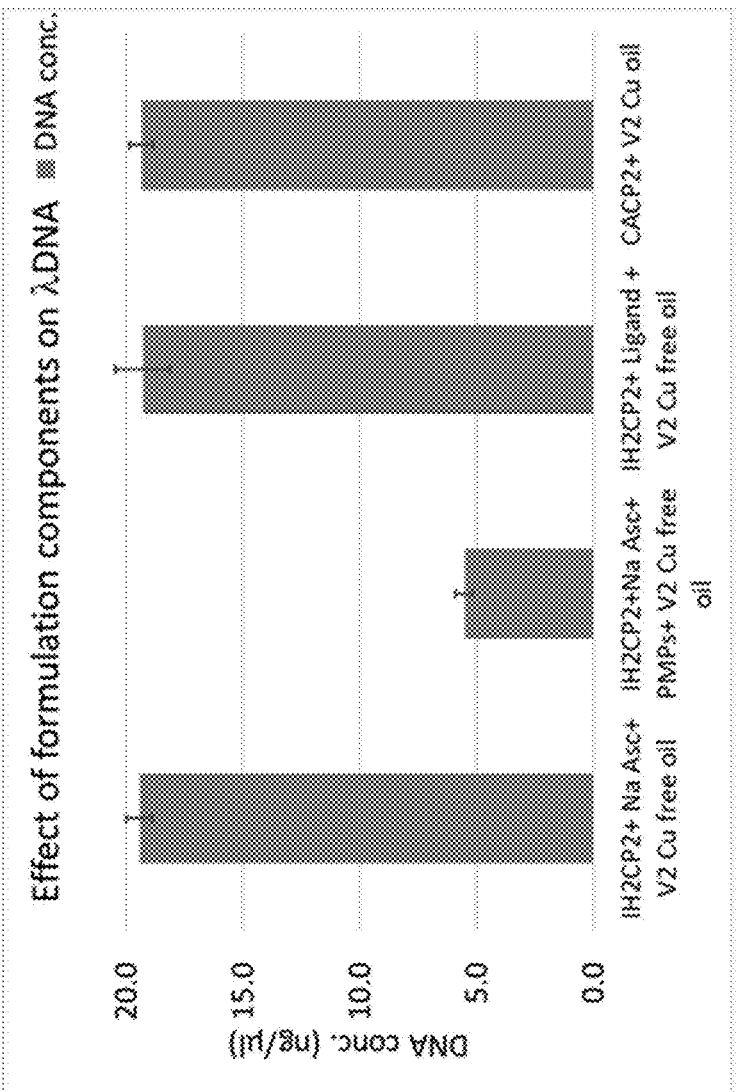
FIG. 23 shows a graph of results from the cell bead generation experiments of Example 5.

Emulsions were generated comprising azide and alkyne-comprising polymers, λDNA, and the additional components as indicated in FIG. 23. Sodium ascorbate as provided at 150 mM. Each was generated using copper-free oil. λDNA concentration from each was measured by quantitative PCR (qPCR). These results indicate a reduction in λDNA concentration, due to DNA degradation, in the presence of paramagnetic particles (PMPs) and sodium ascorbate (Na Asc). Removal of PMPs from the conditions eliminates DNA degradation.

Example 6: DMSO Addition and/or PMP Choice Impacts DNA Degradation

Figure 24:
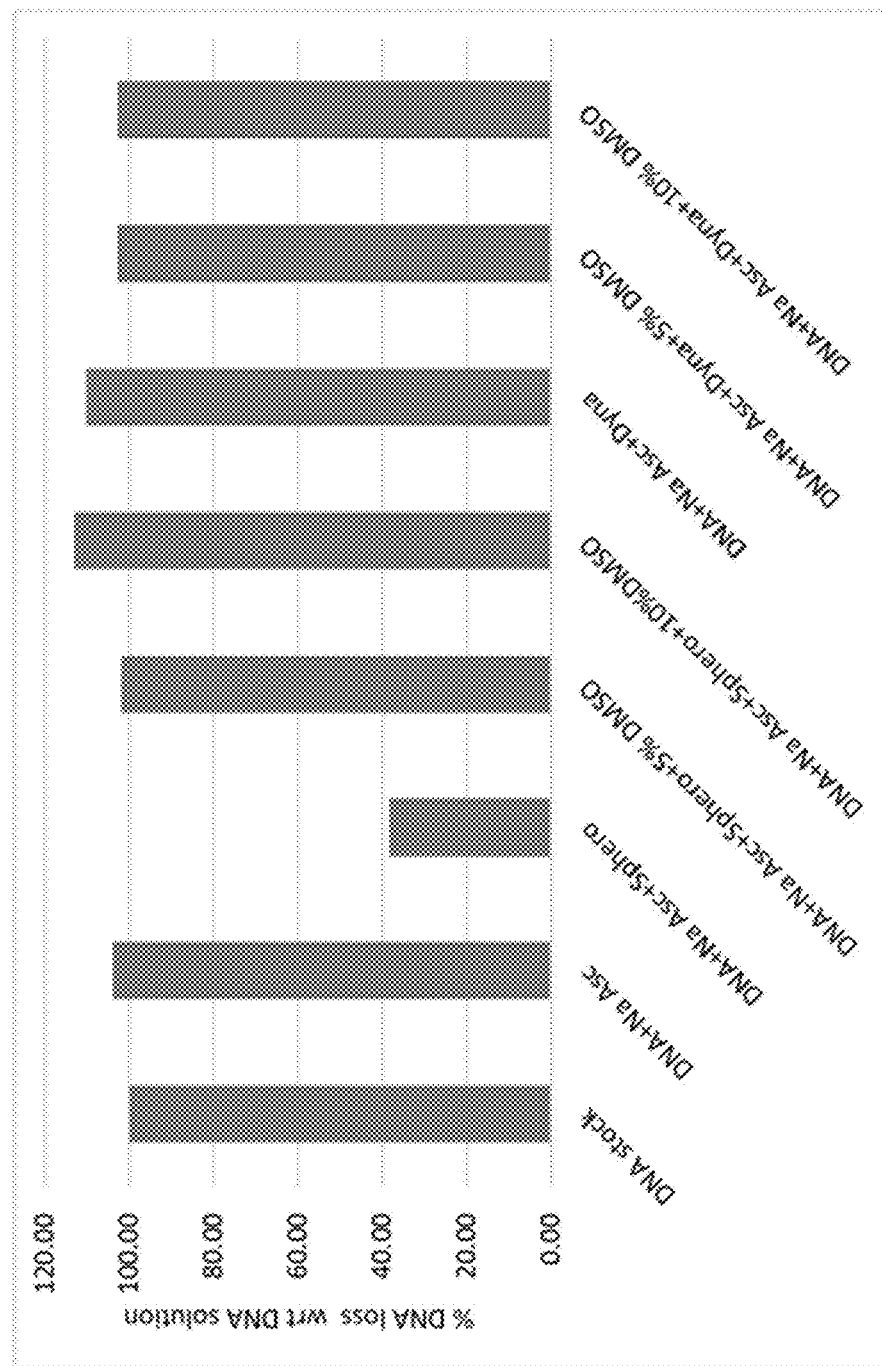
FIG. 24 shows a graph of results from the cell bead generation experiments of Example 6.

Emulsions were generated comprising azide and alkyne-comprising polymers, DNA, and the additional components as indicated in FIG. 24. Each was generated using copper-containing oil. Sodium ascorbate was provided at 10 mM. Two different PMPs were tested; Sphero™ Carboxyl Magnetic Particles (Sphero), which comprise an iron oxide coating surrounding a polystyrene core, and Dynabeads magnetic beads (Dyna), which comprise an iron oxide core surrounded by an outer polymer coating, each in different concentrations of DMSO as indicated in FIG. 24. These results indicate that the use of Dynabeads and addition of at least 5% DMSO can prevent DNA degradation.

Example 7: Cell Bead Generation with CuAcAc

The use of copper (II) hexafluoroacetylacetonate (CuAcAc) as a copper source for click chemistry-mediated cell bead generation was tested under different parameters.

Figure 25A:
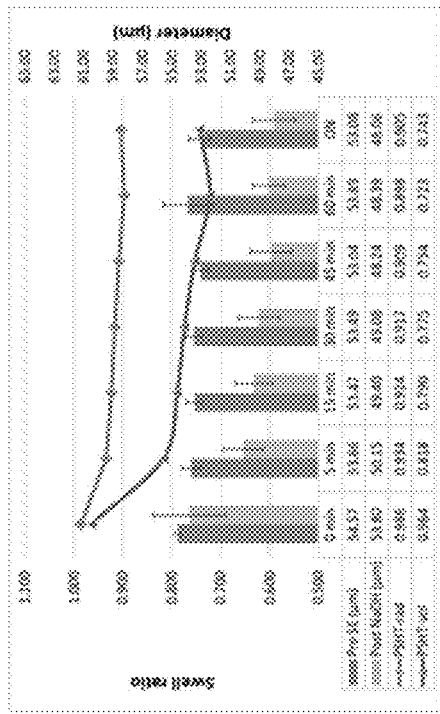
FIG. 25A shows the results from a cell bead generation experiment described in Example 7 comprising the use of varying sodium ascorbate concentrations.

FIG. 25A shows the results of cell bead generation using varying sodium ascorbate (Na Asc) concentrations, ranging from 10 mM to 200 mM. Cell beads were generated as described herein using the following parameters: 1 mM THPTA, 1 mM CuAcAc, and 2.5 mM KmPEG oil. These results demonstrate that 100 mM of sodium ascorbate provides optimal cell bead generation under these conditions.

Figure 25B:
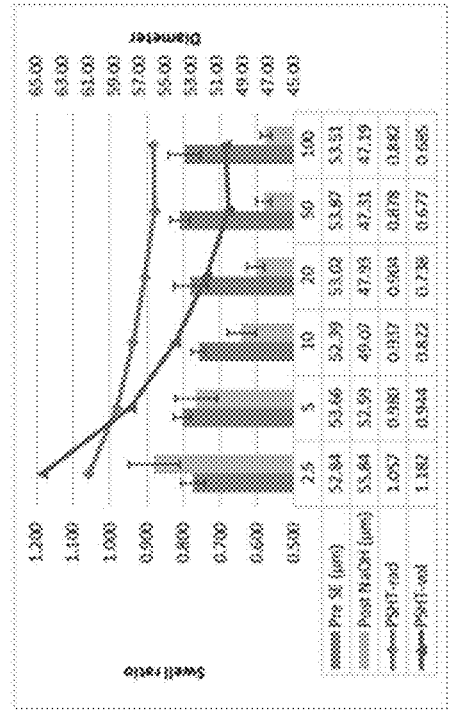
FIG. 25B shows the results from a cell bead generation experiment described in Example 7 comprising the use of varying gelation times.

FIG. 25B shows the results of cell bead generation using varying gelation times, ranging from 0 minutes to overnight (ON). Cell beads were generated as described herein using the following parameters: 1 mM THPTA, 1 mM CuAcAc, 2.5 mM KmPEG oil, and 100 mM sodium ascorbate. These results demonstrate that 60 minutes of gelation time is the minimum needed to achieve optimal cell bead generation under these conditions.

Figure 25C:
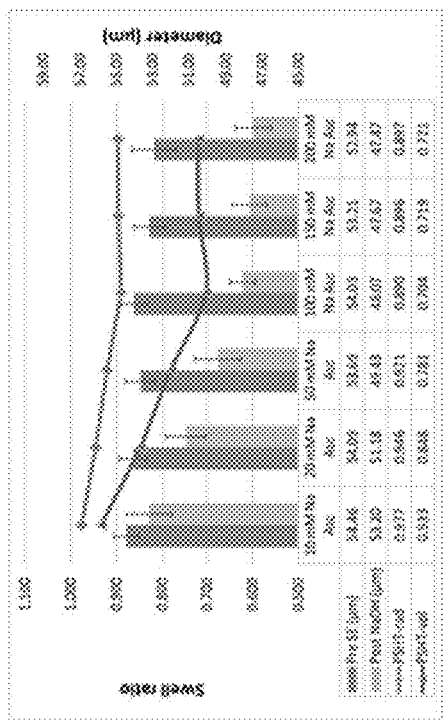
FIG. 25C shows the results from a cell bead generation experiment described in Example 7 comprising the use of varying THPTA concentrations.

FIG. 25C shows the results of cell bead generation using varying THPTA concentrations, ranging from 0.5 mM to 8 mM. Cell beads were generated as described herein using the following parameters: 1 mM CuAcAc, 2.5 mM KmPEG oil, and 20 mM sodium ascorbate. These results demonstrate that 5 mM of THPTA provides optimal cell bead generation under these conditions.

Figure 25D:
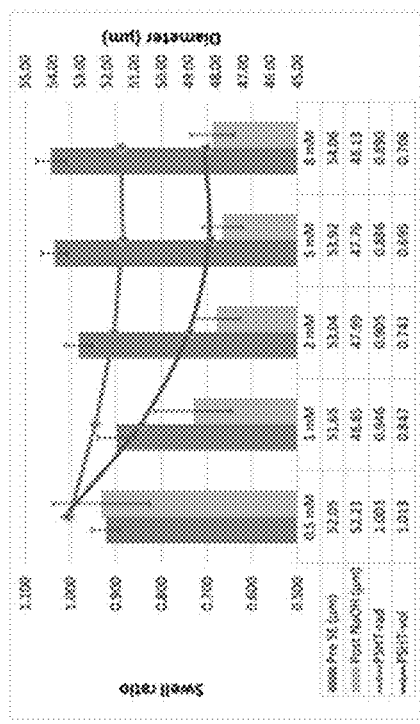
FIG. 25D shows the results from a cell bead generation experiment described in Example 7 comprising the use of varying sodium ascorbate concentrations.

FIG. 25D shows the results of cell bead generation using varying sodium ascorbate (Na Asc) concentrations, ranging from 2.5 mM to 100 mM. Cell beads were generated as described herein using the following parameters: 5 mM THPTA, 1 mM CuAcAc, and 2.5 mM KmPEG oil. These results demonstrate that 50 mM of sodium ascorbate provides optimal cell bead generation under these conditions.

Figure 26B:
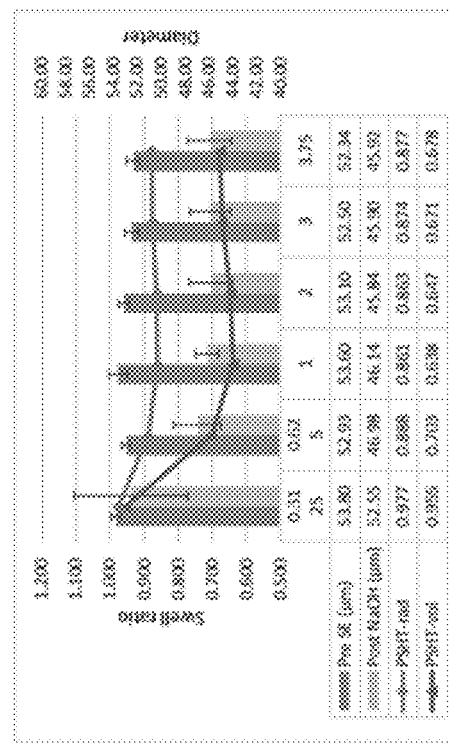
FIG. 26B shows the results from a cell bead generation experiment described in Example 7 comprising the use of varying gelation times.
Figure 26A:
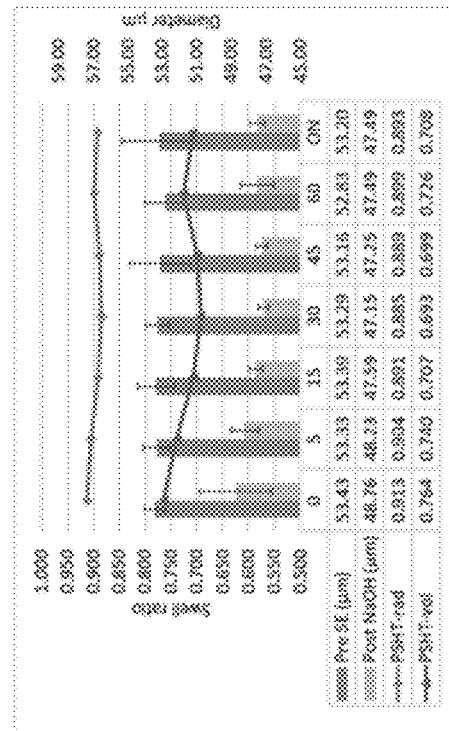
FIG. 26A shows the results from a cell bead generation experiment described in Example 7 comprising the use of varying CuAcAc concentrations.

FIG. 26A shows the results of cell bead generation using varying CuAcAc concentrations, ranging from 0.3125 mM to 3.75 mM. Cell beads were generated as described herein using the following parameters: 5 mM THPTA, 2.5 mM KmPEG oil, and 20 mM sodium ascorbate. These results demonstrate that 1 mM of CuAcAc provides optimal cell bead generation under these conditions.

FIG. 26B shows the results of cell bead generation using varying gelation times, ranging from 0 minutes to overnight (ON). Cell beads were generated as described herein using the following parameters: 5 mM THPTA, 1 mM CuAcAc, 2.5 mM KmPEG oil, and 50 mM sodium ascorbate. These results demonstrate that 15 minutes of gelation time is the minimum needed to achieve optimal cell bead generation under these conditions.

Table 4 shows the parameters identified as optimal for cell bead generation using CuAcAc, requiring only 15 minutes of gelation time.

TABLE 4

| Component | Final concentration |
|---|---|
| Azide Polymer mix | 1.75% w/v |
| Alkyne Polymer mix | 1.75% w/v |
| F-108 | 0.50% w/v |
| Mag. Particles (PMPs) | 0.12% w/v |
| Ligand (THPTA) | 5.00 mM |
| Reducing agent (Na Asc). | 50.00 mM |
| Additive (DMSO) | 5% v/v |

Example 8: Cell Bead Generation with $Cu_2OAc$

The use of copper acetate ($Cu_2OAc$) as a copper source for click chemistry-mediated cell bead generation was tested under different parameters.

FIG. 27A shows the results of cell bead generation using varying THPTA concentrations, ranging from 0.05 mM to 8 mM. Cell beads were generated as described herein using the following parameters: 5 mM sodium ascorbate, 0.625 mM $Cu_2OAc$, and 2.5 mM KmPEG oil. These results demonstrate that 1 mM of THPTA provides optimal cell bead generation under these conditions. No gelation was observed for THPA concentrations of 0.05 mM, 5 mM, and 8 mM.

FIG. 27B shows the results of cell bead generation using varying sodium ascorbate (Na Asc) concentrations, ranging from 2.5 mM to 100 mM. Cell beads were generated as described herein using the following parameters: 1 mM THPTA, 0.625 mM $Cu_2OAc$, and 2.5 mM KmPEG oil. These results demonstrate that 50 mM of sodium ascorbate provides optimal cell bead generation under these conditions.

FIG. 27C shows the results of cell bead generation using varying sodium ascorbate (Na Asc) concentrations, ranging from 2.5 mM to 100 mM. Cell beads were generated as described herein using the following parameters: 1 mM THPTA, 1 mM $Cu_2OAc$, and 2.5 mM KmPEG oil. These results demonstrate that 20 mM of sodium ascorbate provides optimal cell bead generation under these conditions.

FIG. 27D shows the results of cell bead generation using varying sodium ascorbate (Na Asc) concentrations, ranging from 2.5 mM to 100 mM. Cell beads were generated as described herein using the following parameters: 1 mM THPTA, 2 mM $Cu_2OAc$, and 2.5 mM KmPEG oil. These results demonstrate that 20 mM of sodium ascorbate provides optimal cell bead generation under these conditions.

Figures 28A, 28B:
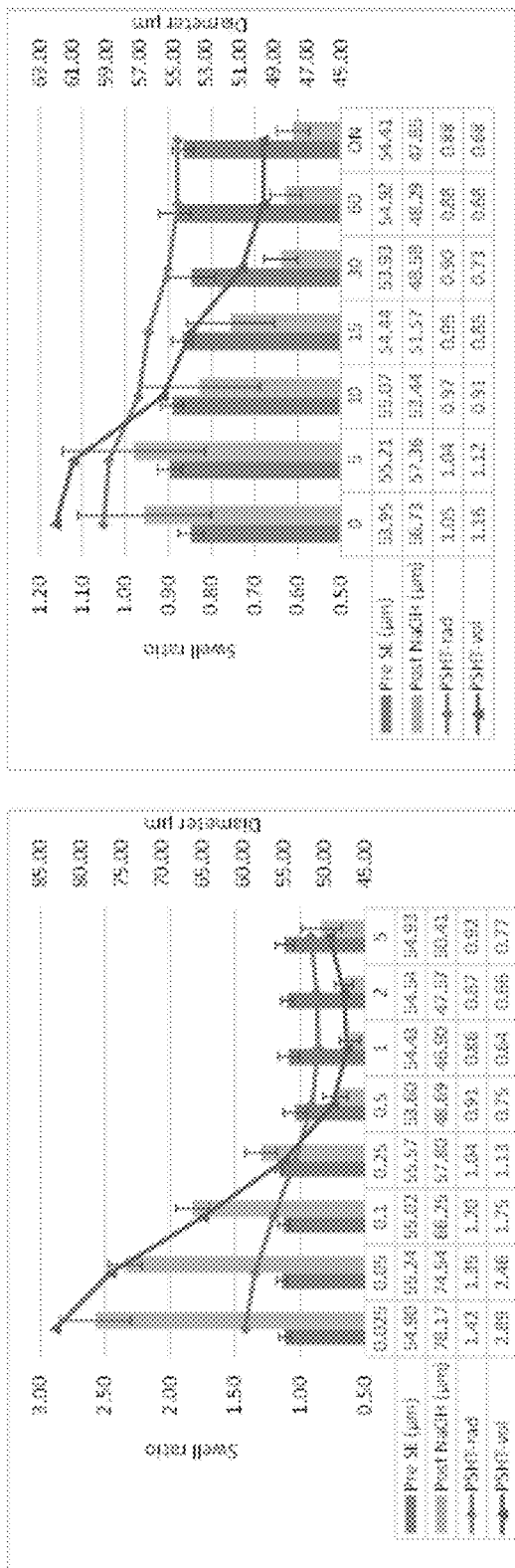
FIG. 28A shows the results from a cell bead generation experiment described in Example 8 comprising the use of varying THPTA concentrations.
FIG. 28B shows the results from a cell bead generation experiment described in Example 8 comprising the use of varying gelation times.

FIG. 28A shows the results of cell bead generation using THPTA concentrations, ranging from 0.025 mM to 5 mM. Cell beads were generated as described herein using the following parameters: 2 mM $Cu_2OAc$, 20 mM sodium ascorbate, and 2.5 mM KmPEG oil. These results demonstrate that 1 mM of THPTA provides optimal cell bead generation under these conditions.

FIG. 28B shows the results of cell bead generation using varying gelation times, ranging from 0 minutes to overnight (ON). Cell beads were generated as described herein using the following parameters: 1 mM THPTA, 2 mM $Cu_2OAc$, 2.5 mM KmPEG oil, and 20 mM sodium ascorbate. These results demonstrate that 30 minutes of gelation time is the minimum needed to achieve optimal cell bead generation under these conditions.

Table 5 shows the parameters identified as optimal for cell bead generation using $Cu_2OAc$, requiring only 30 minutes of gelation time.

TABLE 5

| Component | Final concentration |
| --- | --- |
| Azide Polymer mix | 1.75% w/v |
| Alkyne Polymer mix | 1.75% w/v |
| F-108 | 0.50% w/v |
| Mag. Particles (PMPs) | 0.12% w/v |
| Ligand (THPTA) | 1.00 mM |
| Reducing agent (Na Asc). | 20.00 mM |
| Additive (DMSO) | 5% v/v |

Example 9: Generation of Copper Nanoparticle/Cell Complexes

Copper nanoparticles (CuNPs) were obtained from US Research Nanomaterials Inc. 10 mg of CuNPs were suspended in 1 mL of complete cell culture medium. CuNPs were sonicated for 2 minutes, then vortexed for 10 minutes. 10 mL of complete cell culture medium was added to the CuNP suspension and centrifuged for 5 minutes at 150 g to remove large particles. Supernatant was collected and centrifuged for 5 minutes at 1000 g. Supernatant was discarded, and the pellet was resuspended in 1 mL of complete cell culture medium. The resultant CuNP suspension was sonicated in a bath sonicator for 30 minutes.

Next, cells were resuspended in complete cell medium at $10^7$ cells per mL. 1 mL of CuNP dispersion was added to the cell suspension and incubated for 15 minutes at 4° C. Then, the mixture was centrifuged for 5 minutes at 50 g, 4° C., mixed gently, and centrifuged again using the same conditions. The cell pellet was washed two times with 10 mL complete cell culture medium, with a centrifugation at 20 g, 4° C. and removal of supernatant following each wash. Finally, the CuNPs/cell mixture was resuspended in 500 μL complete medium for cell bead generation.

Example 10: Use of Copper Nanoparticles for Cell Bead Generation

The CuNP/cell mixture is partitioned into droplets as described herein, together with polymers for cell bead generation. Polymers in droplets comprising a cell/CuNPs complex are cross-linked via click chemistry, using the CuNPs as a catalyst, thereby generating cell beads. Polymers in droplets which do not comprise a cell/CuNPs complex are not cross-linked. A population of cell beads is generated.

Example 11: Low Copper Concentration Cell Bead Generation Using Picolyl Polymers This example illustrates how cell beads (CBs) can be generated from emulsions of discrete droplets at low copper concentrations by using polymers having a copper-chelating azido-picolyl functionality. As depicted schematically in FIG. 29, and described elsewhere herein, linkers modified with an azido-picolyl functionality can undergo a copper-catalyzed click reaction with an alkyne-modified linker to form a crosslink comprising a 1,2,3-triazole click chemistry linkage. Further, the ability of the azido-picolyl functionality to chelate copper ion effectively raises the copper concentration at the site of the copper-catalyzed click reaction. This increase in effective copper concentration at the reaction site allows for a reduction in the overall copper concentration in the reaction without a loss in the cross-linking efficiency. A reduction in overall copper concentration in the cell bead generation process significantly improves biocompatibility, e.g., degradation of RNA components.

Two sets of CBs were generated from emulsions of discrete droplets according to the methods described in Example 3. One set of CBs included polymers having azido-picolyl functionality whereas the other set had polymers having the standard azide functionality. The generation of the two sets of CBs was carried out by copper catalyzed click chemistry at a range of copper concentrations from 0.0625 mM to 0.625 mM. The size of the CBs generated under the different copper concentration conditions were determined via microscopy.

Figure 31A:
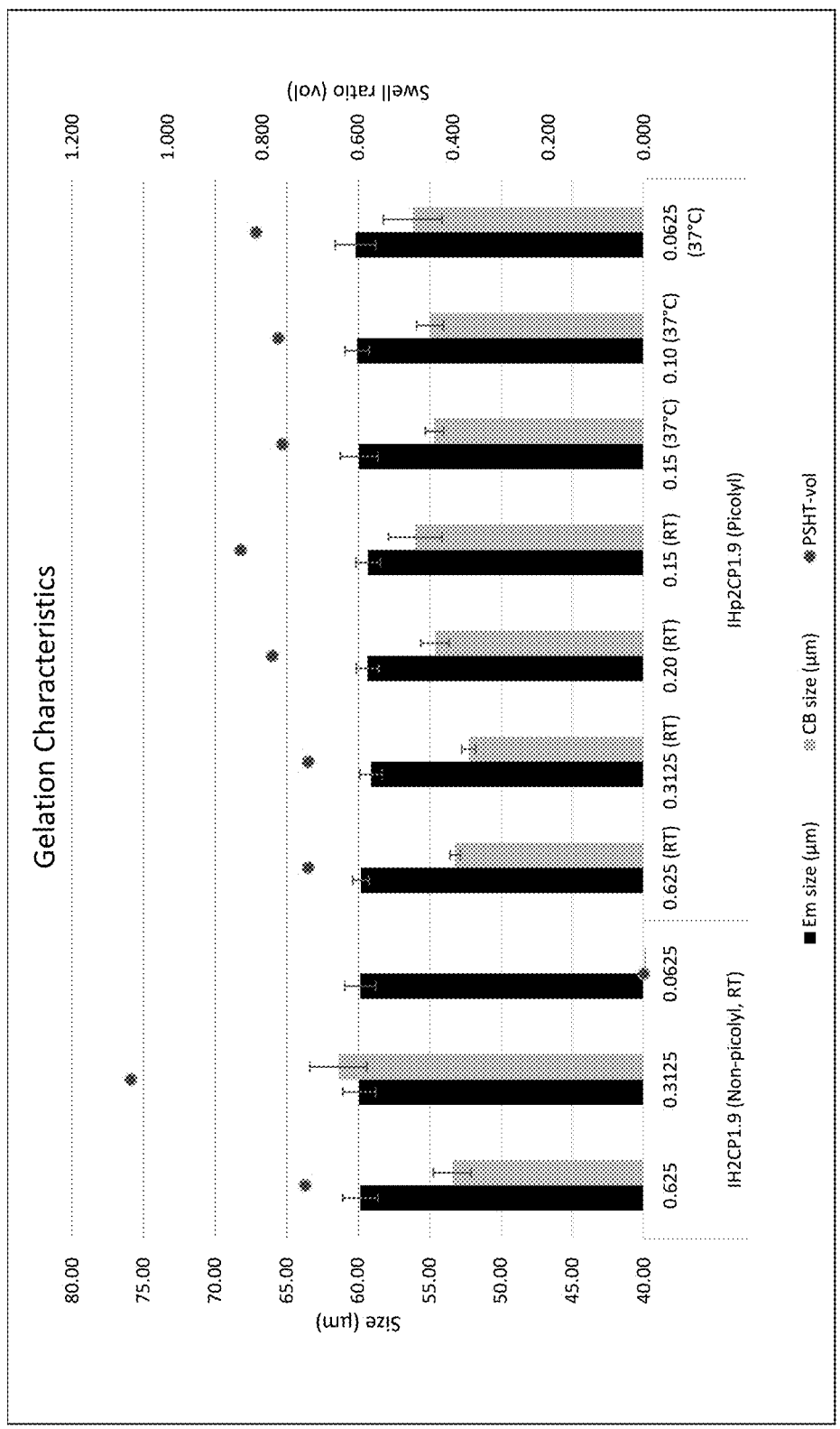
FIG. 31A shows results of low-copper concentration click chemistry crosslinking using azide-picolyl modified linkers as described in Example 11.

As shown in FIG. 31A, significant differences were observed in CBs formed using the picolyl polymer and those formed using the standard non-picolyl polymer. The picolyl polymer CBs exhibited no change in swell-ratio (SR) upon reducing Cu concentration in half (from 0.625 mM to 0.3125 mM). Moreover, the picolyl polymer CBs could be generated using a Cu concentration of 0.0625 mM in oil at 37 C in only 30 minutes and exhibited only a small increase in SR from 0.70 to 0.81. In contrast, the non-picolyl polymer CBs could not be generated at a Cu concentration of 0.0625 mM and even a decrease from 0.625 mM to 0.3125 mM Cu concentration resulted in a significant increase in CB swell-ratio from 0.70 to 1.07.

A further experiment was carried out in which CBs were generated from emulsion of droplets containing GM12878 cells dispersed in a polymer mix containing either polymers with an azido-picolyl functionality at low Cu concentration (0.15 mM or 0.20 mM) or polymers with an azido-alkyl (i.e., non-picolyl) functionality and higher Cu concentration (0.625 mM). Gelation within the droplets was carried out for 45 min at RT under the following conditions for the droplets containing the picolyl or non-picolyl polymers: (a) picolyl polymers: 0.15 mM Cu, 8 mM sodium ascorbate; or 0.20 mM Cu, 10 mM sodium ascorbate; (b) non-picolyl polymers: 0.625 mM Cu, 10 mM sodium ascorbate. Following gelation, the emulsion was broken, and the resulting CBs were washed twice in PBS, and then packed by centrifugation. Equivalent volumes of the distinct sets CBs (depending on copper concentration) were added to a 3'RT mix and the standard "Single Cell 3' v2" protocol was carried out to generate cDNA products (10× Genomics, Pleasanton, CA, USA). DTT in the 3'RT mix was used to degrade the disulfide crosslinks of the hydrogel matrix and thereby dissolve the CBs.

Figure 31B:
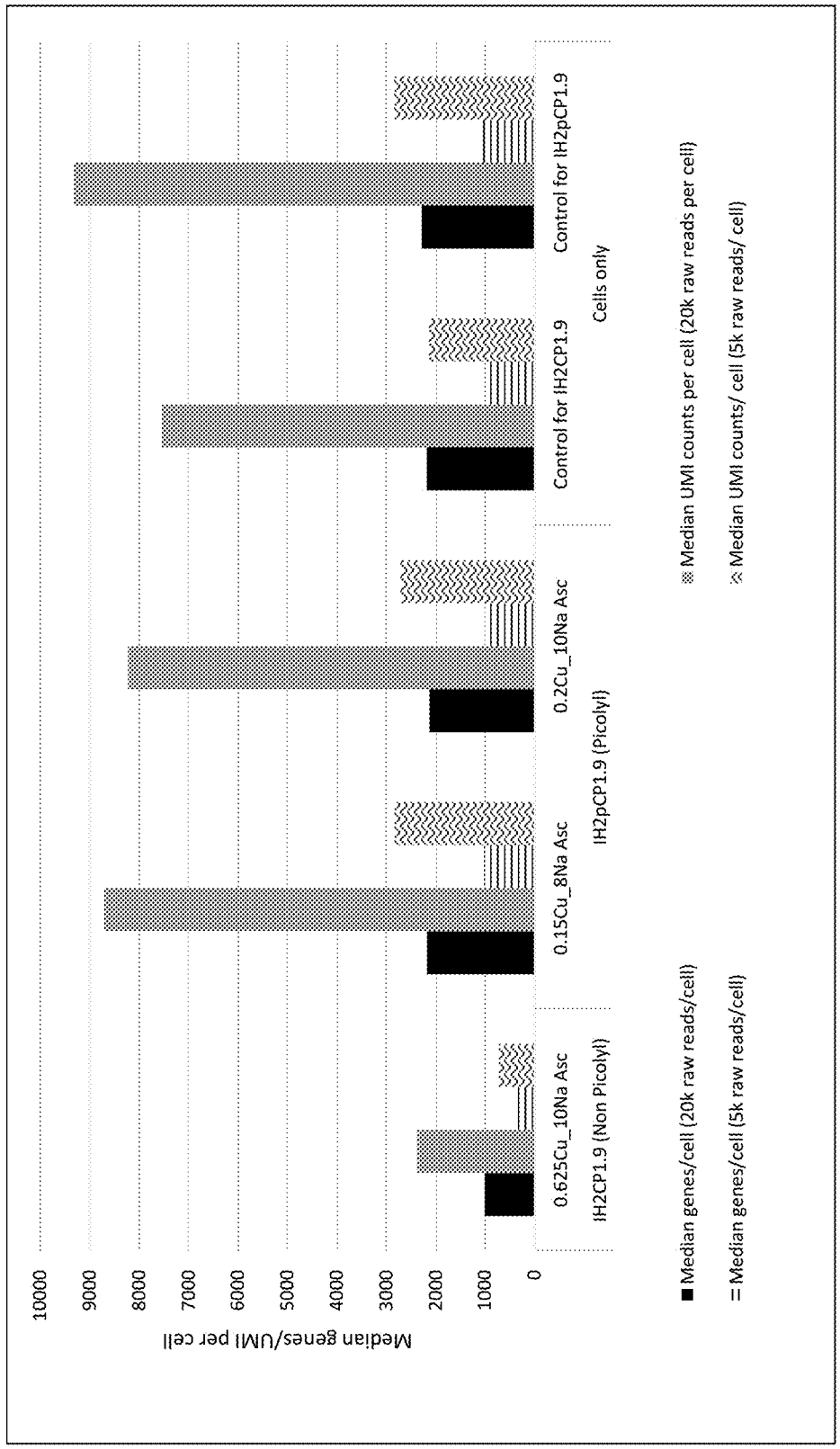
FIG. 31B shows results of low-copper concentration click chemistry crosslinking using azide-picolyl modified linkers as described in Example 11.

As shown by the results depicted in FIG. 31B, in the CBs formed via click chemistry crosslinking of polymers with azido-picolyl functionality and lower copper concentrations (0.15 mM or 0.2 mM), ~95% of genes and ~94% of unique molecular identifiers (UMI) were detected relative to cell control. In contrast, in the CBs formed using non-picolyl polymers and a higher copper concentration (0.625 mM), only 45% of genes and only 33% of UMI were detected relative to cell control.

In summary, the ability to use substantially lower Cu concentrations during gelation of discrete droplets to form CBs can be carried out by incorporating polymers with the azido-picolyl functionality. The use of lower copper concentration in forming the CBs results in substantially decreased RNA degradation and substantially improved gene detection.

Example 12: Chemical Degradation Cell Beads with Carbamate Linkages

This example illustrates how CBs generated from emulsions of discrete droplets with labile carbamate (rather than disulfide) linkages can be selectively degraded with diethyltriamine (DETA) and heat.

Emulsions of discrete droplets are generated with polymers modified with linkers including either azide or alkyne groups capable of undergoing CuAAC click chemistry. As illustrated by the scheme depicted in FIG. 32, the linkers with the alkyne group comprise a propargyl-carbamate moiety that undergoes copper catalyzed click chemistry crosslinking reaction with the azide linker modified polymer to form the gel matrix. The crosslinks forming the gel matrix comprise a 1,2,3-triazole moiety but do not include a disulfide linkage. Thus, they are no susceptible to degradation by DTT treatment. Instead, the crosslinks can be degraded by treatment with a polyamine (e.g., DETA) and heat (e.g., 60° C.) which acts to cleave the carbamate group as shown in FIG. 32.

Figure 32:
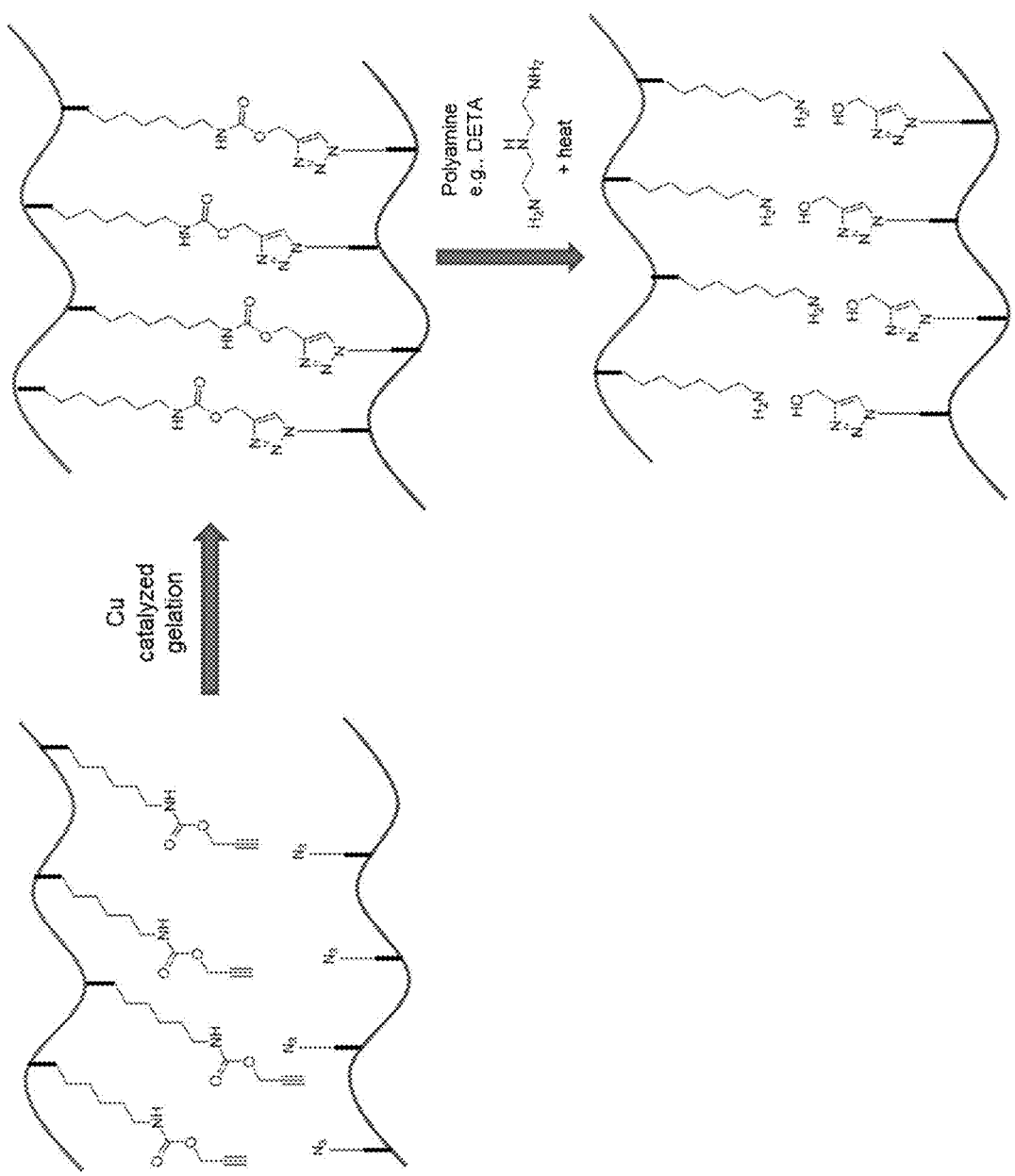
FIG. 32 shows an exemplary click chemistry crosslinking reaction to form crosslinks with a labile carbamate bond, and subsequent cleavage of the carbamate with DETA and heat.

CBs were generated from an emulsion of droplets as described in Example 3 except that linkers comprising a propargyl-carbamate moiety (and no disulfide linkage) as shown in FIG. 32. The resulting CBs comprising a carbamate linkage were analyzed for their degradation characteristics in the presence of DETA and heat. Degradation was monitored using optical microscopy. 30 μL of the carbamate CBs were exposed to 200 μL solution of 10% DETA in PBS at 60° C. and compared to carbamate CBs exposed to a control PBS solution without DETA. The carbamate CBs were completely degraded after 15 minutes in 10% DETA at 60° C.

Figure 33:
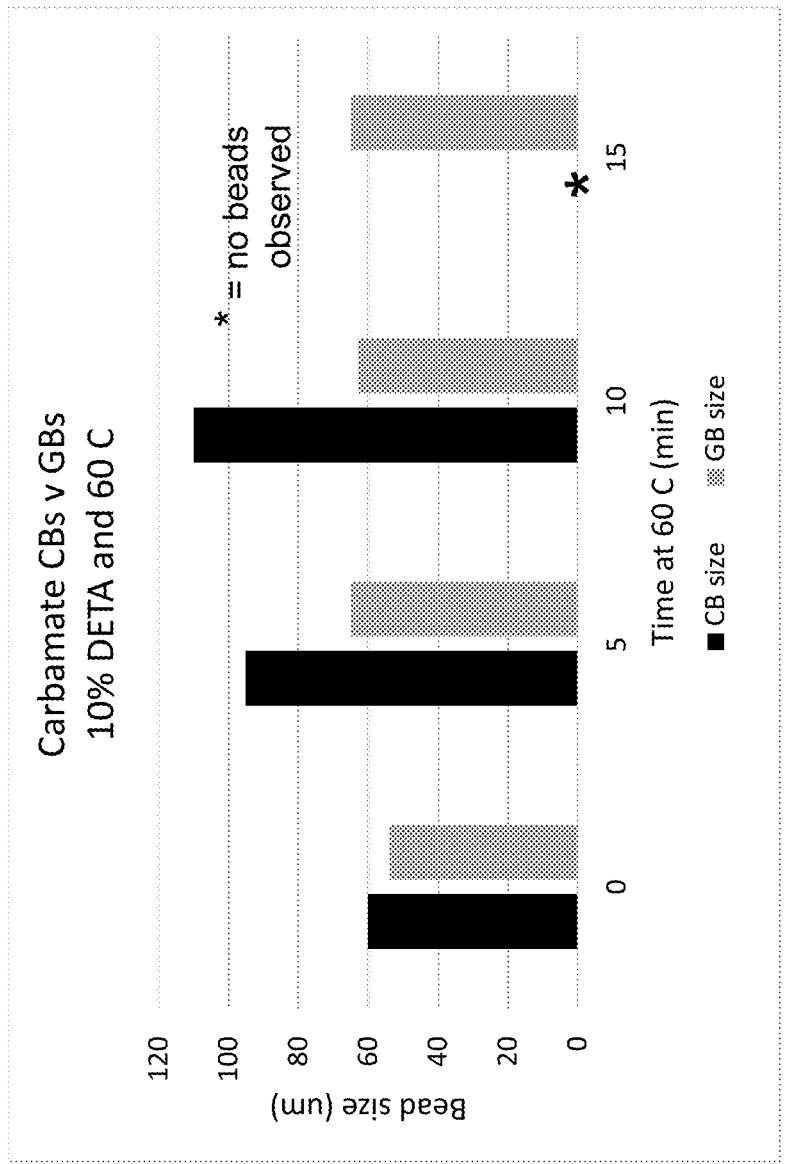
FIG. 33 shows results of degradation of carbamate crosslinks with DETA and heat as described in Example 12.

For further comparison, gel beads (GBs) that do not contain a carbamate linkage (10× Genomics, Inc., Pleasanton, CA, USA) were also treated with 10% DETA and heat and monitored microscopically for degradation. As shown by plot of data depicted in FIG. 33, upon treatment with 10% DETA and 60° C. heat, the CBs with carbamate containing crosslinks undergo swelling from ~60 μm to ~110 μm in the first 10 minutes of treatment and are completely dissolved after 15 minutes of treatment. In contrast, the GBs, which have crosslinks that do not contain a carbamate, undergo no significant change after 15 minutes indicating no degradation in the presence of 10% DETA and heating to 60° C.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A composition comprising:
   (a) cell or cell nucleus; and
   (b) a gel of two or more crosslinked polymers, wherein the two or more crosslinked polymers comprise a copper-chelating group and are configured to form crosslinks distributed throughout the gel and encapsulate the cell or cell nucleus.

2. The composition of claim 1, wherein the crosslinks comprise a picolyl moiety.

3. The composition of claim 1, wherein the copper-chelating group is a picolyl group.

4. The composition of claim 3, wherein the picolyl group is an azido-picolyl group.

5. The composition of claim 1, wherein the composition comprises a copper concentration from 0.3 mM or less.

6. The composition of claim 1, wherein a polymer of the two or more crosslinked polymers comprises at least one member selected from the group consisting of a polyolefin, an olefin copolymer, an acrylic, a vinyl polymer, a polyester, a polyamide, a polyimide, a formaldehyde resin, a polyurethane, an ether polymer, a cellulosic, a thermoplastic elastomer, and a thermoplastic polyurethane.

7. The composition of claim 1, wherein the gel is a hydrogel.

8. The composition of claim 1, wherein a polymer of the two or more crosslinked polymers is a polyacrylamide.

9. The composition of claim 1, further comprising at least one reagent attached by a triazole group to at least one of the two or more crosslinked polymers.

10. The composition of claim 9, wherein the at least one reagent is an oligonucleotide.

11. The composition of claim 10, wherein the oligonucleotide comprises a poly-T sequence.

12. The composition of claim 1, wherein the crosslinks comprise a labile bond.

13. The composition of claim 12, wherein the labile bond is selected from a disulfide bond, a carbamate bond, a peptide bond, or a combination thereof.

14. A method of forming a gel comprising: combining in a partition under copper-catalyzed click chemistry reaction conditions (i) a cell or cell nucleus, and (ii) two or more polymers configured to form crosslinks distributed throughout the gel and encapsulate the cell or cell nucleus, wherein at least one polymer comprises a copper-chelating group.

15. The method of claim 14, wherein the copper-chelating group is a picolyl moiety.

16. The method of claim 14, wherein the copper-catalyzed click chemistry reaction conditions comprise a copper concentration of about 0.3 mM or less.

17. The method of claim 14, wherein the crosslinks formed comprise a labile bond selected from a disulfide bond, a carbamate bond, a peptide bond, or a combination thereof.

18. The method of claim 14, wherein the partition is selected from a well and a discrete droplet in an emulsion.

19. The method of claim 14, wherein a polymer of said two or more polymers comprises at least one member selected from the group consisting of a polyolefin, an olefin copolymer, an acrylic, a vinyl polymer, a polyester, a polyamide, a polyimide, a formaldehyde resin, a polyurethane, an ether polymer, a cellulosic, a thermoplastic elastomer, and a thermoplastic polyurethane.

* * * * *